(12) United States Patent
Yamamoto et al.

(10) Patent No.: US 9,067,952 B2
(45) Date of Patent: *Jun. 30, 2015

(54) THIADIAZOLE, LIGHT-EMITTING ELEMENT, LIGHT-EMITTING APPARATUS, AUTHENTICATION APPARATUS, AND ELECTRONIC DEVICE

(75) Inventors: Hidetoshi Yamamoto, Suwa (JP); Tetsuji Fujita, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 251 days.

This patent is subject to a terminal disclaimer.

(21) Appl. No.: 13/564,376

(22) Filed: Aug. 1, 2012

(65) Prior Publication Data

US 2013/0037784 A1    Feb. 14, 2013

(30) Foreign Application Priority Data

| Aug. 9, 2011 | (JP) | 2011-173660 |
| Aug. 9, 2011 | (JP) | 2011-173661 |
| Aug. 9, 2011 | (JP) | 2011-173662 |

(51) Int. Cl.
*H01L 51/54* (2006.01)
*C07D 513/04* (2006.01)
(Continued)

(52) U.S. Cl.
CPC .......... *C07D 513/04* (2013.01); *C07D 487/04* (2013.01); *H01L 51/0058* (2013.01);
(Continued)

(58) Field of Classification Search
CPC .... C07D 487/04; C07D 513/04; C09K 11/06; C09K 2211/1014; C09K 2211/1044; C09K 2211/1051; H01L 51/0058; H01L 51/0059; H01L 51/0069; H01L 51/5012; H05B 33/14
See application file for complete search history.

(56) References Cited

U.S. PATENT DOCUMENTS

| 4,769,292 A | 9/1988 | Tang et al. |
| 5,104,740 A | 4/1992 | Shinkai et al. |

(Continued)

FOREIGN PATENT DOCUMENTS

| EP | 0 281 381 B1 | 7/1992 |
| JP | A-63-264692 | 11/1988 |

(Continued)

OTHER PUBLICATIONS

Qian et al., J. Phys. Chem. C, vol. 113, No. 4, (2009), pp. 1589-1595.*

(Continued)

*Primary Examiner* — Dawn Garrett

(74) *Attorney, Agent, or Firm* — Oliff PLC

(57) ABSTRACT

The thiadiazole represented by formula (2) or (4), when used as a light-emitting material in a light-emitting element, allows the light-emitting element to emit near-infrared light:

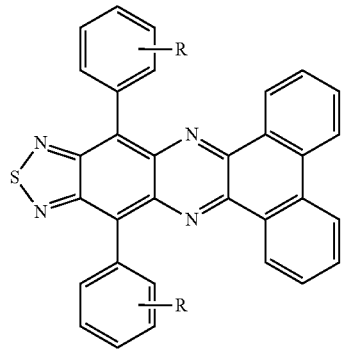
(2)
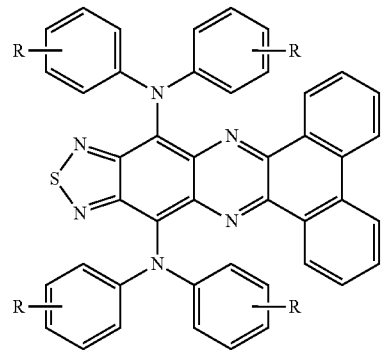
(4)
in formulae (2) and (4), each R independently represents a hydrogen atom, an alkyl group, or a substituted or unsubstituted aryl group. There may be a ring formed by a carbon linkage between two adjacent R's.
19 Claims, 4 Drawing Sheets

(51) Int. Cl.
  *C07D 487/04* (2006.01)
  *C09K 11/06* (2006.01)
  *H05B 33/14* (2006.01)
  *H01L 51/00* (2006.01)
  *H01L 51/50* (2006.01)

(52) U.S. Cl.
  CPC ........ *H01L51/0059* (2013.01); *H01L 51/0069* (2013.01); *H01L 51/5012* (2013.01); *C09K 11/06* (2013.01); *H05B 33/14* (2013.01); *C09K 2211/1014* (2013.01); *C09K 2211/1044* (2013.01); *C09K 2211/1051* (2013.01)

(56) References Cited

U.S. PATENT DOCUMENTS

| | | |
|---|---|---|
| 5,294,869 A | 3/1994 | Tang et al. |
| 5,449,564 A | 9/1995 | Nishio et al. |
| 6,004,685 A | 12/1999 | Antoniadis et al. |
| 6,680,131 B1 | 1/2004 | Ishibashi et al. |
| 7,632,579 B2 | 12/2009 | Ise et al. |
| 7,714,099 B2 | 5/2010 | Morishita et al. |
| 7,902,542 B2 | 3/2011 | Haase et al. |
| 7,919,773 B2 | 4/2011 | Kawakami et al. |
| 7,947,992 B2 | 5/2011 | Yasukawa et al. |
| 7,960,912 B2 | 6/2011 | Yasukawa et al. |
| 8,039,128 B2 | 10/2011 | Watanabe et al. |
| 8,803,138 B2 * | 8/2014 | Fujita et al. ............ 257/40 |
| 2003/0008172 A1 | 1/2003 | Leclerc et al. |
| 2003/0027016 A1 * | 2/2003 | Ara et al. ............. 428/690 |
| 2004/0018382 A1 | 1/2004 | Kinlen |
| 2005/0079381 A1 | 4/2005 | Hamada et al. |
| 2006/0063027 A1 | 3/2006 | Vestweber et al. |
| 2006/0154105 A1 | 7/2006 | Yamamoto et al. |
| 2007/0077453 A1 | 4/2007 | Sano et al. |
| 2007/0285005 A1 | 12/2007 | Itai |
| 2008/0061681 A1 | 3/2008 | Thompson et al. |
| 2008/0067479 A1 | 3/2008 | Kimura et al. |
| 2008/0230123 A1 | 9/2008 | Mitsui et al. |
| 2009/0079335 A1 | 3/2009 | Mitsuya et al. |
| 2009/0091250 A1 | 4/2009 | Yasukawa et al. |
| 2009/0115348 A1 | 5/2009 | Yamazaki et al. |
| 2009/0243476 A1 | 10/2009 | Nomura et al. |
| 2009/0261360 A1 | 10/2009 | Yasukawa et al. |
| 2010/0133434 A1 | 6/2010 | Meng et al. |
| 2010/0155694 A1 | 6/2010 | Miller et al. |
| 2010/0237338 A1 * | 9/2010 | Yamamoto et al. ........... 257/40 |
| 2010/0237990 A1 * | 9/2010 | Amano et al. ............ 340/5.82 |
| 2010/0244671 A1 | 9/2010 | Nomura et al. |
| 2010/0244679 A1 | 9/2010 | Fujita et al. |
| 2010/0317858 A1 | 12/2010 | Konno |
| 2011/0087034 A1 | 4/2011 | Miyata et al. |
| 2011/0253988 A1 | 10/2011 | Molt et al. |
| 2011/0279020 A1 * | 11/2011 | Inoue et al. ............ 313/504 |
| 2011/0303901 A1 | 12/2011 | Cheng et al. |
| 2012/0056213 A1 * | 3/2012 | Yamamoto et al. ........... 257/88 |
| 2012/0091923 A1 | 4/2012 | Kastner-Jung et al. |
| 2012/0262057 A1 | 10/2012 | Fujita et al. |
| 2012/0267615 A1 | 10/2012 | Fujita et al. |
| 2013/0009909 A1 | 1/2013 | Yamazaki et al. |
| 2013/0032791 A1 | 2/2013 | Bazan et al. |
| 2013/0037784 A1 | 2/2013 | Yamamoto et al. |
| 2013/0037785 A1 | 2/2013 | Fujita et al. |
| 2013/0099209 A1 | 4/2013 | Hartmann et al. |
| 2013/0168654 A1 | 7/2013 | Fujita et al. |
| 2013/0221334 A1 | 8/2013 | Yamamoto et al. |

FOREIGN PATENT DOCUMENTS

| | | |
|---|---|---|
| JP | A-2-255788 | 10/1990 |
| JP | A-3-791 | 1/1991 |
| JP | A-3-792 | 1/1991 |
| JP | A-3-162481 | 7/1991 |
| JP | A-3-177486 | 8/1991 |
| JP | A-5-32966 | 2/1993 |
| JP | A-5-214334 | 8/1993 |
| JP | A-5-258859 | 10/1993 |
| JP | A-6-73374 | 3/1994 |
| JP | A-6-93257 | 4/1994 |
| JP | A-6-136359 | 5/1994 |
| JP | A-6-145146 | 5/1994 |
| JP | A-6-240246 | 8/1994 |
| JP | A-10-330295 | 12/1998 |
| JP | A-11-233261 | 8/1999 |
| JP | A-2000-91073 | 3/2000 |
| JP | 2001-097949 A | 4/2001 |
| JP | A-2001-110570 | 4/2001 |
| JP | A-2002-097465 | 4/2002 |
| JP | A-2003-055652 | 2/2003 |
| JP | 2003-109760 A | 4/2003 |
| JP | 2004-002297 A | 1/2004 |
| JP | A-2005-063938 | 3/2005 |
| JP | 2005-531552 A | 10/2005 |
| JP | 2006-045398 A | 2/2006 |
| JP | 2006-511939 A | 4/2006 |
| JP | A-2007-115626 | 5/2007 |
| JP | 2008-069100 A | 3/2008 |
| JP | A-2009-016693 | 1/2009 |
| JP | 2009-049094 A | 3/2009 |
| JP | 2009-256343 A | 11/2009 |
| JP | 2010-147179 A | 7/2010 |
| JP | 2010-254674 A | 11/2010 |
| WO | 03-095445 A | 11/2003 |
| WO | 2004-058911 A2 | 7/2004 |
| WO | WO 2008/069322 A1 | 6/2008 |

OTHER PUBLICATIONS

Kawabe et al., "Electroluminescence of Green Light Region in Doped Anthracene," *Japanese of Journal of Applied Physics*, 1971, pp. 527-529, vol. 10.

Debad et al., "Dibenzotetraphenylperiflanthene: Synthesis, Photophysical Properties, and Electrogenerated Chemiluminescence," *Journal of American Chemistry Society*, 1996, pp. 2374-2379, vol. 118, American Chemistry Society.

Du et al., "Efficient Non-doped Near Infrared Organic Light-Emitting Devices Based on Fluorophores with Aggregation-Induced Emission Enhancement" *Chemistry of Materials* (2012) pp. 2178-2185.

Jan. 10, 2014 Office Action issued in U.S. Appl. No. 13/445,523.

Jun. 18, 2014 Office Action issued in U.S. Appl. No. 13/445,523.

Kajii et al., "Visible to near-infrared organic light-emitting diodes using phosphorescent materials by solution process," *Thin Solid Films* (2009) pp. 551-554.

U.S. Appl. No. 13/445,523 in the name of Fujita et al., filed Apr. 12, 2012.

U.S. Appl. No. 13/564,384 in the name of Fujita et al., filed Aug. 1, 2012.

U.S. Appl. No. 14/319,410 in the name of Fujita et al., filed Jun. 30, 2014.

U.S. Appl. No. 13/773,033 in the name of Yamamoto et al., filed Feb. 21, 2013.

U.S. Appl. No. 14/055,241 in the name of Fujita et al., filed Oct. 16, 2013.

Sep. 5, 2014 Notice of Allowance issued in U.S. Appl. No. 13/445,523.

Aug. 15, 2014 Office Action issued in U.S. Appl. No. 13/564,384.

Mar. 26, 2014 Notice of Allowance issued in U.S. Appl. No. 13/727,339.

Oct. 3, 2014 Office Action issued in U.S. Appl. No. 14/319,410.

U.S. Appl. No. 13/444,107 in the name of Fujita et al., filed Apr. 11, 2012.

Jan. 22, 2015 Office Action issued in U.S. Appl. No. 13/564,384.

Apr. 22, 2015 Office Action issued in U.S. Appl. No. 13/773,033.

U.S. Appl. No. 14/693,484, filed Apr. 22, 2015 in the name of Yamamoto et al.

U.S. Appl. No. 14/700,751, filed Apr. 30, 2015 in the name of Fujita et al.

* cited by examiner

THIADIAZOLE, LIGHT-EMITTING ELEMENT, LIGHT-EMITTING APPARATUS, AUTHENTICATION APPARATUS, AND ELECTRONIC DEVICE

CROSS REFERENCES TO RELATED APPLICATIONS

The present application claims priority to Japanese Patent Application No. 2011-173660, Japanese Patent Application No. 2011-173661, and Japanese Patent Application No. 2011-173662 filed in the Japanese Patent Office on Aug. 9, 2011, the entire contents of which are incorporated herein by reference.

BACKGROUND

1. Technical Field

The present invention relates to a thiadiazole, a light-emitting element, a light-emitting apparatus, an authentication apparatus, and an electronic device.

2. Related Art

Organic electroluminescent elements (organic EL elements) are light-emitting elements composed of an anode, a cathode, and at least one organic light-emitting layer disposed between them. Upon the application of an electric field between the anode and the cathode, holes in the anode and electrons in the cathode are injected into the light-emitting layer or layers and generate excitons. When these excitons disappear (i.e., when the electrons and the holes recombine), energy is released, at least in part in the form of fluorescence or phosphorescence.

A known example of such a light-emitting element is one that emits a long-wavelength light of more than 700 nm (e.g., see JP-A-2000-091073 and JP-A-2001-110570).

In a light-emitting element of those types that are described in these patent publications, for example, the light-emitting layer or layers are doped with a compound that contains both electron-donating and electron-withdrawing functional groups, namely amine and a nitrile group, in the molecule. As a result, the light-emitting element can emit light with such a long wavelength. However, it has been impossible to provide such near-infrared-emitting elements with high efficiency and long life.

A light-emitting element that is planar, that can emit near-infrared light, and that is of high efficiency and long life are can be used as, for example, a light source for biometric authentication, in which individuals are verified on the basis of their biological traits, such as vein patterns or fingerprints. Light-emitting elements satisfying these requirements are therefore in demand.

SUMMARY

An advantage of some aspects of the invention is that they provide a near-infrared-emitting, high-efficiency, and long-life thiadiazole, a near-infrared-emitting, high-efficiency, and long-life light-emitting element, and a light-emitting apparatus, an authentication apparatus, and an electronic device provided with such a light-emitting element.

The thiadiazole according to an aspect of the invention is represented by formula (2) or (4):

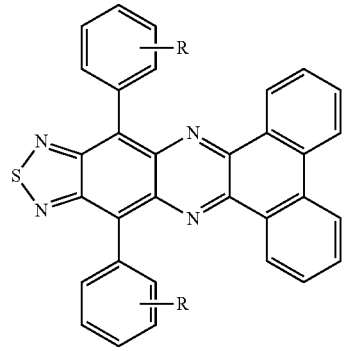

(2)

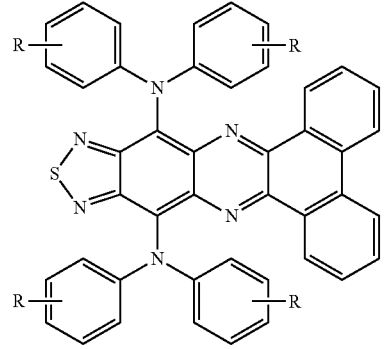

(4)

[In formulae (2) and (4), each R independently represents a hydrogen atom, an alkyl group, or a substituted or unsubstituted aryl group. There may be a ring formed by two adjacent carbon atoms that bond to each other.]

The thiadiazole according to this aspect of the invention can be used as a light-emitting material.

When used in an organic EL element as a light-emitting material, for example, this thiadiazole allows the EL element to emit near-infrared light.

The light-emitting element according to another aspect of the invention has an anode, a cathode, and a light-emitting layer disposed between the anode and the cathode. This light-emitting layer, which emits light when electric current flows between the anode and the cathode, contains a compound represented by formula (1) as a light-emitting material and a compound represented by formula IRH-1 as a host material for the light-emitting material.

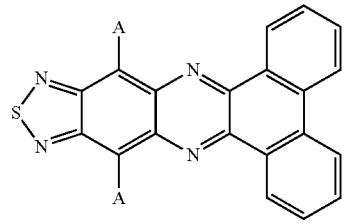

(1)

[In formula (1), each A independently represents a hydrogen atom, an alkyl group, a substituted or unsubstituted aryl group, a substituted or unsubstituted aryl amino group, or a substituted or unsubstituted triarylamine.]

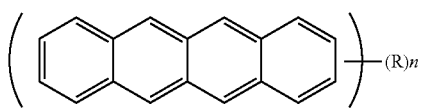

[In formula IRH-1, n represents a natural number of 1 to 12 and R represents a substituent or a functional group, and each R is independently a hydrogen atom, an alkyl group, a substituted or unsubstituted aryl group, or a substituted or unsubstituted aryl amino group.]

This configuration, in which a compound represented by formula (1) is used as a light-emitting material, allows the light-emitting element to emit light in a wavelength range of not less than 700 nm (the near-infrared range).

Furthermore, the tetracene-based host material can transfer energy from itself to the light-emitting material in an efficient way and thereby imparts excellent light emission efficiency to the light-emitting element.

Moreover, tetracene-based materials are inert (highly resistant) to electrons and holes. Thus, the use of the tetracene-based host material also extends the life of the light-emitting layer and, accordingly, prolongs the life of the light-emitting element.

In the light-emitting element according to this aspect of the invention, it is preferred that the compound represented by formula (1) is a compound represented by any of formulae (2) to (4).

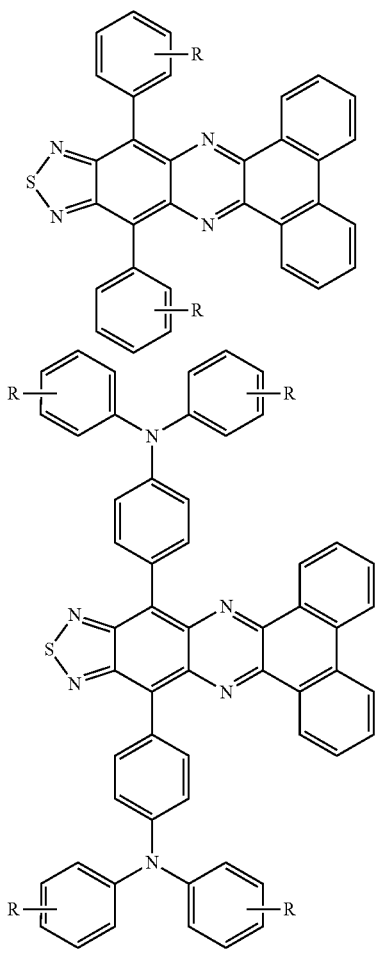

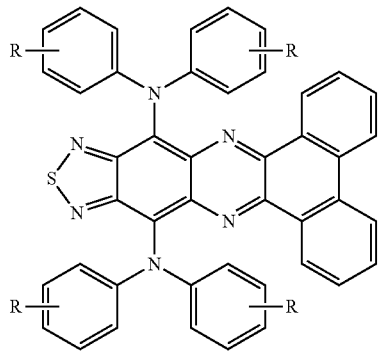

[In formulae (2) to (4), each R independently represents a hydrogen atom, an alkyl group, or a substituted or unsubstituted aryl group. There may be a ring formed by two adjacent carbon atoms that bond to each other.]

This arrangement leads to the prevention of unwanted interactions between the host material and the light-emitting material and thereby enhances the light emission efficiency of the light-emitting element and the resistance of the host material to electrons and holes and, accordingly, extends the life of the light-emitting element.

In the light-emitting element according to this aspect of the invention, it is also preferred that the compound represented by formula IRH-1, the host material, is a compound represented by formula IRH-2.

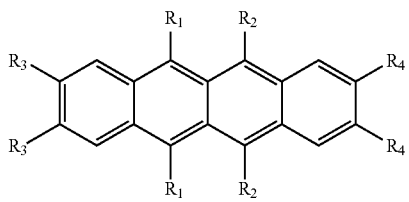

[In formula IRH-2, each of $R_1$ to $R_4$ independently represents a hydrogen atom, an alkyl group, a substituted or unsubstituted aryl group, or a substituted or unsubstituted aryl amino group. Some or all of $R_1$ to $R_4$ may be the same, or they may be all different.]

This arrangement provides overvoltage protection during continuous operation while enhancing the light emission efficiency of the light-emitting element and extending the life of the light-emitting element.

In the light-emitting element according to this aspect of the invention, it is also preferred that the compound represented by formula IRH-1, the host material, is a compound represented by formula IRH-3.

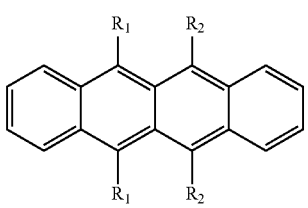

[In formula IRH-3, each of $R_1$ and $R_2$ independently represents a hydrogen atom, an alkyl group, a substituted or unsubstituted aryl group, or a substituted or unsubstituted aryl amino group. $R_1$ and $R_2$ may be the same or different.]

This arrangement also provides overvoltage protection during continuous operation while enhancing the light emission efficiency of the light-emitting element and extending the life of the light-emitting element.

In the light-emitting element according to this aspect of the invention, it is also preferred that an electron transport layer, which is a layer having the capability of transporting electrons, is provided between the cathode and the light-emitting layer so as to be in contact with the light-emitting layer and that this electron transport layer contains a compound having an azaindolizine skeleton and an anthracene skeleton in the molecule as an electron transport material.

The use of an electron transport compound having an azaindolizine skeleton and an anthracene skeleton in the molecule in the electron transport layer, which is formed in contact with the light-emitting layer, allows efficient transport of electrons from the electron transport layer to the light-emitting layer and thereby imparts excellent light emission efficiency to the light-emitting element.

Furthermore, the efficient electron transport from the electron transport layer to the light-emitting layer lowers the driving voltage of the light-emitting element and thereby extends the life of the light-emitting element.

Moreover, compounds having an azaindolizine skeleton and an anthracene skeleton in the molecule are inert (highly resistant) to electrons and holes. This also helps extend the life of the light-emitting element.

The light-emitting element according to yet another aspect of the invention has an anode, a cathode, a light-emitting layer disposed between the anode and the cathode, and an electron transport layer provided between the cathode and the light-emitting layer so as to be in contact with the light-emitting layer. The light-emitting layer, which emits light when electric current flows between the anode and the cathode, contains a compound represented by formula (1) as a light-emitting material, and the electron transport layer, which has the capability of transporting electrons, contains a compound having an azaindolizine skeleton and an anthracene skeleton in the molecule as an electron transport material.

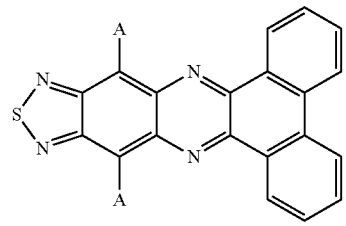

(1)

[In formula (1), each A independently represents a hydrogen atom, an alkyl group, a substituted or unsubstituted aryl group, a substituted or unsubstituted aryl amino group, or a substituted or unsubstituted triarylamine.]

This configuration, in which a compound represented by formula (1) is used as a light-emitting material, also allows the light-emitting element to emit light in a wavelength range of not less than 700 nm (the near-infrared range).

Furthermore, the use of a compound having an azaindolizine skeleton and an anthracene skeleton in the molecule as an electron transport material in the electron transport layer, which is formed in contact with the light-emitting layer, allows efficient transport of electrons from the electron transport layer to the light-emitting layer and thereby imparts excellent light emission efficiency to the light-emitting element.

The efficient electron transport from the electron transport layer to the light-emitting layer lowers the driving voltage of the light-emitting element and thereby extends the life of the light-emitting element.

Moreover, compounds having an azaindolizine skeleton and an anthracene skeleton in the molecule are inert (highly resistant) to electrons and holes. This also helps extend the life of the light-emitting element.

In the light-emitting element according to this aspect of the invention, it is preferred that the compound represented by formula (1) is a compound represented by any of formulae (2) to (4).

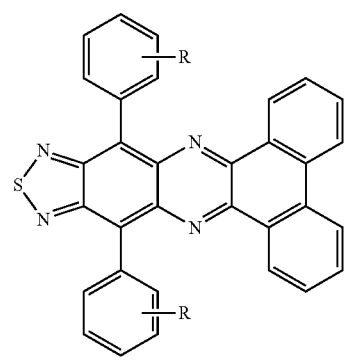

(2)

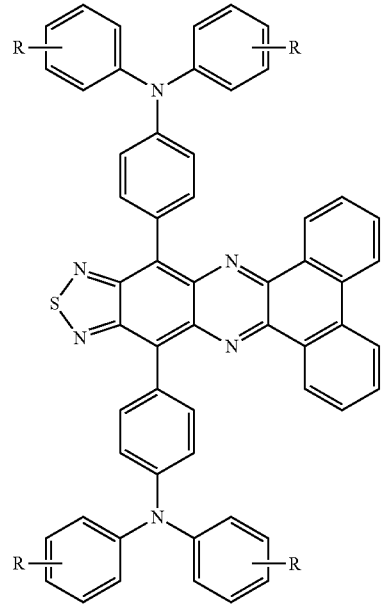

(3)

(4)

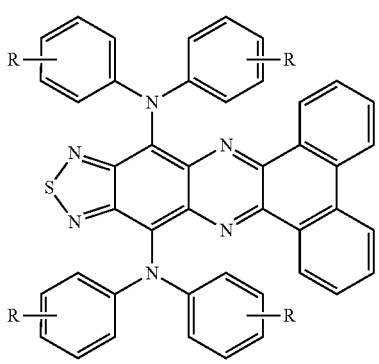

[In formulae (2) to (4), each R independently represents a hydrogen atom, an alkyl group, or a substituted or unsubstituted aryl group. There may be a ring formed by two adjacent carbon atoms that bond to each other.]

This arrangement enhances the efficiency of the light-emitting element and extends the life of the light-emitting element.

In the light-emitting element according to this aspect of the invention, it is also preferred that the light-emitting layer contains a compound represented by formula IRH-4 as a host material for the light-emitting material.

IRH-4

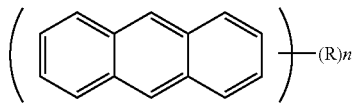

[In formula IRH-4, n represents a natural number of 1 to 10 and R represents a substituent or a functional group, and each R is independently a hydrogen atom, an alkyl group, a substituted or unsubstituted aryl group, or a substituted or unsubstituted aryl amino group.]

This arrangement allows more efficient transport of electrons from the anthracene skeleton moiety of the electron transport material in the electron transport layer to the anthracene-based material in the light-emitting layer.

The light-emitting element according to a different aspect of the invention has an anode, a cathode, and a light-emitting layer disposed between the anode and the cathode. This light-emitting layer, which emits light when electric current flows between the anode and the cathode, contains a compound represented by formula (1) as a light-emitting material and a compound represented by formula IRH-4 as a host material for the light-emitting material.

(1)

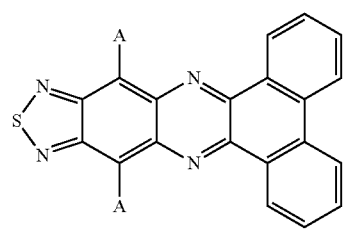

[In formula (1), each A independently represents a hydrogen atom, an alkyl group, a substituted or unsubstituted aryl group, a substituted or unsubstituted aryl amino group, or a substituted or unsubstituted triarylamine.]

IRH-4

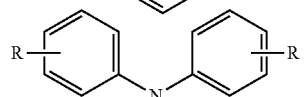

[In formula IRH-4, n represents a natural number of 1 to 12 and R represents a substituent or a functional group, and each R is independently a hydrogen atom, an alkyl group, a substituted or unsubstituted aryl group, or a substituted or unsubstituted aryl amino group.]

This configuration, in which a compound represented by formula (1) is used as a light-emitting material, also allows the light-emitting element to emit light in a wavelength range of not less than 700 nm (the near-infrared range).

Furthermore, the anthracene-based host material can transfer energy from itself to the light-emitting material in an efficient way and thereby imparts excellent light emission efficiency to the light-emitting element.

Moreover, anthracene-based materials are inert (highly resistant) to electrons and holes. Thus, the use of the anthracene-based host material also extends the life of the light-emitting layer and, accordingly, prolongs the life of the light-emitting element.

In the light-emitting element according to this aspect of the invention, it is preferred that the compound represented by formula (1) is a compound represented by any of formulae (2) to (4).

(2)

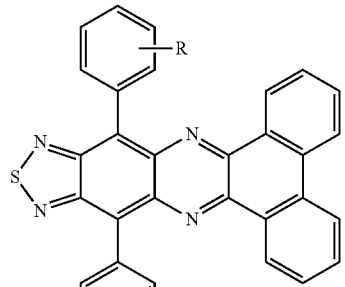

(3)

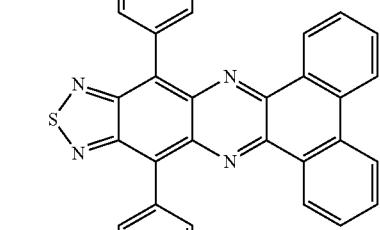

-continued (4)

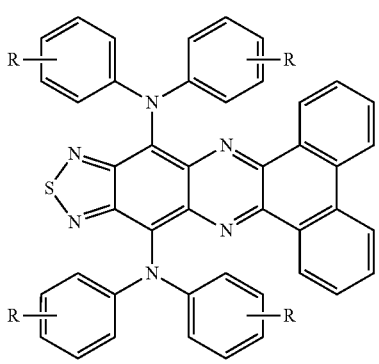

[In formulae (2) to (4), each R independently represents a hydrogen atom, an alkyl group, or a substituted or unsubstituted aryl group. There may be a ring formed by two adjacent carbon atoms that bond to each other.]

In the light-emitting element according to this aspect of the invention, it is also preferred that the compound represented by formula IRH-4, the host material, is a compound represented by formula IRH-5.

IRH-5

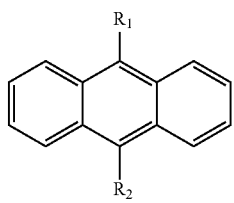

[In formula IRH-5, each of $R_1$ and $R_2$ independently represents a hydrogen atom, an alkyl group, a substituted or unsubstituted aryl group, or a substituted or unsubstituted aryl amino group, $R_1$ and $R_2$ may be the same or different.]

This arrangement provides overvoltage protection during continuous operation while enhancing the light emission efficiency of the light-emitting element and extending the life of the light-emitting element.

In the light-emitting element according to this aspect of the invention, it is also preferred that the compound represented by formula IRH-4, the host material, is a compound represented by formula IRH-7.

IRH-7

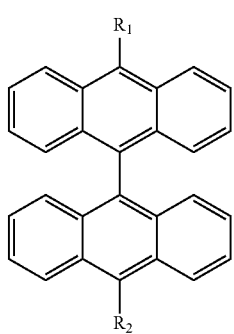

[In formula IRH-7, each of $R_1$ and $R_2$ independently represents a hydrogen atom, an alkyl group, a substituted or unsubstituted aryl group, or a substituted or unsubstituted aryl amino group. $R_1$ and $R_2$ may be the same or different.]

This arrangement also provides overvoltage protection during continuous operation while enhancing the improved light emission efficiency of the light-emitting element and extending the life of the light-emitting element.

In the light-emitting element according to this aspect of the invention, it is also preferred that the compound represented by formula IRH-4, the host material, is a compound represented by formula IRH-8.

IRH-8

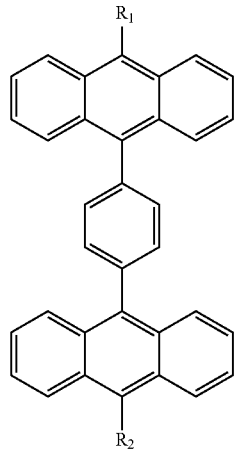

[In formula IRH-8, each of $R_1$ and $R_2$ independently represents a hydrogen atom, an alkyl group, a substituted or unsubstituted aryl group, or a substituted or unsubstituted aryl amino group. $R_1$ and $R_2$ may be the same or different.]

This arrangement also provides overvoltage protection during continuous operation while enhancing the light emission efficiency of the light-emitting element and extending the life of the light-emitting element.

The light-emitting apparatus according to a different aspect of the invention is provided with a light-emitting element according to any relevant aspect of the invention.

The light-emitting apparatus configured in this way can emit near-infrared light and has excellent reliability because of the high efficiency and long life of the light-emitting element used therein.

The authentication apparatus according to a different aspect of the invention is provided with a light-emitting element according to any relevant aspect of the invention.

The authentication apparatus configured in this way allows biometric authentication using near-infrared light and has excellent reliability because of the high efficiency and long life of the light-emitting element used therein.

The electronic device according to a different aspect of the invention is provided with a light-emitting element according to any relevant aspect of the invention.

The electronic device configured in this way has excellent reliability because of the high efficiency and long life of the light-emitting element used therein.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
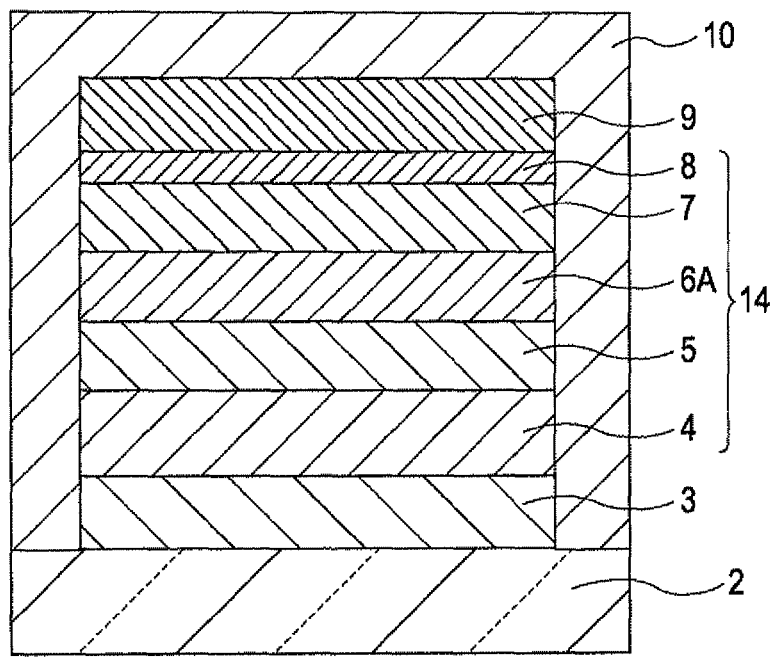
FIG. 1 schematically illustrates a cross-section of a light-emitting element according to Embodiment 1 of an aspect of the invention.

The following describes preferred embodiments of the thiadiazole, light-emitting elements, light-emitting apparatus, authentication apparatus, and electronic device according to aspects of the invention with reference to attached drawings. These embodiments are intended to illustrate some aspects of the invention and should not be construed as limiting the invention. The shapes, combinations, and other information about components given in the following embodiments are only illustrative and can be modified in various ways depending on design requirements and other conditions without departing from the gist of the invention. Furthermore, the structures illustrated in the drawings mentioned in the following may be different from the reality in the relative dimensions and the numbers of components and other features in order for better understanding of the individual configurations.

Embodiment 1

Configuration of the Light-Emitting Element

FIG. 1 schematically illustrates a cross-section of a light-emitting element according to Embodiment 1 of an aspect of the invention. For convenience of explanation, the top and bottom in FIG. 1 are hereinafter regarded as the top and bottom of the light-emitting element, respectively.

The light-emitting element (electroluminescence element) 1A illustrated in FIG. 1 has an anode 3, a hole injection layer 4, a hole transport layer 5, a light-emitting layer 6A, an electron transport layer 7, an electron injection layer 8, and a cathode 9 stacked in this order. In other words, the light-emitting element 1A has a laminate 14 disposed between the anode 3 and the cathode 9, and the laminate 14 contains the hole injection layer 4, the hole transport layer 5, the light-emitting layer 6A, the electron transport layer 7, and the electron injection layer 8 stacked in this order from the anode 3 side to the cathode 9 side.

The entire light-emitting element 1A is formed on a substrate 2 and sealed with a sealing member 10.

In the light-emitting element 1A configured in this way, the light-emitting layer 6A receives electrons supplied (injected) from the cathode 9 side and holes supplied (injected) from the anode 3 side when driving voltage is applied to the anode 3 and the cathode 9. Then, in the light-emitting layer 6A, the injected holes and electrons generate excitons. When these excitons disappear (i.e., when the electrons and the holes recombine), energy is released, at least in part in the form of fluorescence or phosphorescence (light emission). As a result, the light-emitting element 1A emits light.

An important feature of this light-emitting element 1A is that it can emit near-infrared light because, as detailed later in this specification, its light-emitting layer 6A contains a thiadiazole as a light-emitting material. The term near-infrared range as used in this specification represents the wavelength range from 700 nm to 1500 nm, both inclusive.

The substrate 2 supports the anode 3. The light-emitting element 1A according to this embodiment emits light through the substrate 2 (the bottom-emission structure), and thus the substrate 2 and the anode 3 are substantially transparent (colorless and transparent, colored and transparent, or translucent).

Examples of materials for the substrate 2 are resin materials such as polyethylene terephthalate, polyethylene naphthalate, polypropylene, cycloolefin polymers, polyamides, polyethersulfone, polymethyl methacrylate, polycarbonates, and polyarylates, glass materials such as quartz glass and soda lime glass, and so forth, and these materials may be used singly or in combination of two or more kinds.

The average thickness of the substrate 2 configured in this way is not particularly limited; however, it is preferably on the order of 0.1 mm to 30 mm and more preferably on the order of 0.1 mm to 10 mm.

When the light-emitting element 1A emits light through the surface opposite to the substrate 2 (the top-emission structure), the substrate 2 may be a transparent substrate or an opaque substrate.

Examples of appropriate opaque substrates include those made of ceramic materials such as alumina, those made of metals such as stainless steel and coated with an oxide film (an insulating film), and those made of resin materials.

In the light-emitting element 1A configured in this way, furthermore, the distance between the anode 3 and the cathode 9 (i.e., the average thickness of the laminate 14) is preferably in a range of 100 nm to 500 nm, more preferably 100 nm to 300 nm, and even more preferably 100 nm to 250 nm. This allows easy and consistent control of the driving voltage of the light-emitting element 1A within the practical range.

In the following, the individual components of the light-emitting element 1A are detailed.

Anode

The anode 3 injects holes into the hole transport layer 5 via the hole injection layer 4, which will detailed later in this specification. Preferably, the anode 3 is made of a material having a high work function and excellent electroconductivity.

Examples of materials for the anode 3 are oxides such as ITO (indium tin oxide), IZO (indium zinc oxide), $In_2O_3$, $SnO_2$, Sb-containing $SnO_2$, and Al-containing ZnO, metals such as Au, Pt, Ag, and Cu, alloys of these metals, and so forth, and these materials may be used singly or in combination of two or more kinds.

Particularly preferably, the anode 3 is made of ITO. ITO has transparency, has a high work function, and has excellent electroconductivity, and these features of ITO allow efficient injection of holes from the anode 3 to the hole injection layer 4.

It is also preferred that the surface of the anode 3 on the hole injection layer 4 side (the top surface in FIG. 1) has been treated with plasma. This improves the chemical and mechanical stability of the interface between the anode 3 and the hole injection layer 4 and thereby helps hole injection from the anode 3 to the hole injection layer 4. A process of plasma treatment for this purpose will be detailed later in this specification in the description of a manufacturing method of the light-emitting element 1A.

The average thickness of the anode 3 configured in this way is not particularly limited; however, it is preferably on the order of 10 nm to 200 nm and more preferably on the order of 50 nm to 150 nm.

Cathode

On the other hand, the cathode 9 injects electrons into the electron transport layer 7 via the electron injection layer 8, which will be detailed later in this specification. Preferably, the cathode 9 is made of a material having a low work function.

Examples of materials for the cathode 9 are Li, Mg, Ca, Sr, La, Ce, Er, Eu, Sc, Y, Yb, Ag, Cu, Al, Cs, and Rb, alloys of these metals, and so forth, and these metals or alloys may be used singly or in combination of two or more kinds (e.g., to form a laminate consisting of some layers made of different materials or a hybrid layer containing different materials).

In particular, when the cathode 9 is made of an alloy, examples of preferred alloys include those containing stable metal elements such as Ag, Al, and Cu, or more specifically MgAg, AlLi, CuLi, and so forth. When used as material for the cathode 9, these alloys improve the electron injection efficiency and stability of the cathode 9.

The average thickness of the cathode 9 configured in this way is not particularly limited; however, it is preferably on the order of 100 nm to 10000 nm and more preferably on the order of 100 nm to 500 nm.

In this embodiment, the light-emitting element 1A has the bottom-emission structure, and thus the cathode 9 does not have to be transparent to light. When the top-emission structure is used, however, it is preferred that the average thickness of the cathode 9 is on the order of 1 nm to 50 nm because the outgoing light should be allowed to pass through the cathode 9.

Hole Injection Layer

The hole injection layer 4 improves the efficiency of the injection of holes from the anode 3 (i.e., this layer has hole injection properties).

This configuration, in which the hole injection layer 4 is placed between the anode 3 and the hole transport layer 5, which will be detailed later in this specification, helps hole injection from the anode 3 and thereby enhances the light emission efficiency of the light-emitting element 1A.

The hole injection layer 4 contains a material having hole injection properties (i.e., a hole injection material).

The hole injection material used in the hole injection layer 4 is not particularly limited. Examples of appropriate materials include copper phthalocyanine, 4,4',4"-tris(N,N-phenyl-3-methylphenylamino)triphenylamine (m-MTDATA), and N,N'-bis(4-diphenylaminophenyl)-N,N"-diphenylbiphenyl-4,4'-diamine.

Preferably, the hole injection layer 4 contains an amine-based hole injection material because this kind of material has excellent hole injection and hole transport properties. More preferably, the hole injection layer contains a diaminobenzene derivative, a benzidine derivative (a material having a benzidine skeleton), or a triamine or tetramine having both diaminobenzene and benzidine units in the molecule.

The average thickness of the hole injection layer 4 configured in this way is not particularly limited; however, it is preferably on the order of 5 nm to 90 nm and more preferably on the order of 10 nm to 70 nm.

Incidentally, the hole injection layer 4 may be omitted, depending on the composition of the anode 3 and the hole transport layer 5.

Hole Transport Layer

The hole transport layer 5 receives the holes injected thereinto from the anode 3 via the hole injection layer 4 and transmits them to the light-emitting layer 6 (i.e., this layer has hole transport properties).

The hole transport layer 5 contains a material having hole transport properties (i.e., a hole transport material).

The hole transport material used in the hole transport layer 5 may be a p-type polymer, a p-type low-molecular-weight compound, or any appropriate combination of them, and more specific examples thereof are tetraarylbenzidine derivatives such as N,N'-di(1-naphthyl)-N,N'-diphenyl-1,1'-diphenyl-4,4'-diamine (NPD) and N,N'-diphenyl-N,N'-bis(3-methylphenyl)-1,1'-diphenyl-4,4'-diamine (TPD), tetraaryldiaminofluorenes and their derivatives (amines), and so forth, and these compounds or derivatives may be used singly or in combination of two or more kinds.

Preferably, the hole transport layer 5 contains an amine-based hole transport material because this kind of material has excellent hole injection and hole transport properties. More preferably, the hole transport layer 5 contains a benzidine derivative (a material having a benzidine skeleton).

The average thickness of the hole transport layer 5 configured in this way is not particularly limited; however, it is preferably on the order of 5 nm to 90 nm and more preferably on the order of 10 nm to 70 nm.

Light-Emitting Layer

The light-emitting layer 6A emits light when electric current flows between the anode 3 and cathode 9 mentioned above.

For this purpose, the light-emitting layer 6A contains a light-emitting material.

More specifically, this light-emitting layer 6A contains a light-emitting material represented by formula (1) (hereinafter, also simply referred to as a thiadiazole).

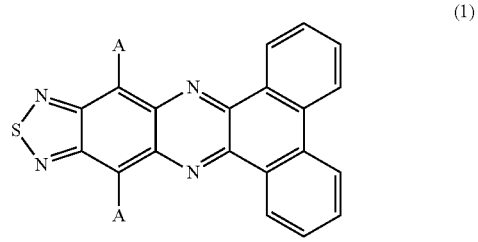

(1)

[In formula (1), each A independently represents a hydrogen atom, an alkyl group, a substituted or unsubstituted aryl group, a substituted or unsubstituted aryl amino group, or a substituted or unsubstituted triarylamine.]

This type of thiadiazole allows the light-emitting layer 6A to emit light in a wavelength range of not less than 700 nm (the near-infrared range).

Preferably, the light-emitting layer 6A contains a light-emitting material represented by any of formulae (2) to (4); this leads to more efficient and prolonged light emission. Specific examples of particularly preferred compounds are those represented by formulae D-1 to D-3.

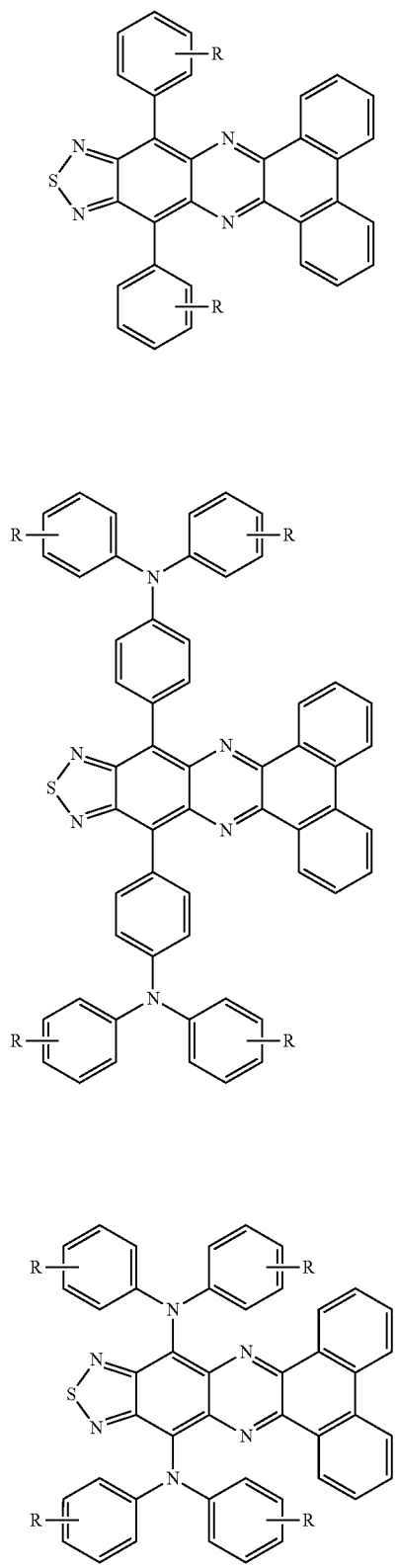

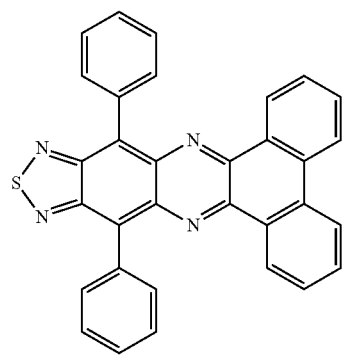
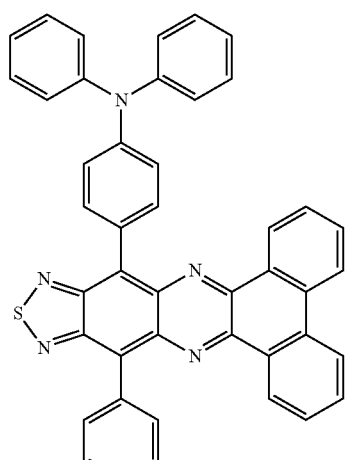
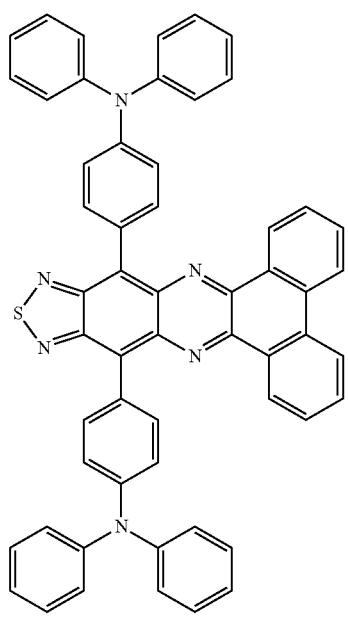

[In formulae (2) to (4), each R independently represents a hydrogen atom, an alkyl group, or a substituted or unsubstituted aryl group. There may be a ring formed by two adjacent carbon atoms that bond to each other.]

Incidentally, besides this light-emitting material, the light-emitting layer 6A may contain other light-emitting materials (e.g., fluorescent or phosphorescent materials).

The light-emitting layer 6A further contains, in addition to the light-emitting material described above, a host material that can be doped with (or can carry) this light-emitting material as guest material (dopant). This host material generates excitons from the injected holes and electrons and transfers the energy of the excitons to the light-emitting material (by Forster energy transfer or Dexter energy transfer) to excite the light-emitting material, thereby improving the light emission efficiency of the light-emitting element 1A. This type of host material can be used by, for example, doping the host material with its guest material, which is the light-emitting material in this case, as dopant.

An important thing here is that a tetracene-based material (a naphthacene-based material), which is classified into acene-based materials, is used as a host material for this purpose.

Acene-based materials are unlikely to undergo unwanted interactions with light-emitting materials of the above-mentioned types. Furthermore, the use of an acene-based host material (in particular, tetracene-based one) allows efficient energy transfer to the light-emitting material. Some possible reasons for this are the following: (a) energy transfer from the triplet excited state of the acene-based material induces the singlet excited state of the light-emitting material; (b) the overlap between the π electron cloud of the acene-based material and the electron cloud of the light-emitting material is large; and (c) the overlap between the emission spectrum of the acene-based material and the absorption spectrum of the light-emitting material is large.

For these and other reasons, the use of an acene-based host material improves the light emission efficiency of the light-emitting element 1A.

Furthermore, acene-based materials are highly resistant to electrons and holes and have excellent thermal stability, and these features of acene-based materials help extend the life of the light-emitting element 1A. Additionally, when the light-emitting layer 6A is formed by a gas-phase deposition process, the excellent thermal stability of the acene-based host material protects the host material from decomposition by heat during the film formation process. This ensures the excellent film quality of the light-emitting layer 6A, which additionally helps enhance the light emission efficiency and extend the life of the light-emitting element 1A.

Moreover, acene-based materials are inherently unlikely to emit light, and this feature helps prevent the host material from affecting the emission spectrum of the light-emitting element 1A.

The tetracene-based material is not particularly limited as long as it has at least one tetracene skeleton in the molecule and can perform the functions of a host material such as those mentioned above. However, it is preferably a compound represented by formula IRH-1, more preferably a compound represented by formula IRH-2, and even more preferably a compound represented by formula IRH-3. The use of any of these compounds provides overvoltage protection during continuous operation while enhancing the light emission efficiency of the light-emitting element 1A and extending the life of the light-emitting element 1A.

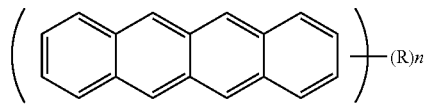

IRH-1

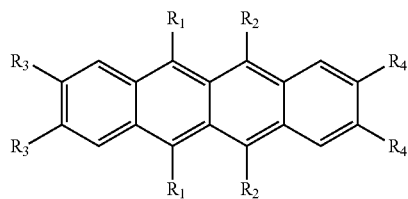

IRH-2

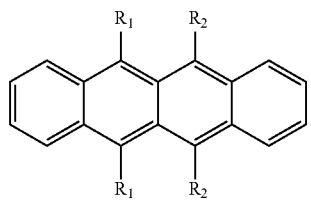

IRH-3

[In formula IRH-1, n represents a natural number of 1 to 12 and R represents a substituent or a functional group, and each R is independently a hydrogen atom, an alkyl group, a substituted or unsubstituted aryl group, or a substituted or unsubstituted aryl amino group. In formulae IRH-2 and IRH-3, each of $R_1$ to $R_4$ independently represents a hydrogen atom, an alkyl group, a substituted or unsubstituted aryl group, or a substituted or unsubstituted aryl amino group. Some or all of $R_1$ to $R_4$ may be the same, or they may be all different.]

It is also preferred that the tetracene-based material is composed of carbon atoms and hydrogen atoms. This more effectively prevents the host material and the light-emitting material from undergoing unwanted interactions and thereby further enhances the light emission efficiency of the light-emitting element 1A. Furthermore, the resistance of the host material to electrons and holes is further enhanced as well. As a result, this arrangement provides overvoltage protection during continuous operation while extending the life of the light-emitting element 1A.

Specific examples of preferred tetracene-based materials include the compounds represented by formulae H1-1 to H1-11 and the compounds represented by formulae H1-12 to H1-27.

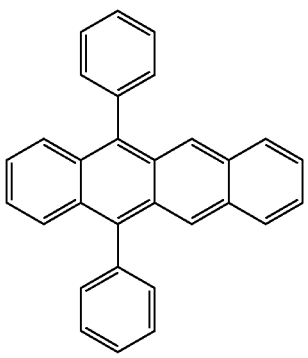

H1-1

-continued
H1-2
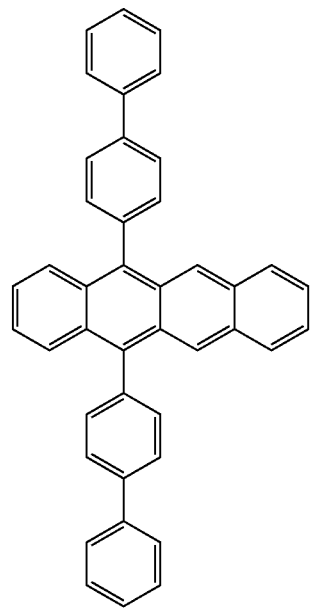
H1-3
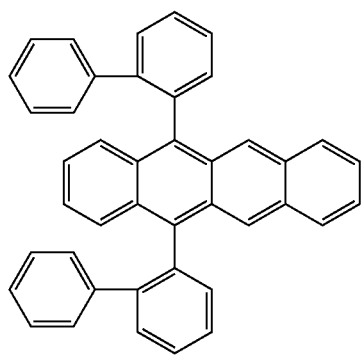
H1-4
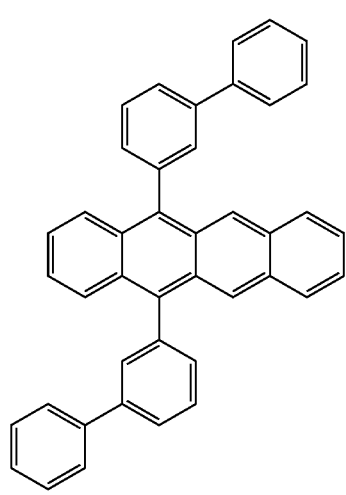
-continued
H1-5
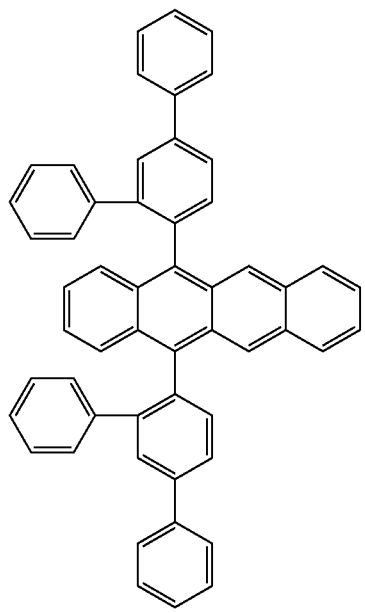
H1-6
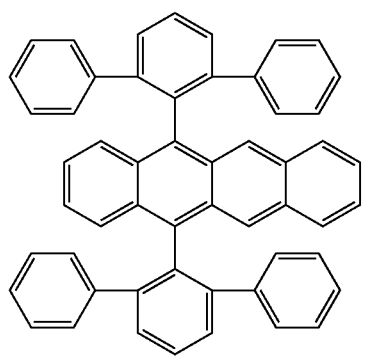
H1-7

-continued
H1-8
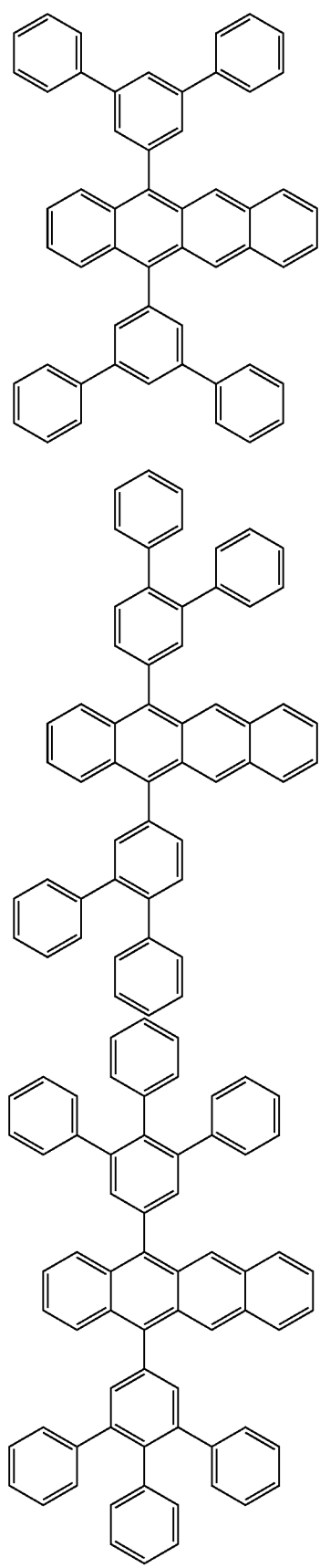
H1-9
H1-11
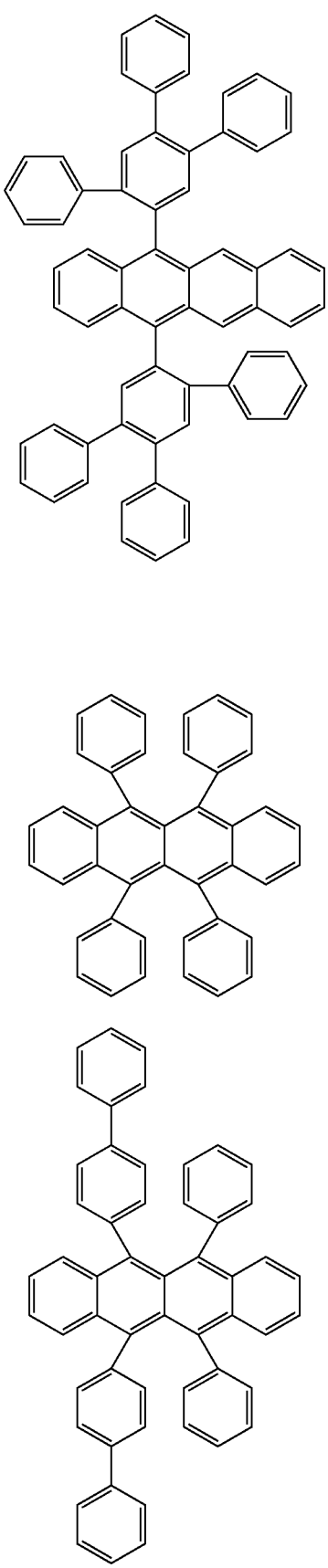
H1-12
H1-10
H1-13

H1-14
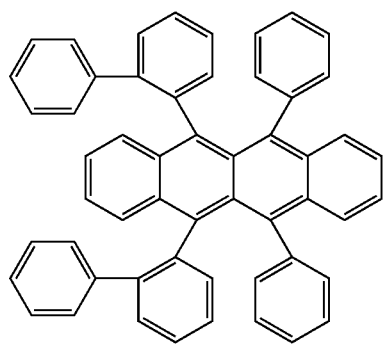
H1-15
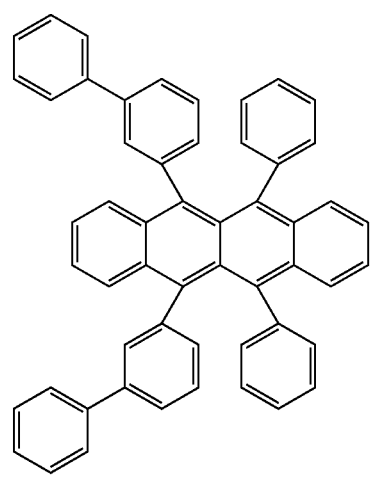
H1-16
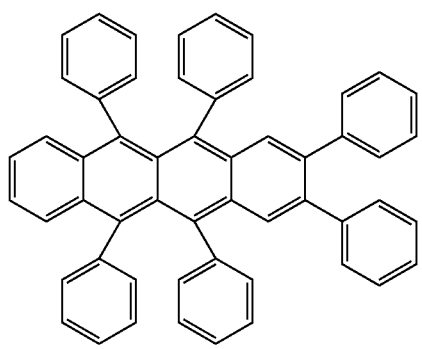
H1-17
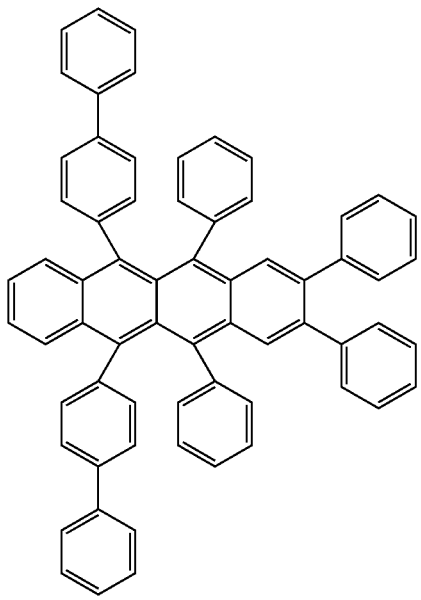
H1-18
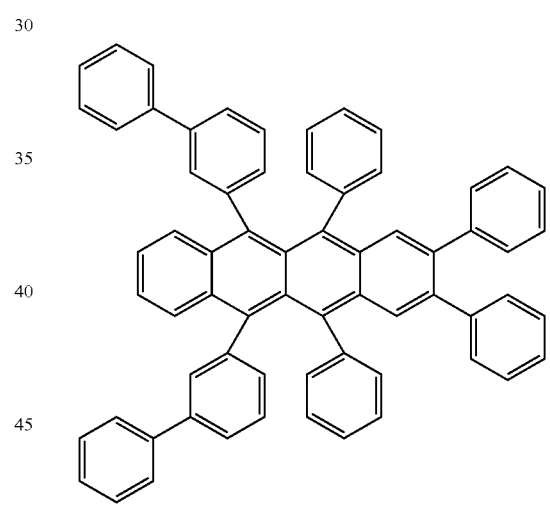
H1-19
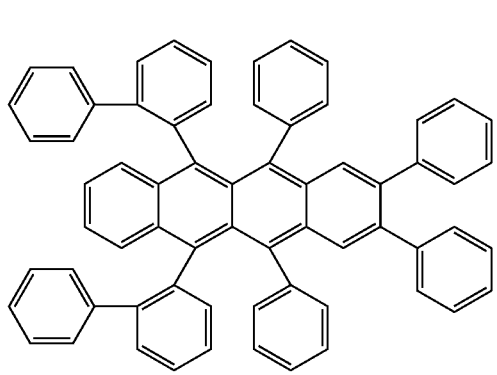

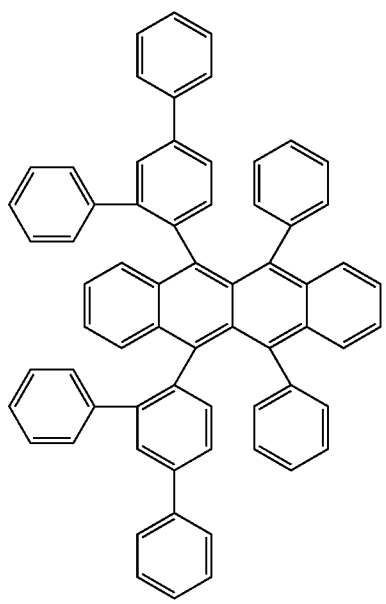
H1-20
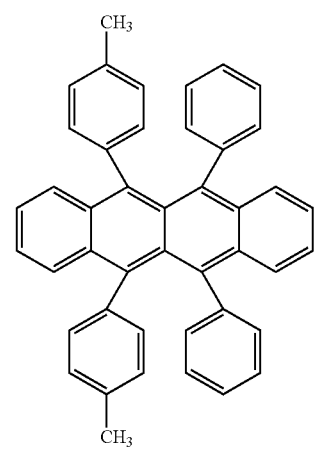
H1-21
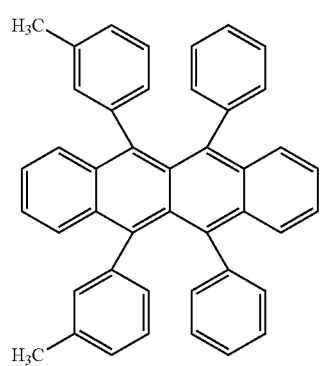
H1-22
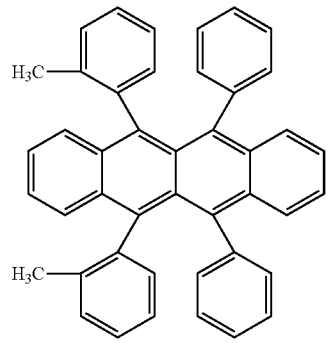
H1-23
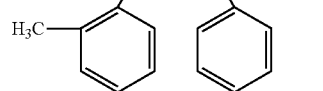
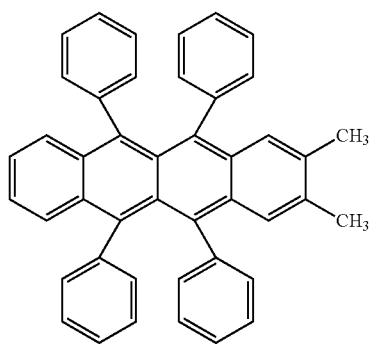
H1-24
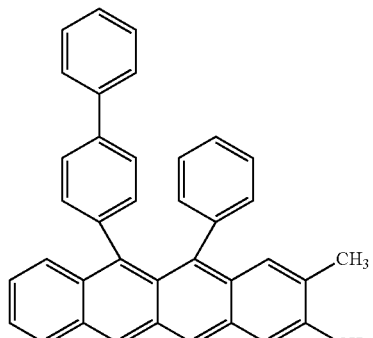
H1-25
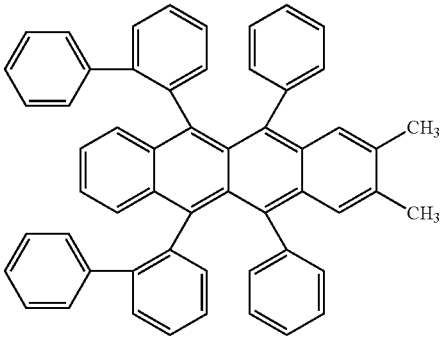
H1-26

-continued

H1-27

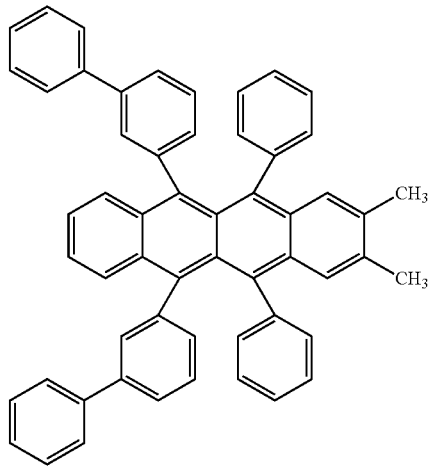

In the light-emitting layer 6A configured in this way, which contains a light-emitting material and a host material, the light-emitting material content (doping level) is preferably in a range of 0.01 wt % to 10 wt % and more preferably 0.1 wt % to 5 wt %. When the light-emitting material content is in any of these ranges, optimal light-emission efficiency is ensured.

The average thickness of the light-emitting layer 6A is not particularly limited; however, it is preferably on the order of 1 nm to 60 nm and more preferably on the order of 3 nm to 50 nm.

Electron Transport Layer

The electron transport layer 7 receives the electrons injected thereinto from the cathode 9 via the electron injection layer 8 and transmits them to the light-emitting layer 6A.

Examples of materials for the electron transport layer 7 (electron transport materials) are phenanthroline derivatives such as 2,9-dimethyl-4,7-diphenyl-1,10-phenanthroline (BCP), quinoline derivatives such as organometallic complexes coordinated by 8-quinolinol or its derivative ligands, e.g., tris(8-quinolinolato)aluminum (Alq$_3$), azaindolizine derivatives, oxadiazole derivatives, perylene derivatives, pyridine derivatives, pyrimidine derivatives, quinoxaline derivatives, diphenylquinone derivatives, nitro-substituted fluorene derivatives, and so forth, and these materials may be used singly or in combination of two or more kinds.

When two or more of such electron transport materials as listed above are used in combination, the electron transport layer 7 may be composed of a composite material containing two or more electron transport materials or be a laminate consisting of some layers made of different electron transport materials.

Preferably, the electron transport layer 7 contains an electron transport compound having an azaindolizine skeleton and an anthracene skeleton in the molecule (hereinafter, also simply referred to as an azaindolizine).

The use of an electron transport compound having an azaindolizine skeleton and an anthracene skeleton in the molecule in the electron transport layer 7, which is formed in contact with the light-emitting layer 6A, allows efficient transport of electrons from the electron transport layer 7 to the light-emitting layer 6A and thereby imparts excellent light emission efficiency to the light-emitting element 1A.

Furthermore, the efficient electron transport from the electron transport layer 7 to the light-emitting layer 6A lowers the driving voltage of the light-emitting element 1A and thereby extends the life of the light-emitting element 1A.

Moreover, compounds having an azaindolizine skeleton and an anthracene skeleton in the molecule are inert (highly resistant) to electrons and holes. This also helps extend the life of the light-emitting element 1A.

More preferably, the azaindolizine-based electron transport material used in the electron transport layer 7 contains one or two azaindolizine skeletons and one or two anthracene skeletons per molecule. This imparts excellent electron transport and electron injection properties to the electron transport layer 7.

Specific examples of preferred azaindolizines for use in the electron transport layer 7 include the compounds represented by formulae ELT-A1 to ELT-A24, the compounds represented by formulae ELT-B1 to ELT-B12, and the compounds represented by formulae ELT-C1 to ELT-C20.

ETL-A1

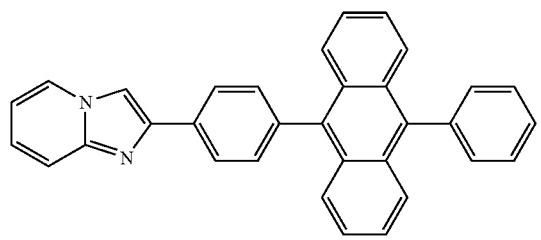

ETL-A2

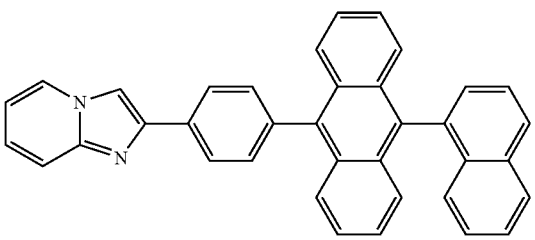

ETL-A3

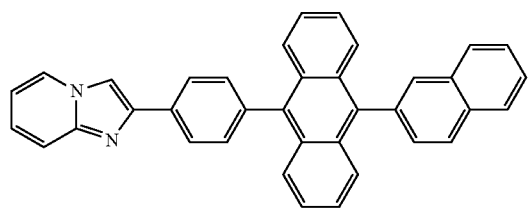

ETL-A4

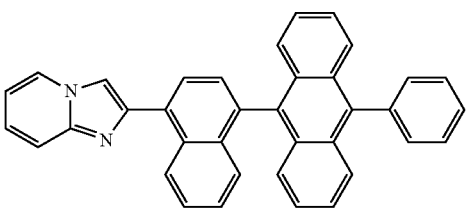

-continued
ETL-A5
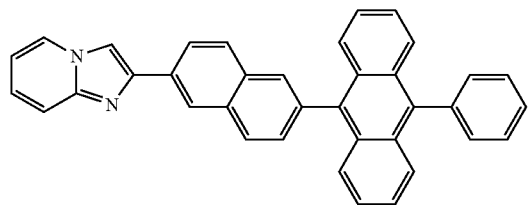
ETL-A6
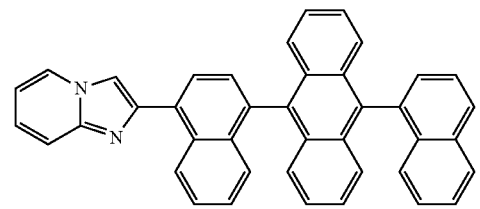
ETL-A7
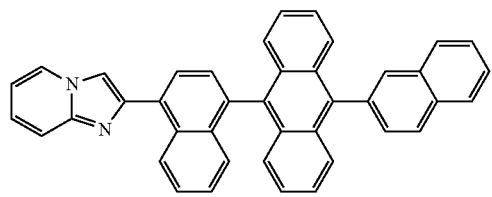
ETL-A8
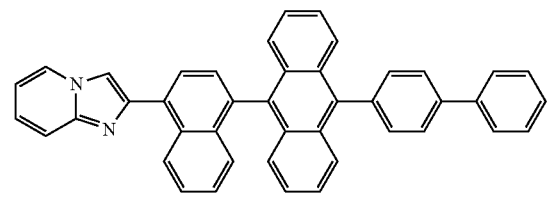
ETL-A9
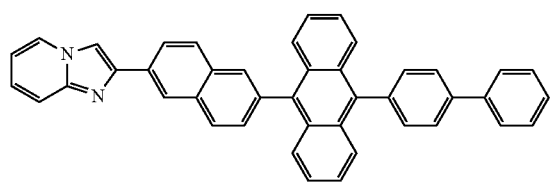
ETL-A10
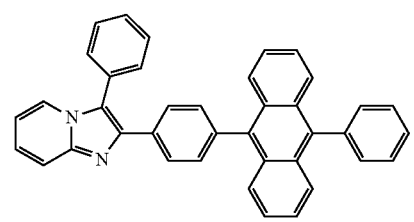
ETL-A11
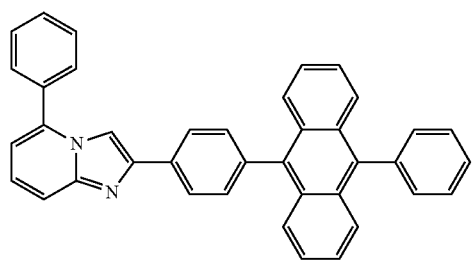
ETL-A12
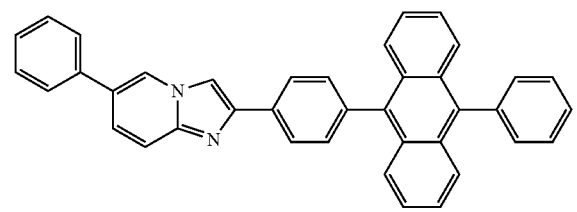
ETL-A13
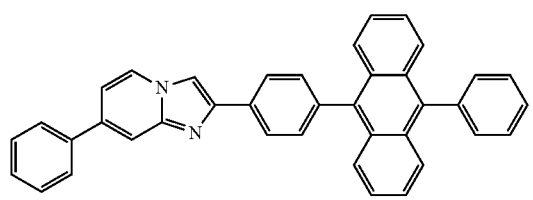
ETL-A14
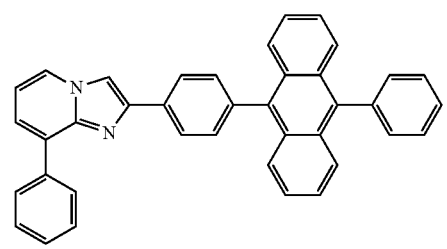
ETL-A15
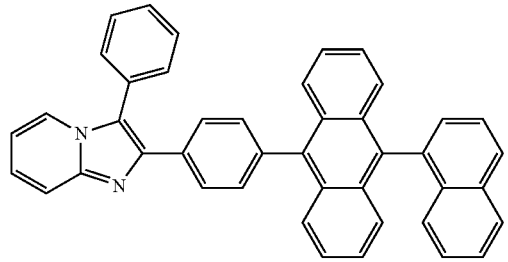
ETL-A16
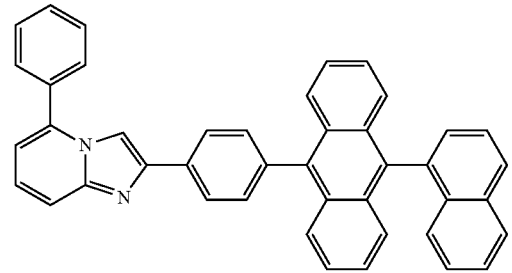

-continued
ETL-A17
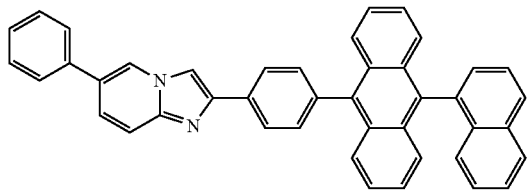
ETL-A18
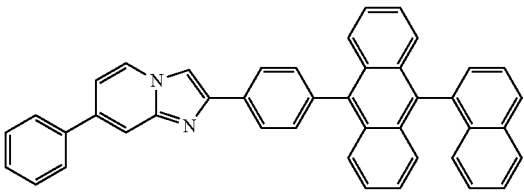
ETL-A19
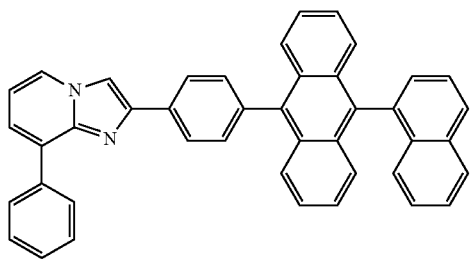
ETL-A20
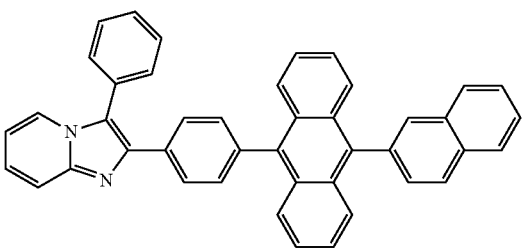
ETL-A21
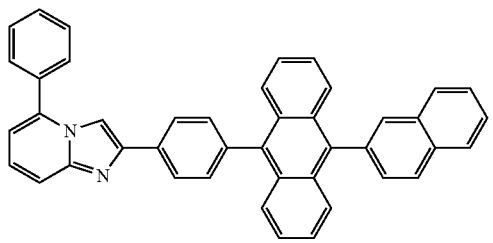
ETL-A22
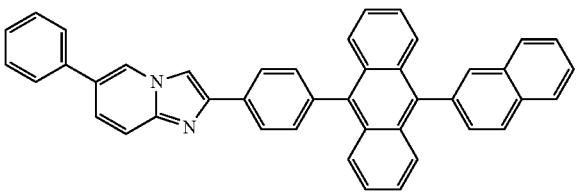
ETL-A23
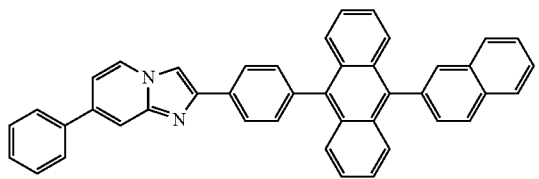
ETL-A24
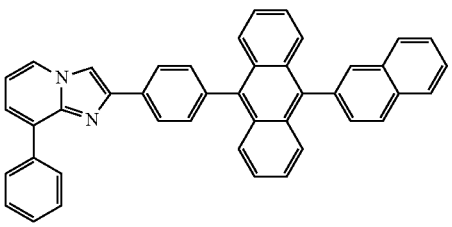
ETL-B1
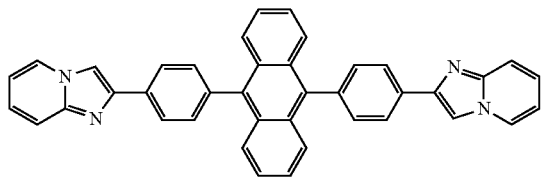
ETL-B2
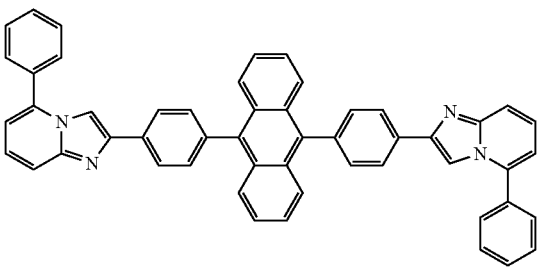
ETL-B3
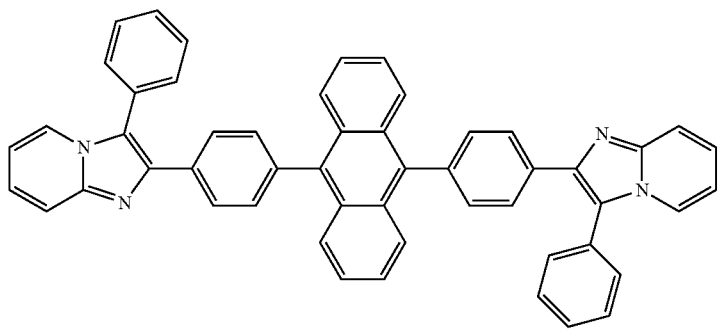

-continued
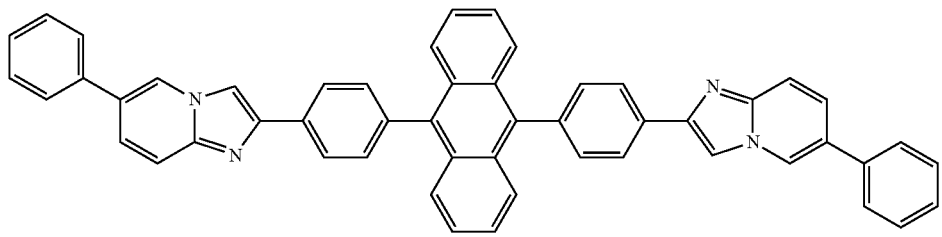
ETL-B4
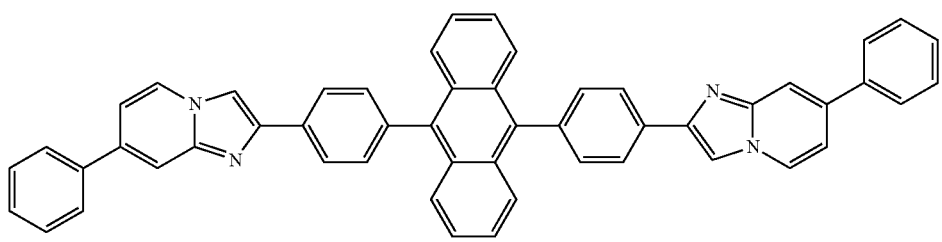
ETL-B5
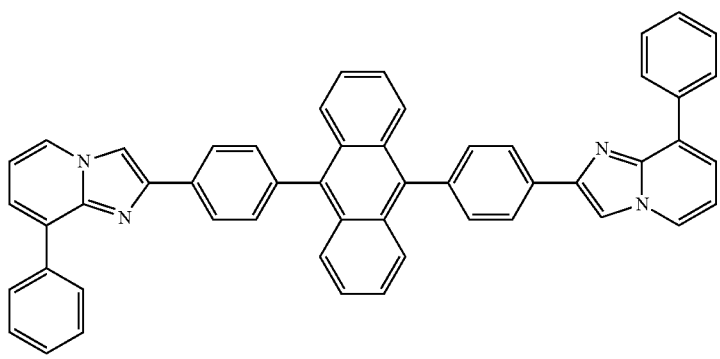
ETL-B6
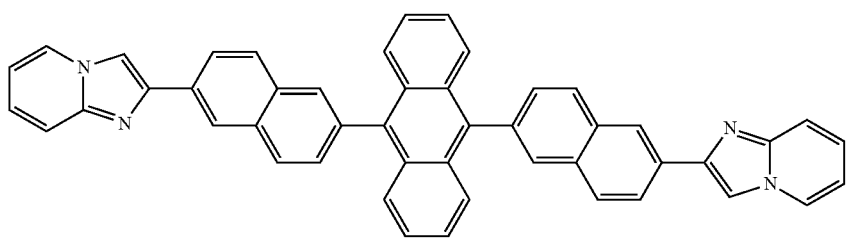
ETL-B7
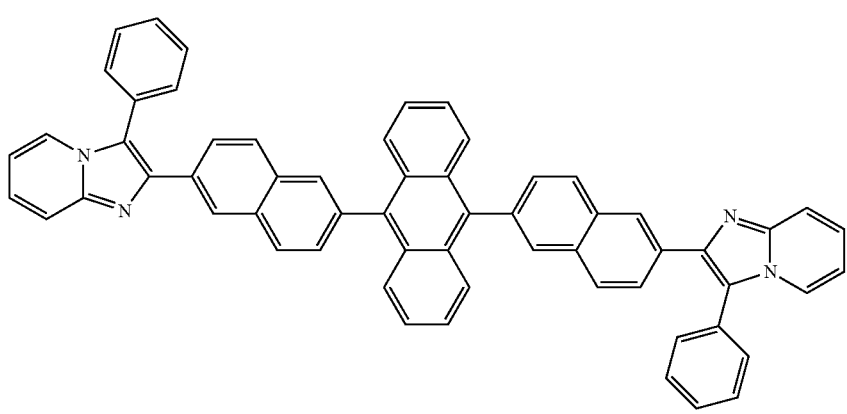
ETL-B8

-continued
ETL-B9
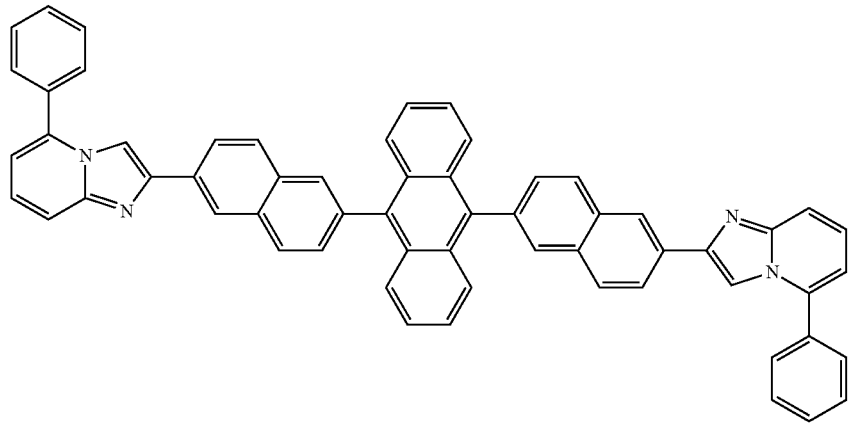
ETL-B10
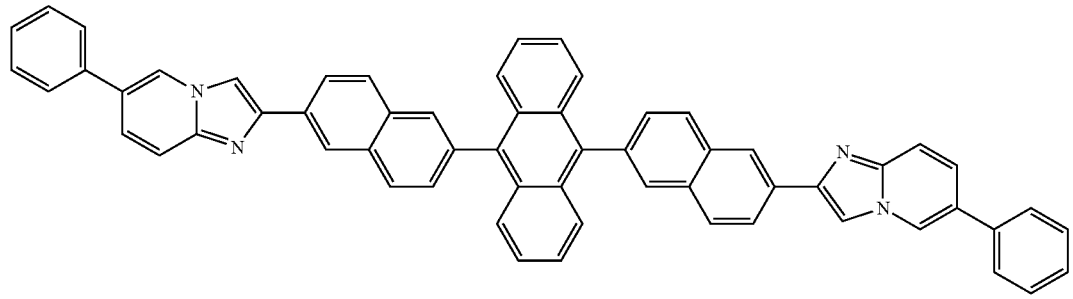
ETL-B11
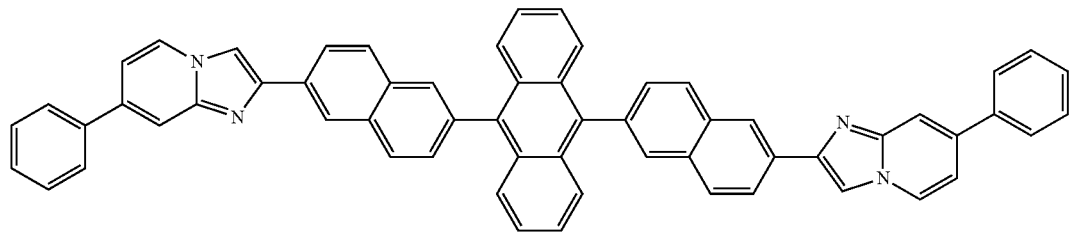
ETL-B12
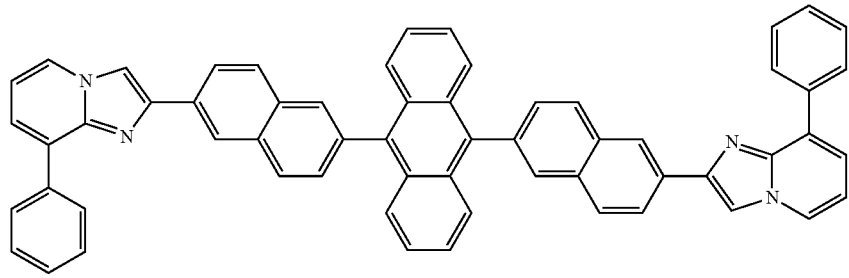
ETL-C1
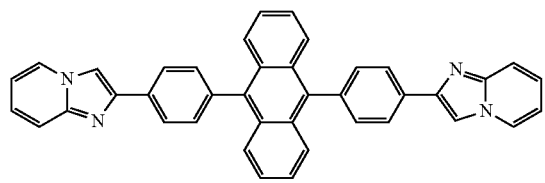
ETL-C2
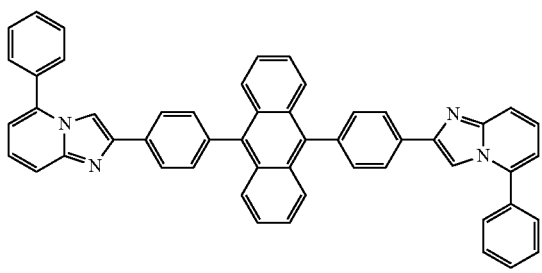

-continued
ETL-C3
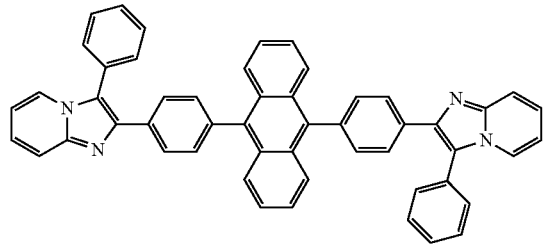
ETL-C4
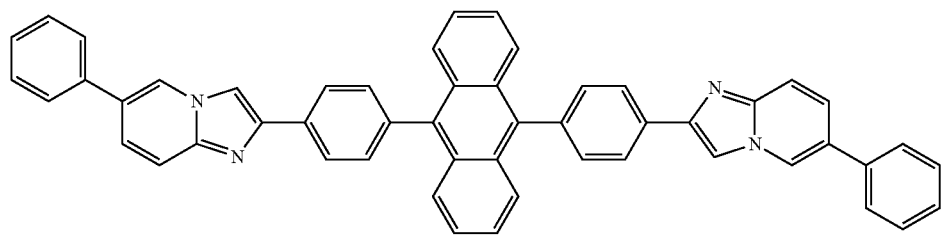
ETL-C5 ETL-C6
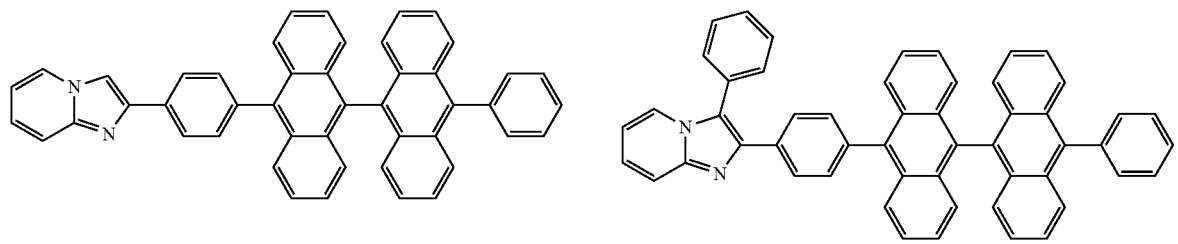
ETL-C7
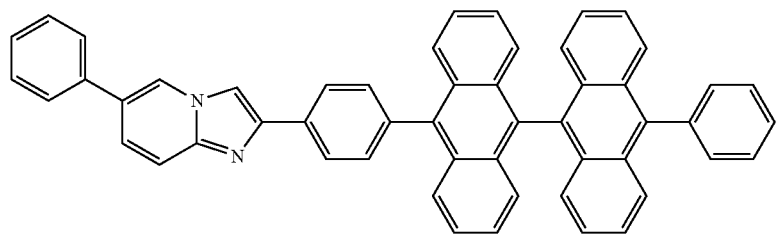
ETL-C8
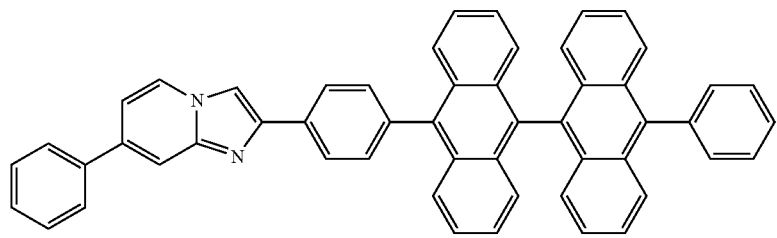
ETL-C9 ETL-C10
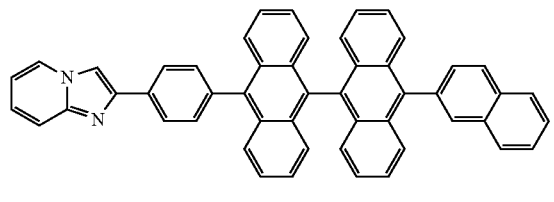 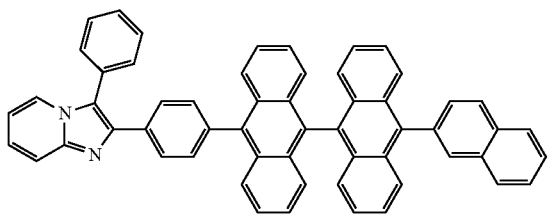

-continued
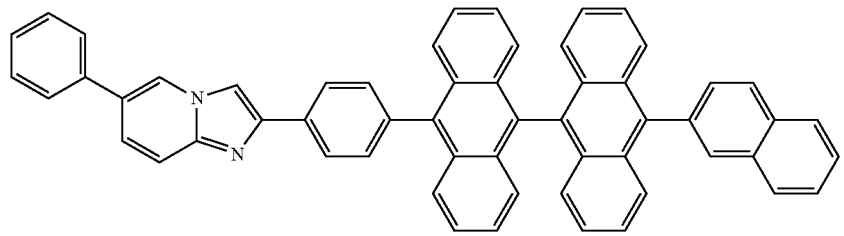
ETL-C11
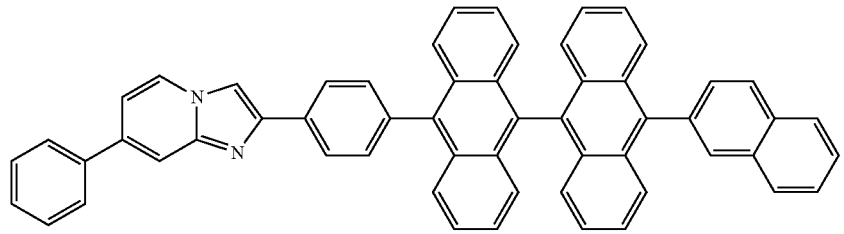
ETL-C12
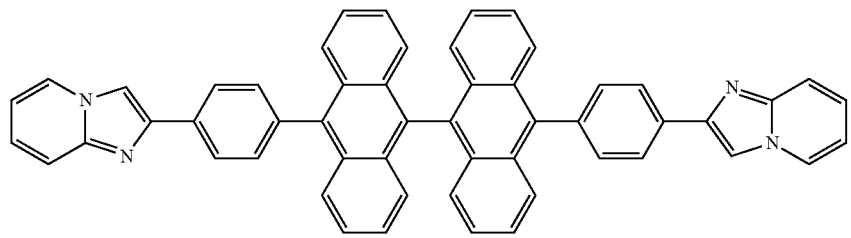
ETL-C13
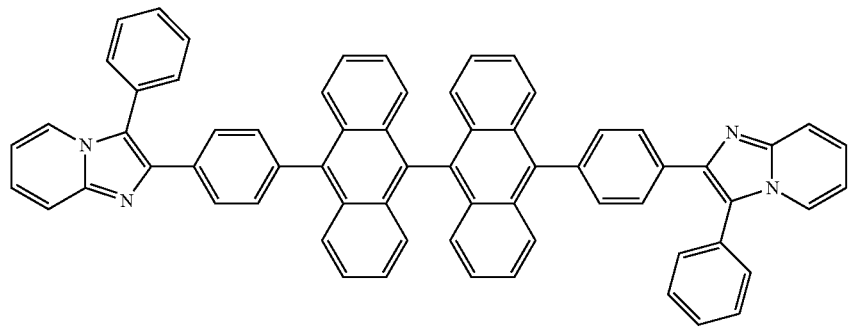
ETL-C14
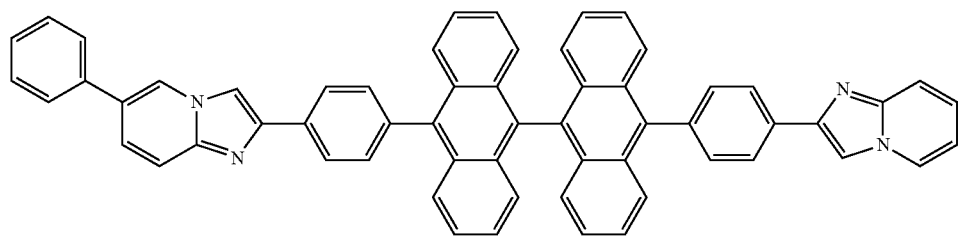
ETL-C15
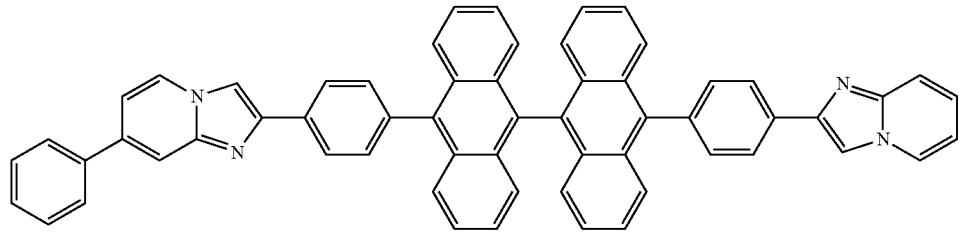
ETL-C16

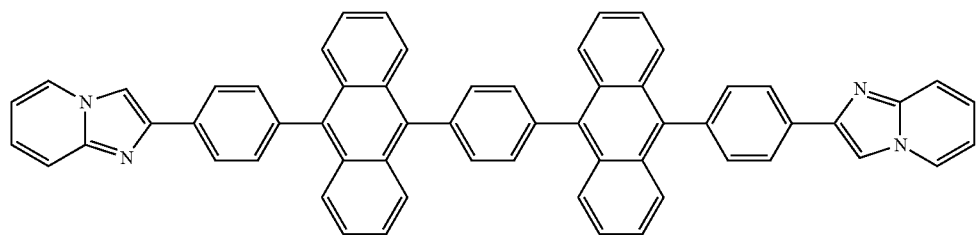

ETL-C17

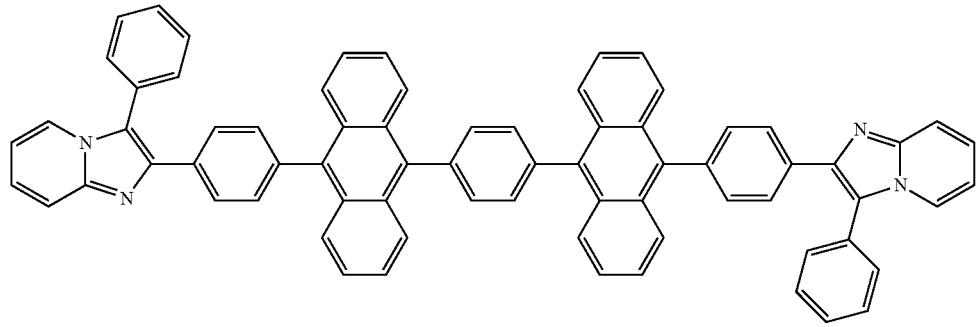

ETL-C18

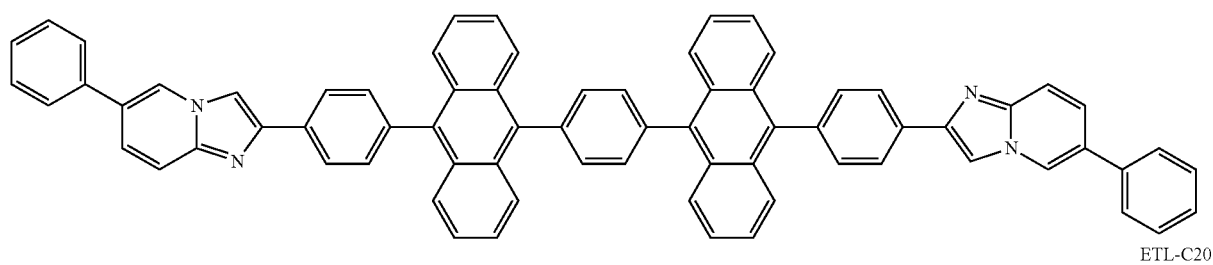

ETL-C19

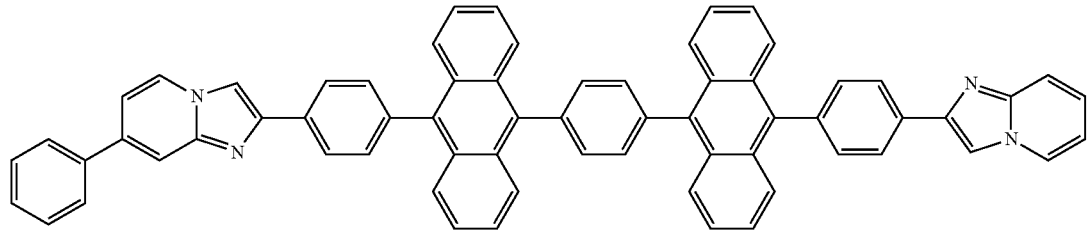

ETL-C20

The average thickness of the electron transport layer 7 is not particularly limited; however, it is preferably on the order of 1.0 nm to 200 nm and more preferably on the order of 10 nm to 100 nm.

Electron Injection Layer

The electron injection layer 8 improves the efficiency of the injection of electrons from the cathode 9.

Examples of materials for the electron injection layer 8 (electron injection materials) include various kinds of inorganic insulating and inorganic semiconductor materials.

Examples of appropriate inorganic insulating materials are alkali metal chalcogenides (oxides, sulfides, selenides, and tellurides), alkaline-earth metal chalcogenides, alkali metal halides, alkaline-earth metal halides, and so forth, and these materials may be used singly or in combination of two or more kinds. The electron injection layer 8 has its electron injection properties enhanced when it is mainly composed of one or more of these materials. In particular, alkali metal compounds (e.g., alkali metal chalcogenides and alkali metal halides) have very low work functions; the light-emitting element 1A can achieve high brightness when the electron transport layer 8 contains one or a combination of them.

Examples of appropriate alkali metal chalcogenides include $Li_2O$, $LiO$, $Na_2S$, $Na_2Se$, and $NaO$.

Examples of appropriate alkaline-earth metal chalcogenides include $CaO$, $BaO$, $SrO$, $BeO$, $BaS$, $MgO$, and $CaSe$.

Examples of appropriate alkali metal halides include $CsF$, $LIF$, $NaF$, $KF$, $LiCl$, $KCl$, and $NaCl$.

Examples of appropriate alkaline-earth metal halides include $CaF_2$, $BaF_2$, $SrF_2$, $MgF_2$, and $BeF_2$.

As for inorganic semiconductor materials, examples of appropriate ones are oxides, nitrides, oxynitrides, and other similar compounds containing at least one of the following elements: Li, Na, Ba, Ca, Sr, Yb, Al, Ga, In, Cd, Mg, Si, Ta, Sb, and Zn. These materials may be used singly or in combination of two or more kinds.

The average thickness of the electron injection layer 8 is not particularly limited; however, it is preferably on the order of 0.1 nm to 1000 nm, more preferably on the order of 0.2 nm to 100 nm, and even more preferably on the order of 0.2 nm to 50 nm.

Incidentally, this electron injection layer 8 may be omitted, depending on the composition, thickness, and other characteristics of the cathode 9 and the electron transport layer 7.

Sealing Member

The sealing member 10 is formed to cover the anode 3, the laminate 14, and the cathode 9 and air-tightly seals them to shut out oxygen and water. The sealing member 10 has several effects such as improved reliability and the prevention of alteration and deterioration (improved durability) of the light-emitting element 1A.

Examples of materials for the sealing member 10 include metals such as Al, Au, Cr, Nb, Ta, and Ti, alloys of these metals, silicon oxides, and various kinds of resin materials. When the sealing member 10 contains an electroconductive material, it is preferred that an insulating film is disposed between the sealing member 10 and the anode 3, the laminate 14, and the cathode 9 as needed for the prevention of short circuits.

In addition, the sealing member 10 may be a plate facing the substrate 2, provided that the space between them is sealed with a sealing material such as a thermosetting resin.

The light-emitting element 1A configured in this way, in which the light-emitting layer 6A contains a thiadiazole-based light-emitting material and a tetracene-based host material, can emit near-infrared light with improved efficiency for an extended period of time.

In the following, a typical procedure for preparing a light-emitting element 1A configured in this way is described.

I. First, a substrate 2 is prepared, and an anode 3 is formed over this substrate 2.

The anode 3 can be formed by various processes including chemical vapor deposition (CVD) processes such as plasma CVD and thermal CVD, dry plating processes such as vacuum deposition, wet plating processes such as electrolytic plating, thermal spraying processes, sol-gel processes, metal-organic deposition (MOD) processes, and metal foil cladding.

II. Then, a hole injection layer 4 is formed over the anode 3.

Examples of preferred processes for the formation of the hole injection layer 4 include CVD processes, dry plating processes such as vacuum deposition and sputtering, and other gas-phase processes.

Instead of using such processes, the hole injection layer 4 can be formed by dissolving the hole injection material or materials in a solvent or dispersing in a dispersion medium, applying the obtained hole injection layer base to the anode 3, and then drying the applied material (removing the solvent or dispersion medium).

Examples of appropriate methods for applying the hole injection layer base include various kinds of application methods such as spin coating, roll coating, and ink jet printing. By these application methods, the hole injection layer 4 can be formed relatively easily.

Examples of appropriate solvents and dispersing media for preparing the hole injection layer base include various kinds of inorganic and organic solvents and mixtures of them.

In addition, the drying operation can be performed in various ways including leaving the applied material at atmospheric pressure or a reduced pressure, heating, and spraying with an inert gas.

Incidentally, the anode 3 may be treated on its top surface with oxygen plasma prior to this step. This has several effects including imparting lyophilicity to the top surface of the anode 3, removing (washing away) adhesive organic matter from the top surface of the anode 3, and adjusting the work function of the superficial portion of the anode 3.

An example of preferred conditions of the oxygen plasma treatment is as follows: plasma power, approximately 100 W to 800 W; oxygen flow rate, approximately 50 mL/min to 100 mL/min; transport speed of the material under treatment (the anode 3), approximately 0.5 mm/sec to 10 mm/sec; temperature of the substrate 2, approximately 70° C. to 90° C.

III. Then, a hole transport layer 5 is formed over the hole injection layer 4.

Examples of preferred processes for the formation of the hole transport layer 5 include CVD processes, dry plating processes such as vacuum deposition and sputtering, and other gas-phase processes.

Instead of using such processes, the hole transport layer 5 can be formed by dissolving the hole transport material or materials in a solvent or dispersing in a dispersion medium, applying the obtained hole transport layer base to the hole injection layer 4, and then drying the applied material (removing the solvent or dispersion medium).

IV. Then, a light-emitting layer 6A is formed over the hole transport layer 5.

Examples of appropriate processes for the formation of the light-emitting layer 6A include dry plating processes such as sputtering and other gas-phase processes.

V. Then, an electron transport layer 7 is formed over the light-emitting layer 6A.

Examples of preferred processes for the formation of the electron transport layer 7 include dry plating processes such as sputtering and other gas-phase processes.

Instead of using such processes, the electron transport layer 7 can be formed by dissolving the electron transport material or materials in a solvent or dispersing in a dispersion medium, applying the obtained electron transport layer base to the light-emitting layer 6A, and then drying the applied material (removing the solvent or dispersion medium).

VI. Then, an electron injection layer 8 is formed over the electron transport layer 7.

When the electron injection layer 8 contains an inorganic material, the electron injection layer 8 can be formed by gas-phase processes including CVD processes and dry plating processes such as vacuum deposition and sputtering, application and firing of ink based on inorganic fine particles, and other appropriate techniques.

VII. Then, a cathode 9 is formed over the electron injection layer 8.

The cathode 9 can be formed by various processes including vacuum deposition, sputtering, metal foil cladding, and application and firing of ink based on metal fine particles.

Through such operations as described above, the light-emitting element 1A is obtained.

Finally, a sealing member 10 is put on the obtained light-emitting element 1A to cover it, and then bonded to the substrate 2.

In the following, some specific examples of an aspect of the invention and comparative examples are described.

Preparation of a Thiadiazole
Synthesis Example A1, Synthesis of Compound D-1
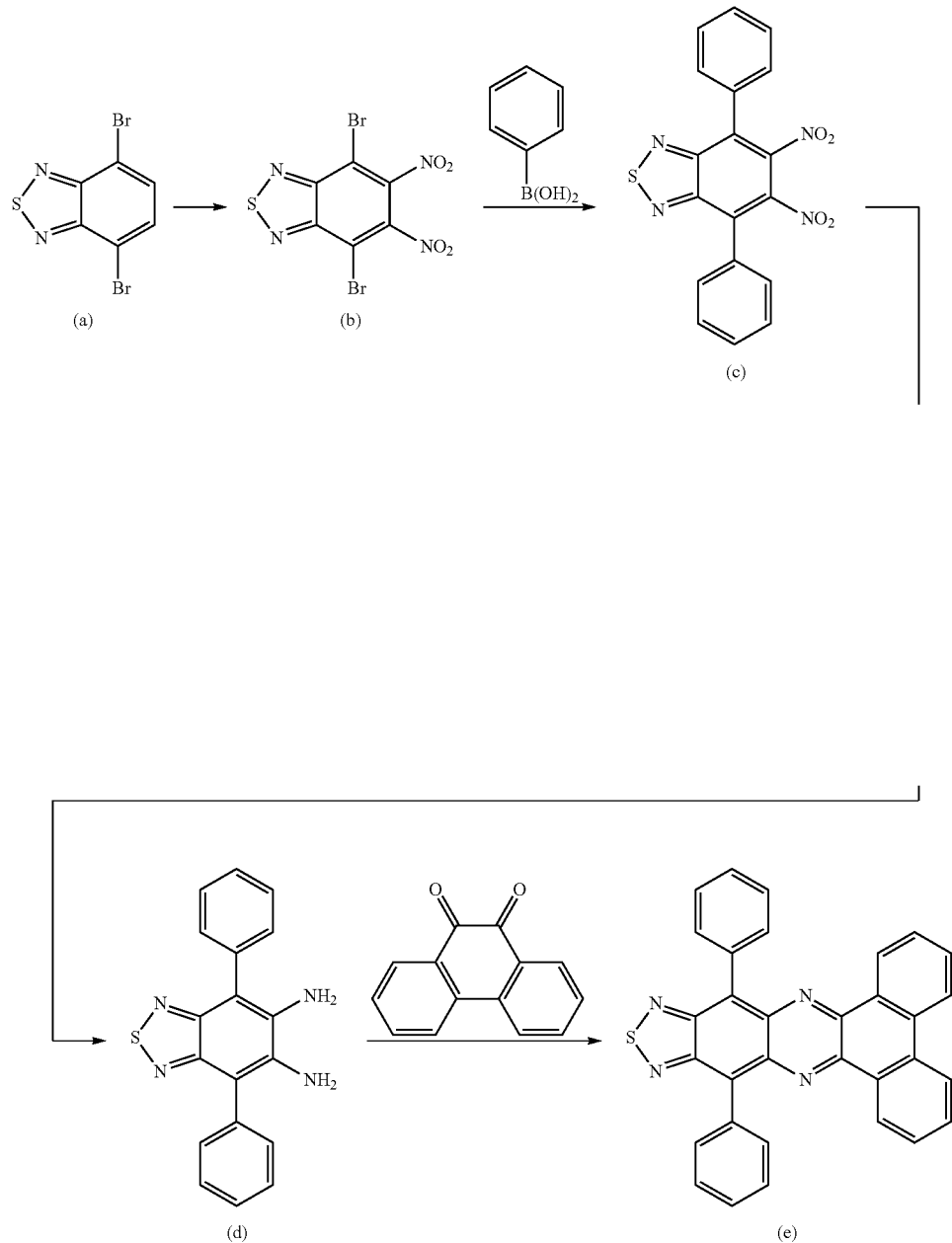

Synthesis Step A1-1

First, 1500 mL of fuming nitric acid was put into a 5-L flask and then cooled. To this flask, 1500 mL of sulfuric acid was added in several steps so that the temperature was maintained at 10° C. to 50° C. Subsequently, 150 g of compound (a), raw material dibromobenzothiadiazole, was added to the flask in small amounts over 1 hour. The temperature of the solution was maintained at not more than 5° C. during this operation. After all of compound (a) was added, the reaction was allowed to proceed at room temperature (25° C.) for 20 hours. After the completion of the reaction, the reaction solution was poured into 3 kg of ice and stirred overnight. Subsequently, the solution was filtered, and the residue was washed with methanol and heptane.

The residue was then dissolved in 200 mL of toluene by heating. The solution was allowed to cool to room temperature and then filtered. The residue was washed with a small amount of toluene and dried under reduced pressure.

In this way, 60 g of compound (b) (4,7-dibromo-5,6-dinitro-benzo[1,2,5]thiadiazole) was obtained with an HPLC purity of 95%.

Synthesis Step A1-2

In an Ar atmosphere, 30 g of the obtained dibromide (b), 23 g of phenylboronic acid (a commercially available product), 2500 mL of toluene, and a 2 M aqueous solution of cesium carbonate (152 g in 234 mL of distilled water) were put into a 5-L flask, and the reaction was allowed to proceed at 90° C. overnight. After the completion of the reaction, the solution was filtered and separated, and concentration was performed. The resulting crude product, which weighed 52 g, was separated using a silica gel column (5 kg of $SiO_2$), and a red-purple solid was collected.

In this way, 6 g of compound (c) (5,6-dinitro-4,7-diphenyl-benzo[1,2,5]thiadiazole) was obtained with an HPLC purity of 96%.

Synthesis Step A1-3

In an Ar atmosphere, the obtained dinitride (c), 6 g, as well as 7 g of reduced iron and 600 mL of acetic acid were put into a 1-L flask, the reaction was allowed to proceed at 80° C. for 4 hours, and the solution was allowed to cool to room temperature. After the completion of the reaction, the reaction solution was poured into 1.5 L of ion-exchanged water, and then 1.5 L of ethyl acetate was added to the solution. Since a precipitate immediately appeared, 1 L of tetrahydrofuran and 300 g of sodium chloride were added and the obtained solution was subjected to extraction and separated. The aqueous layer was subjected to another round of extraction with 1 L of tetrahydrofuran. The dry residue after evaporation was washed with small amounts of water and methanol, and an orange solid was collected.

In this way, 7 g of compound (d) (4,7-diphenyl-benzo[1,2,5]thiadiazole-5,6-diamine) was obtained with an HPLC purity of 80%.

Synthesis Step A1-4

In an Ar atmosphere, 4.5 g of the obtained diamine (d), 2.95 g of 9,10-phenanthrenequinone, and 300 mL of acetic acid as solvent were put into a 1-L flask, and the reaction was allowed to proceed at 80° C. for 2 hours. After the completion of the reaction, the solution was allowed to cool to room temperature and then poured into 1 L of ion-exchanged water. The resulting crystals were collected by filtration and washed with water, yielding a dark green solid weighing 7.2 g. This dark green solid was purified using a silica gel column (1 kg of $SiO_2$).

In this way, 4.5 g of compound (e) (the compound represented by formula D-1) was obtained with an HPLC purity of 99%. The obtained compound (e) was analyzed by mass spectrometry and found to have an $M^+$ of 490.

Furthermore, the obtained compound (e) was purified by sublimation at a set temperature of 340° C. The HPLC purity of the sublimation-purified compound (e) was 99%. Synthesis Example A2, synthesis of compound D-2

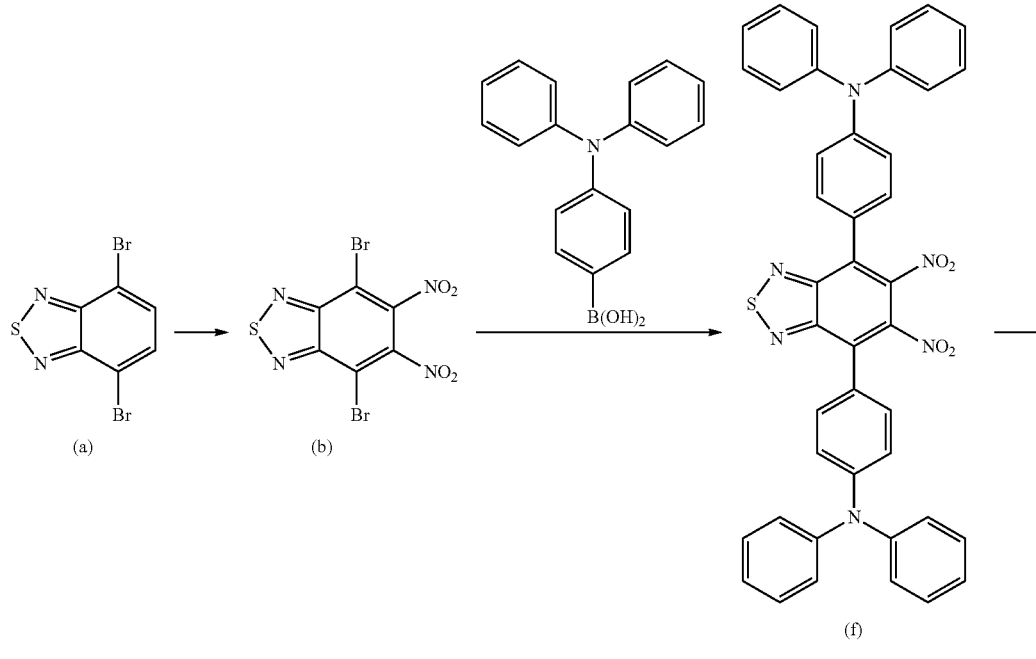

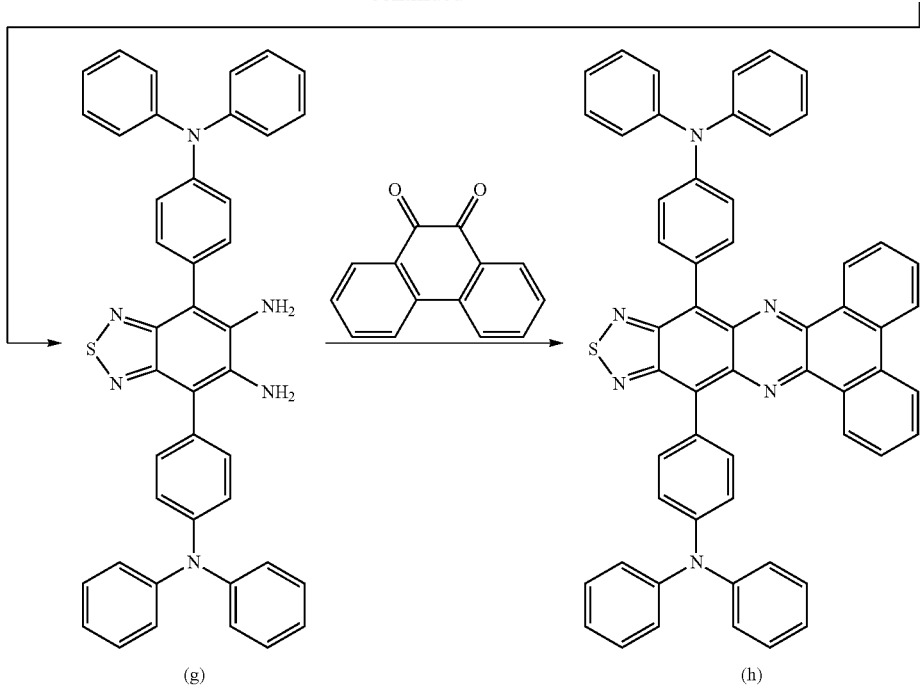

The same synthesis steps as in Synthesis Example A1 were repeated except phenylboronic acid, which was used in Synthesis Step A1-2 in Synthesis Example A1, was replaced with triphenylamine boronic acid. In this way, compound (h), i.e., the compound represented by formula D-2, was obtained.

The triphenylamine boronic acid used in this example was synthesized by the following procedure. In an Ar atmosphere, 246 g of 4-bromotriphenylamine (a commercially available product) and 1500 mL of anhydrous tetrahydrofuran were put into a 5-L flask, and then 570 mL of a 1.6 M n-BuLi solution in hexane was added dropwise at −60° C. over 3 hours. Thirty minutes later, 429 g of triisopropyl borate was added dropwise over 1 hour. Subsequently, the reaction was allowed to proceed overnight with no temperature control. After the completion of the reaction, 2 L of water was added dropwise, and the obtained solution was subjected to extraction with 2 L of toluene and separated. The isolated organic layer was concentrated, the residue was recrystallized, and the crystals were collected by filtration and dried. In this way, the intended boronic acid was obtained as a white solid weighing 160 g.

The HPLC purity of the obtained boronic acid was 99%.

The same procedure as Synthesis Step A1-2 in Synthesis Example A1 was repeated with the obtained boronic acid and thereby compound (f) was obtained.

The same procedure as Synthesis Step A1-3 in Synthesis Example A1 was repeated with the obtained compound (f) and thereby compound (g) was obtained.

Then, the same procedure as Synthesis Step A1-4 in Synthesis Example A1 was repeated with the obtained compound (g) and thereby compound (h), i.e., the compound represented by formula D-2, was obtained.

Synthesis Example A3, Synthesis of Compound D-3

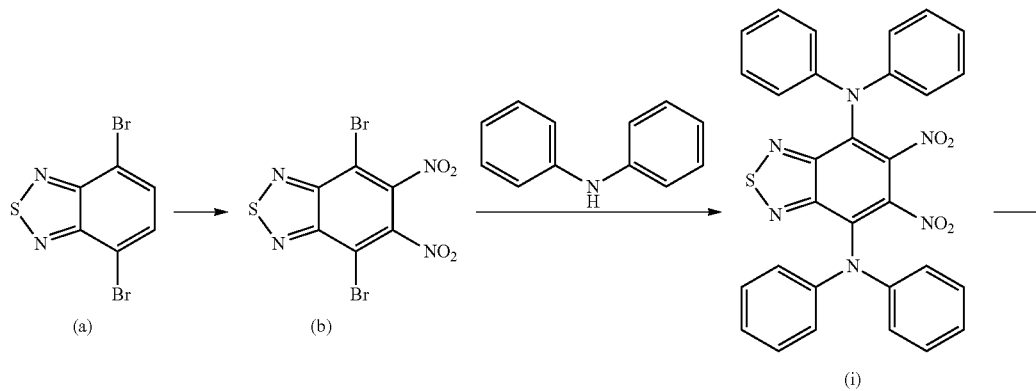

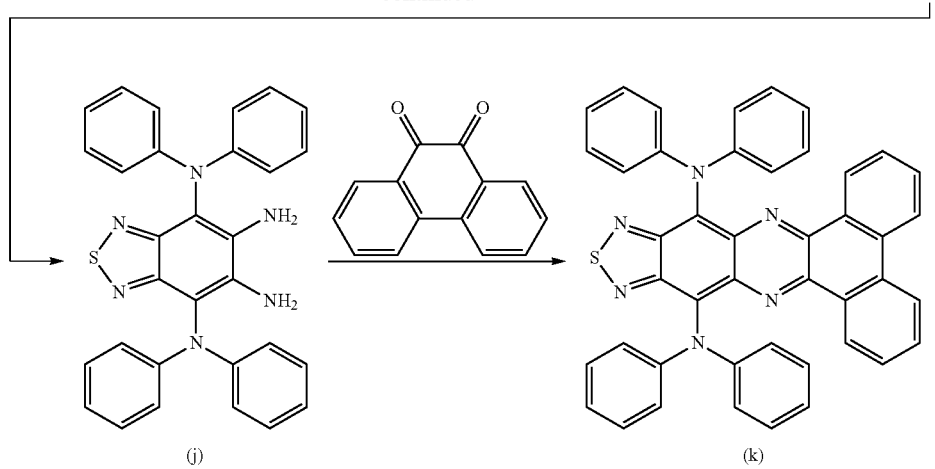

(j)                             (k)

The same synthesis steps as in Synthesis Example A1 were repeated except phenylboronic acid, which was used in Synthesis Step A1-2 in Synthesis Example A1, was replaced with diphenylamine. In this way, compound (k), i.e., the compound represented by formula D-3, was obtained.

More specifically, in this synthesis process diphenylamine was used in the following way. In an Ar atmosphere, 11 g of tetrakis(triphenyl) Pd (0) was put into a 300-mL flask and dissolved in 100 mL of toluene, and the resulting solution was warmed to 100° C. After 8 g of tri-t-butylphosphine was added to the flask, the reaction was allowed to proceed for 30 minutes. The obtained product was used as catalyst (Pd catalyst).

Separately, in an Ar atmosphere, 30 g of the dibromide (b) and 33 g of diphenylamine (a commercially available product) were put into a 5-L flask and dissolved in 2500 mL of toluene, and the resulting solution was warmed to 100° C. The Pd catalyst prepared in advance and 20 g of t-BuOK were added to the flask, and the resulting solution was heated to reflux for 3 hours.

After the reaction was complete and the solution was allowed to cool to room temperature, 100 mL of water was added, and the solution was stirred for approximately 1 hour. The solution was then transferred to a reparatory funnel, combined with an additional amount of water, and separated. The organic layer was collected and dried to a solid. The obtained solid was separated using a silica gel column (5 kg of $SiO_2$), a purple solid was collected.

In this way, 10 g of compound (i) (5,6-dinitro-N,N,N',N'-tetraphenyl-benzo[1,2,5]thiadiazole) was obtained with an HPLC purity of 96%.

The same procedure as Synthesis Step A1-3 in Synthesis Example A1 was repeated with the obtained compound (i) and thereby compound (j) was obtained.

Then, the same procedure as Synthesis Step A1-4 in Synthesis Example A1 was repeated with the obtained compound (j) and thereby compound (k), i.e., the compound represented by formula D-3, was obtained.

Preparation of a Host Material (a Tetracene-Based Material)

Synthesis Example B1, Synthesis of Compound H1-2

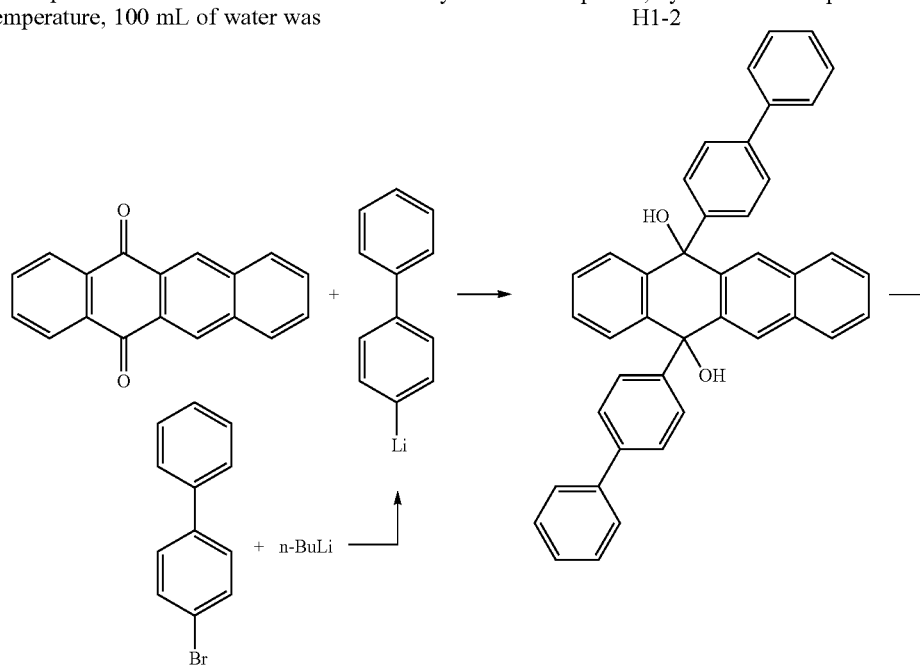

-continued

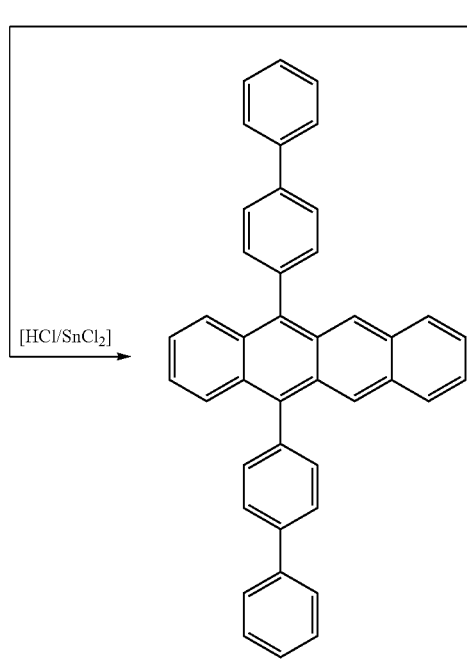

Synthesis Step B1-1

In an Ar atmosphere, 6 g of 4-bromobiphenyl and 50 mL of dry diethyl ether were put into a 300-mL flask. Then 14.5 mL of a 1.6 M n-BuLi solution in hexane was added dropwise at room temperature, and the reaction was allowed to proceed for 30 minutes.

Separately, in an Ar atmosphere, 2.7 g of 5,12-naphthacenequinone and 100 mL of dry toluene were put into a 500-mL flask. Lithium biphenyl, which was prepared in advance, was added dropwise to the flask, and the reaction was allowed to proceed for 3 hours. After the completion of the reaction, 20 mL of distilled water was added. The obtained solution was stirred for 30 minutes and then poured into methanol, and the resulting solid was isolated by filtration. The obtained solid was purified using silica gel (500 g of $SiO_2$).

In this way, a white solid weighing 4.5 g (5,12-bis(biphenyl-4-yl)-5,12-dihydronaphthacene-5,12-diol) was obtained.

Synthesis Step B1-2

The diol obtained in Synthesis Step B1-1, 4.5 g, and 300 mL of acetic acid were put into a 1000-mL flask. A solution of 5 g of tin chloride (II) (anhydrous) in 5 g of hydrochloric acid (35%) was added to the flask, and the mixed solution was stirred for 30 minutes. The solution was then transferred to a separatory funnel, toluene was added, the obtained solution was washed with distilled water by separation, and the residue was dried. The obtained solid was purified using silica gel (500 g of $SiO_2$), and thereby a yellow solid weighing 4 g (the compound represented by formula H1-2) was obtained.

Synthesis Example B2, Synthesis of Compound H1-5

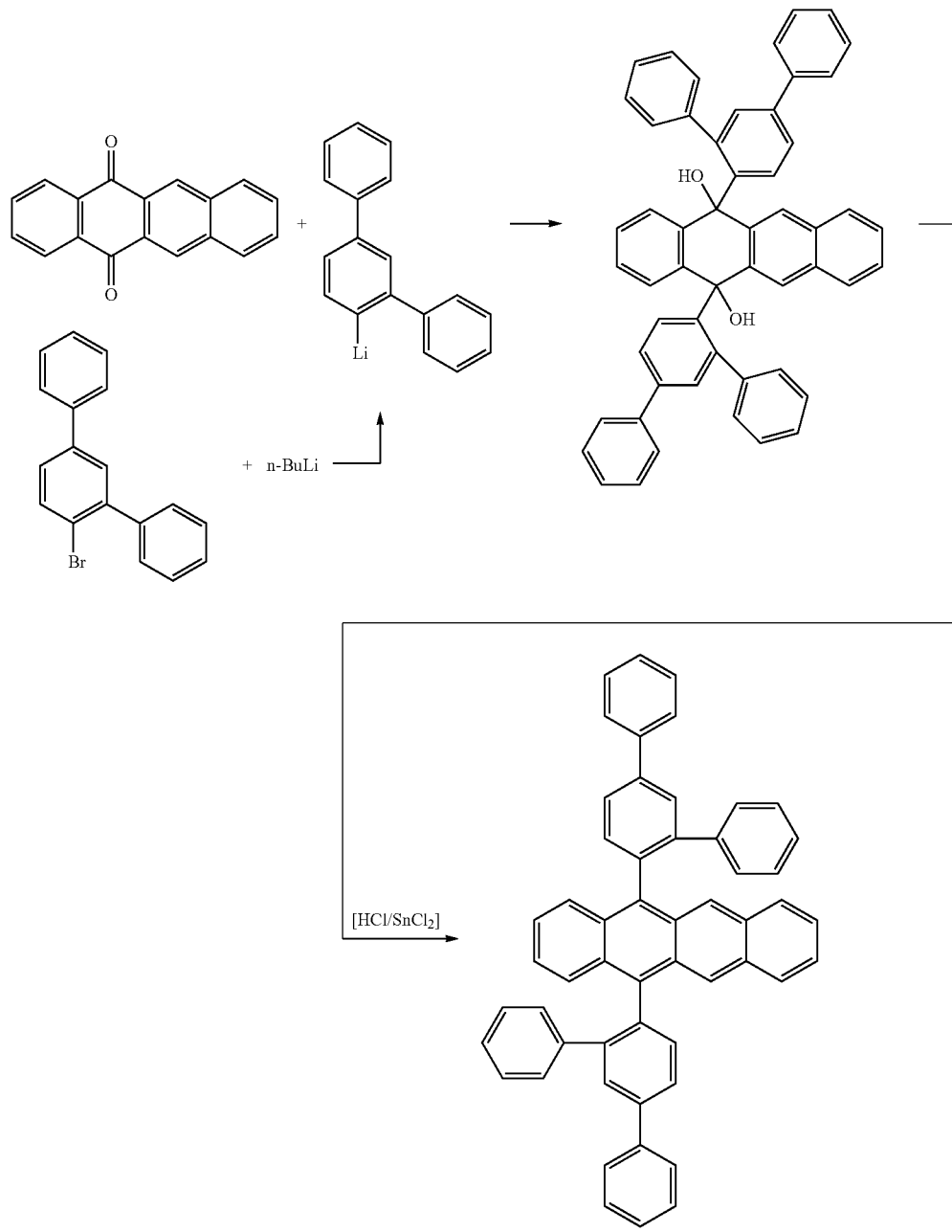

Synthesis Step E2-1

In an Ar atmosphere, 6 g of 4-bromo-[1,1';3',1"]terphenyl and 50 mL of dry diethyl ether were put into a 300-mL flask. Then 14.5 mL of a 1.6 M n-BuLi solution in hexane was added dropwise at room temperature, and the reaction was allowed to proceed for 30 minutes.

Separately, in an Ar atmosphere, 2 g of 5,12-naphthacene-quinone and 100 mL of dry toluene were put into a 500-mL flask. Lithium terphenyl, which was prepared in advance, was added dropwise to the flask, and the reaction was allowed to proceed for 3 hours. After the completion of the reaction, 20 mL of distilled water was added. The obtained solution was stirred for 30 minutes and then poured into methanol, and the resulting solid was isolated by filtration. The obtained solid was purified using silica gel (500 g of $SiO_2$).

In this way, a white solid weighing 5 g (5,12-bis([1,1';3',1"]terphenyl-4'-yl)-5,12-dihydronaphthacene-5,12-diol) was obtained.

Synthesis Step B2-2

The diol obtained in Synthesis Step B2-1, 5 g, and 300 mL of acetic acid were put into a 1000-mL flask. A solution of 5 g of tin chloride (II) (anhydrous) in 5 g of hydrochloric acid (35%) was added to the flask, and the mixed solution was stirred for 30 minutes. The solution was then transferred to a separatory funnel, toluene was added, the obtained solution was washed with distilled water by separation, and the residue was dried. The obtained solid was purified using silica gel (500 g of $SiO_2$), and thereby a yellow solid weighing 4.5 g (the compound represented by formula H1-5) was obtained.

Synthesis Example B3, Synthesis of Compound H1-13

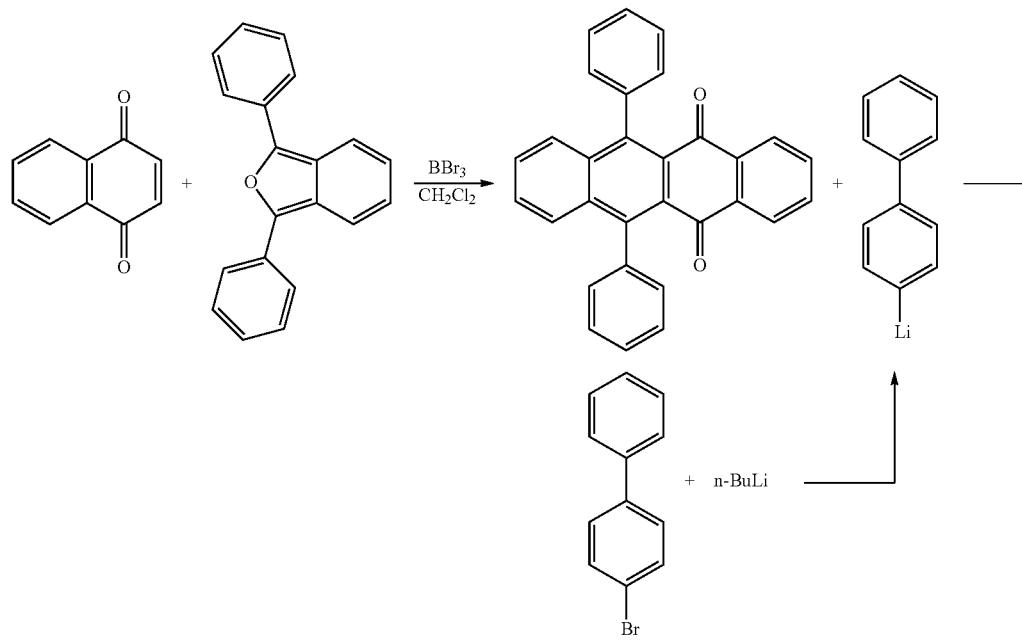

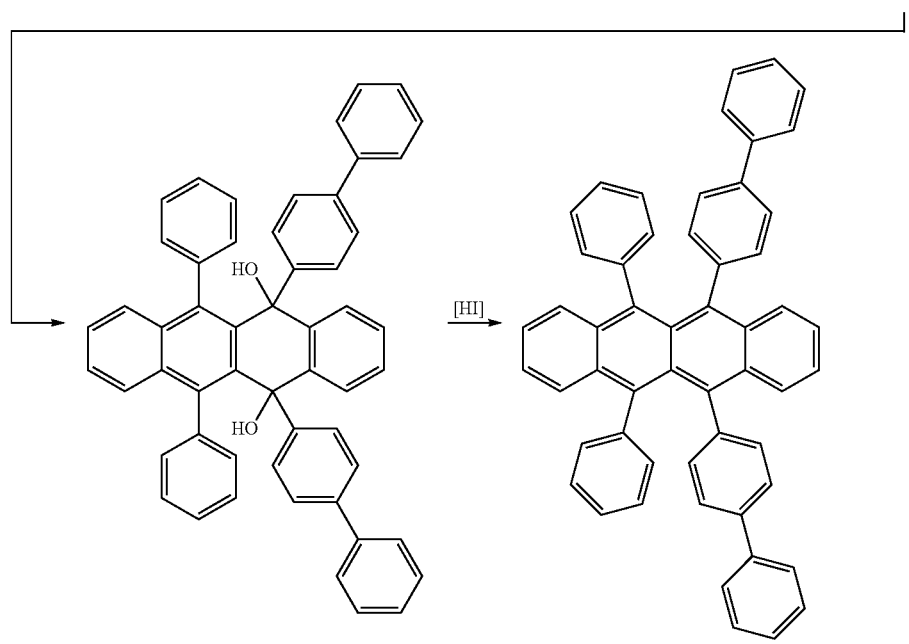

Synthesis Step B3-1

First, 100 mL of dichloromethane, 5.2 g of naphthoquinone, and 10 g of 1,3-diphenylisobenzofuran were put into a 500-mL flask, and the mixture was stirred for 1 hour. Subsequently, 33 mL of a commercially available boron tribromide (a 1 mol/L solution in dichloromethane) was added over 10 minutes, and thereby yellow needle crystals weighing 7.1 g (6,11-diphenyl-5,12-naphthacenequinone) were obtained.

Synthesis Step B3-2

In an Ar atmosphere, 6 g of 4-bromobiphenyl and 80 mL of dry diethyl ether were put into a 200-mL flask. Then 16 mL of a 1.6 M n-BuLi solution in hexane was added dropwise at room temperature, and the reaction was allowed to proceed for 30 minutes.

Separately, in an Ar atmosphere, 4.2 g of the quinone obtained in Synthesis Step B3-1 and 100 mL of dry toluene were put into a 500-mL flask. Lithium biphenyl, which was prepared in advance, was added dropwise to the flask, and the reaction was allowed to proceed for 3 hours. After the completion of the reaction, 20 mL of distilled water was added. The obtained solution was stirred for 30 minutes and then poured into methanol, and the resulting solid was isolated by filtration. The obtained solid was purified using silica gel (500 g of $SiO_2$).

In this way, a white solid weighing 5.5 g (5,12-bis(biphenyl-4-yl)-6,11-diphenyl-5,12-dihydronaphthacene-5,12-diol) was obtained.

Synthesis Step B3-3

Five grams of the diol obtained in Synthesis Step B3-2 and 200 mL of tetrahydrofuran were put into a 500-mL flask. Ten grams of hydroiodic acid (a 55% aqueous solution) was added to the flask, and the mixed solution was stirred for 2 hours with exclusion of light. The solution was then transferred to a separatory funnel, toluene was added, the obtained solution was washed with distilled water by separation, and the residue was dried. The obtained solid was purified using silica gel (500 g of $SiO_2$), and a red solid weighing 3 g (the compound represented by formula H1-13) was obtained.

Preparation of a Light-Emitting Element

Example 1

I. First, a transparent glass substrate having an average thickness of 0.5 mm was prepared. Subsequently, an ITO electrode (the anode) having an average thickness of 100 nm was formed over the substrate by sputtering.

The substrate was immersed in acetone and then in 2-propanol, cleaned by sonication, and subjected to oxygen plasma treatment and argon plasma treatment. Prior to each round of plasma treatment, the substrate was warmed to a temperature of 70° C. to 90° C. The conditions were common to both treatments and were as follows: plasma power, 100 W; gas flow rate, 20 sccm; treatment duration, 5 seconds.

II. Then, tetrakis(p-biphenylyl)benzidine, an amine-based hole transport material (the compound represented by formula HTL-1), was deposited over the ITO electrode by vacuum deposition to form a hole transport layer having an average thickness of 60 nm.

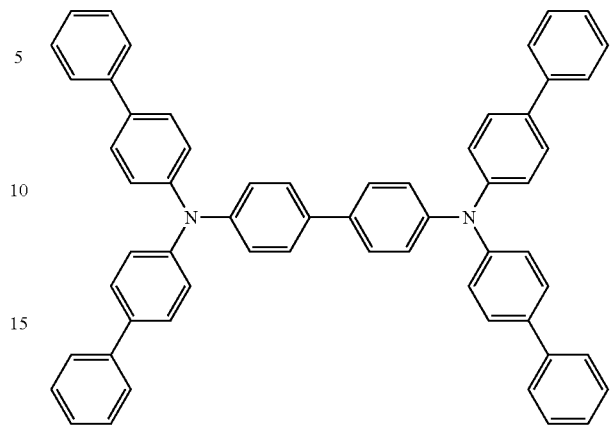

HTL-1

III. Then, a light-emitting layer having an average thickness of 25 nm was formed by depositing the constituent materials of the light-emitting layer over the hole transport layer by vacuum deposition. The constituent materials of the light-emitting layer were the compound represented by formula D-2 as light-emitting material (the guest material) and the compound represented by formula H1-2 as host material (a tetracene-based material). The light-emitting material content (doping level) of the light-emitting layer was 4.0 wt %.

IV. Then, 2,9-dimethyl-4,7-diphenyl-1,10-phenanthroline (BCP) was formed into a film on the light-emitting layer by vacuum deposition to provide an electron transport layer having an average thickness of 90 nm.

V. Then, lithium fluoride (LiF) was formed into a film on the electron transport layer by vacuum deposition to provide an electron injection layer having an average thickness of 1 nm.

VI. Then, Al was formed into a film on the electron injection layer by vacuum deposition to provide an Al cathode having an average thickness of 100 nm.

VII. Then, a protection cover made of glass (the sealing member) was placed on the obtained light-emitting element to cover the formed layers, and fixed and sealed with epoxy resin.

By these operations, a light-emitting element was prepared.

Example 2

A light-emitting element was prepared in the same way as in Example 1 except that the host material in the light-emitting layer was the compound represented by formula H1-5 (a tetracene-based material).

Example 3

A light-emitting element was prepared in the same way as in Example 1 except that the host material in the light-emitting layer was the compound represented by formula H1-13 (a tetracene-based material).

Example 4

A light-emitting element was prepared in the same way as in Example 1 except that the light-emitting material (dopant) content (doping level) of the light-emitting layer was 1.0 wt %.

Example 5

A light-emitting element was prepared in the same way as in Example 1 except that the light-emitting material (dopant) content (doping level) of the light-emitting layer was 2.0 wt %.

Example 6

A light-emitting element was prepared in the same way as in Example 1 except that the light-emitting material (dopant) content (doping level) of the light-emitting layer was 10.0 wt %.

Example 7

A light-emitting element was prepared in the same way as in Example 1 except that the average thickness of the light-emitting layer was 15 nm and the average thickness of the electron transport layer was 100 nm.

Example 8

A light-emitting element was prepared in the same way as in Example 1 except that the average thickness of the light-emitting layer was 50 nm and the average thickness of the electron transport layer was 65 nm.

Example 9

A light-emitting element was prepared in the same way as in Example 1 except that the average thickness of the light-emitting layer was 70 nm and the average thickness of the electron transport layer was 45 nm.

Example 10

A light-emitting element was prepared in the same way as in Example 1 except that the light-emitting material in the light-emitting layer was the compound represented by formula D-1.

Example 11

A light-emitting element was prepared in the same way as in Example 1 except that the light-emitting material in the light-emitting layer was the compound represented by formula D-3.

Example 12

A light-emitting element was prepared in the same way as in Example 1 except the following: the host material in the light-emitting layer was the compound represented by formula H1-5 (a tetracene-based material), the electron transport material in the electron transport layer was 2,9-dimethyl-4,7-diphenyl-1,10-phenanthroline (BOP), the average thickness of the light-emitting layer was 45 nm, and the average thickness of the electron transport layer was 70 nm.

Example 13

A light-emitting element was prepared in the same way as in Example 1 except the following: the host material in the light-emitting layer was the compound represented by formula H1-5 (a tetracene-based material), the electron transport material in the electron transport layer was 2,9-dimethyl-4,7-diphenyl-1,10-phenanthroline (BCP), the average thickness of the light-emitting layer was 15 nm, and the average thickness of the electron transport layer was 100 nm.

Example 14

A light-emitting element was prepared in the same way as in Example 1 except that the host material in the light-emitting layer was the compound represented by formula H1-5 (a tetracene-based material) and the electron transport layer was a laminate consisting of an $Alq_3$ layer and a BCP layer stacked in this order, each layer formed by vacuum deposition.

In the electron transport layer, the $Alq_3$ layer had an average thickness of 20 nm, and the BCP layer had an average thickness of 70 nm.

Example 15

A light-emitting element was prepared in the same way as in Example 1 except that the host material in the light-emitting layer was the compound represented by formula H1-5 (a tetracene-based material) and the electron transport layer was a laminate consisting of a layer of the compound represented by formula H1-5, an $Alq_3$ layer, and a BCP layer stacked in this order, each layer formed by vacuum deposition.

In the electron transport layer, the layer of the compound represented by formula H1-5 had an average thickness of 20 nm, the $Alq_3$ layer had an average thickness of 20 nm, and the BCP layer had an average thickness of 50 nm.

Example 16

A light-emitting element was prepared in the same way as in Example 1 except that the light-emitting material in the light-emitting layer was the compound represented by formula D-1 and the host material in the light-emitting layer was the compound represented by formula H1-5 (a tetracene-based material).

Example 17

A light-emitting element was prepared in the same way as in Example 1 except that the light-emitting material in the light-emitting layer was the compound represented by formula D-3 and the host material in the light-emitting layer was the compound represented by formula H1-5 (a tetracene-based material).

Comparative Example

A light-emitting element was prepared in the same way as in Example 1 except that the host material in the light-emitting layer was $Alq_3$.

Example 18

A light-emitting element was prepared in the same way as in Example 1 except that the host material in the light-emitting layer was $Alq_3$ and the electron transport material in the electron transport layer was the compound represented by formula ETL-A3, i.e., a compound having an azaindolizine skeleton and an anthracene skeleton in the molecule.

Example 19

A light-emitting element was prepared in the same way as in Example 1 except that the host material in the light-emitting layer was the compound represented by formula H1-5 (a tetracene-based material) and the electron transport material in the electron transport layer was the compound represented by formula ETL-A3.

Example 20

A light-emitting element was prepared in the same way as in Example 1 except that the host material in the light-emitting layer was the compound represented by formula H1-13 (a tetracene-based material) and the electron transport material in the electron transport layer was the compound represented by formula ETL-A3.

Example 21

A light-emitting element was prepared in the same way as in Example 1 except the following: the host material in the light-emitting layer was the compound represented by formula H1-5 (a tetracene-based material), the average thickness of the light-emitting layer was 45 nm, the electron transport material in the electron transport layer was the compound represented by formula ETL-A3, and the average thickness of the electron transport layer was 70 nm.

Example 22

A light-emitting element was prepared in the same way as in Example 1 except the following: the host material in the light-emitting layer was the compound represented by formula H1-5 (a tetracene-based material), the average thickness of the light-emitting layer was 15 nm, the electron transport material in the electron transport layer was the compound represented by formula ETL-A3, i.e., a compound having an azaindolizine skeleton and an anthracene skeleton in the molecule, and the average thickness of the electron transport layer was 100 nm.

Example 23

A light-emitting element was prepared in the same way as in Example 1 except that the host material in the light-emitting layer was the compound represented by formula H1-5 (a tetracene-based material) and the electron transport layer was a laminate consisting of an $Alq_3$ layer and a layer of the compound represented by formula ETL-A3 stacked in this order, each layer formed by vacuum deposition.

In the electron transport layer, the $Alq_3$ layer had an average thickness of 20 nm, and the layer of the compound represented by formula ETL-A3 had an average thickness of 70 nm.

Example 24

A light-emitting element was prepared in the same way as in Example 1 except that the host material in the light-emitting layer was the compound represented by formula H1-5 (a tetracene-based material) and the electron transport layer was a laminate consisting of a layer of the compound represented by formula H1-5, an $Alq_3$ layer, and a layer of the compound represented by formula ETL-A3 stacked in this order, each layer formed by vacuum deposition.

In the electron transport layer, the layer of the compound represented by formula H1-5 had an average thickness of 20 nm, the $Alq_3$ layer had an average thickness of 20 nm, and the layer of the compound represented by formula ETL-A3 had an average thickness of 50 nm.

Example 25

A light-emitting element was prepared in the same way as in Example 1 except the following: the light-emitting material in the light-emitting layer was the compound represented by formula D-1, the host material in the light-emitting layer was the compound represented by formula H1-5 (a tetracene-based material), and the electron transport material in the electron transport layer was the compound represented by formula ETL-A3.

Example 26

A light-emitting element was prepared in the same way as in Example 1 except the following: the light-emitting material in the light-emitting layer was the compound represented by formula D-3, the host material in the light-emitting layer was the compound represented by formula H1-5 (a tetracene-based material), and the electron transport material in the electron transport layer was the compound represented by formula ETL-A3.

Evaluation

A constant electric current of 100 mA/cm$^2$ was applied from a constant-current power supply (Keithley 2400, available from TOYO Corporation) to each of the light-emitting elements according to the above examples and comparative example, and the peak emission wavelength was measured using a miniature fiber optic spectrometer (S2000, available from Ocean Optics, Inc.). The emission power was measured using an optical power meter (8230 Optical Power Meter, available from ADC Corporation).

The voltage at the onset of light emission (driving voltage) was also measured.

Furthermore, the time for the luminance to decrease to 80% of the initial value ($LT_{80}$) was measured.

The test results are summarized in Tables 1 and 2.

TABLE 1

| | Light-emitting layer | | | | Electron transport layer | | Evaluations | | | |
|---|---|---|---|---|---|---|---|---|---|---|
| | | | Light-emitting material content (wt %) | Average thickness (nm) | | Average thickness (nm) | Peak emission wavelength (nm) | Emission power (mW/cm$^2$) | Voltage (V) | $LT_{80}$ (hr) |
| | Light-emitting material | Host material | | | Material | | | | | |
| Example 1 | D-2 | H1-2 | 4 | 25 | BCP | 90 | 840 | 1.4 | 7.4 | 100 |
| Example 2 | D-2 | H1-5 | 4 | 25 | BCP | 90 | 840 | 1.5 | 7.3 | 130 |
| Example 3 | D-2 | H1-13 | 4 | 25 | BCP | 90 | 840 | 1.6 | 7.5 | 90 |
| Example 4 | D-2 | H1-2 | 1 | 25 | BCP | 90 | 830 | 1.5 | 7.4 | 90 |

TABLE 1-continued

| | Light-emitting layer | | | | Electron transport layer | | Evaluations | | | |
|---|---|---|---|---|---|---|---|---|---|---|
| | Light-emitting material | Host material | Light-emitting material content (wt %) | Average thickness (nm) | Material | Average thickness (nm) | Peak emission wavelength (nm) | Emission power (mW/cm$^2$) | Voltage (V) | LT$_{80}$ (hr) |
| Example 5 | D-2 | H1-2 | 2 | 25 | BCP | 90 | 835 | 1.5 | 7.5 | 95 |
| Example 6 | D-2 | H1-2 | 10 | 25 | BCP | 90 | 845 | 1.1 | 7.7 | 95 |
| Example 7 | D-2 | H1-2 | 4 | 15 | BCP | 100 | 840 | 1.3 | 7.5 | 90 |
| Example 8 | D-2 | H1-2 | 4 | 50 | BCP | 65 | 840 | 1.4 | 7.8 | 120 |
| Example 9 | D-2 | H1-2 | 4 | 70 | BCP | 45 | 840 | 1.4 | 8.0 | 125 |
| Example 10 | D-1 | H1-2 | 4 | 25 | BCP | 90 | 830 | 1.5 | 7.5 | 120 |
| Example 11 | D-3 | H1-2 | 4 | 25 | BCP | 90 | 885 | 1.4 | 7.5 | 105 |
| Example 12 | D-2 | H1-5 | 4 | 45 | BCP | 70 | 840 | 1.5 | 7.1 | 135 |
| Example 13 | D-2 | H1-5 | 4 | 15 | BCP | 100 | 840 | 1.4 | 7.8 | 120 |
| Example 14 | D-2 | H1-5 | 4 | 25 | Alq$_3$ BCP | 20 70 | 840 | 1.5 | 7.7 | 145 |
| Example 15 | D-2 | H1-5 | 4 | 25 | H1-5 Alq$_3$ BCP | 20 20 50 | 840 | 1.5 | 7.8 | 135 |
| Example 16 | D-1 | H1-5 | 4 | 25 | BCP | 90 | 830 | 1.6 | 7.5 | 140 |
| Example 17 | D-3 | H1-5 | 4 | 25 | BCP | 90 | 885 | 1.4 | 7.5 | 135 |
| Comparative Example | D-2 | Alq$_3$ | 4 | 25 | BCP | 90 | 845 | 0.3 | 9.1 | 20 |

TABLE 2

| | Light-emitting layer | | | | Electron transport layer | | Evaluations | | | |
|---|---|---|---|---|---|---|---|---|---|---|
| | Light-emitting material | Host material | Light-emitting material content (wt %) | Average thickness (nm) | Material | Average thickness (nm) | Peak emission wavelength (nm) | Emission power (mW/cm$^2$) | Voltage (V) | LT$_{80}$ (hr) |
| Example 18 | D-2 | Alq$_3$ | 4 | 25 | ETL-A3 | 90 | 845 | 0.4 | 6.8 | >500 |
| Example 19 | D-2 | H1-5 | 4 | 25 | ETL-A3 | 90 | 840 | 1.6 | 5.0 | >1000 |
| Example 20 | D-2 | H1-13 | 4 | 25 | ETL-A3 | 90 | 840 | 1.7 | 5.1 | >1000 |
| Example 21 | D-2 | H1-5 | 4 | 45 | ETL-A3 | 70 | 840 | 1.7 | 5.2 | >1000 |
| Example 22 | D-2 | H1-5 | 4 | 15 | ETL-A3 | 100 | 840 | 1.5 | 4.8 | >1000 |
| Example 23 | D-2 | H1-5 | 4 | 25 | Alq$_3$ ETL-A3 | 20 70 | 840 | 1.6 | 5.2 | >1000 |
| Example 24 | D-2 | H1-5 | 4 | 25 | H1-5 Alq$_3$ ETL-A3 | 20 20 50 | 840 | 1.6 | 5.3 | >1000 |
| Example 25 | D-1 | H1-5 | 4 | 25 | ETL-A3 | 90 | 830 | 1.6 | 5.0 | >1000 |
| Example 26 | D-3 | H1-5 | 4 | 25 | ETL-A3 | 90 | 885 | 1.5 | 5.1 | >1000 |

As is clear from Tables 1 and 2, the light-emitting elements of Examples 1 to 26 emitted near-infrared light and were more intense than that of the Comparative Example in terms of emission power. Furthermore, the light-emitting elements of Examples 1 to 26 operated at lower voltages than that of the Comparative Example. These results indicate that the light-emitting elements of Examples 1 to 26 were of excellent light-emission efficiency.

Moreover, the light-emitting elements of Examples 1 to 26 were longer-lived than that of the Comparative Example.

In particular, as can be seen from Table 2, the light-emitting elements of Examples 18 to 26, the electron transport layer of which contained the compound represented by formula ETL-A3, i.e., a compound having an azaindolizine skeleton and an anthracene skeleton in the molecule, as electron transport material, operated at lower voltages and for longer periods of time not only than that of the Comparative Example but also than those of Examples 1 to 17.

Embodiment 2

Configuration of the Light-Emitting Element

Figure 2:
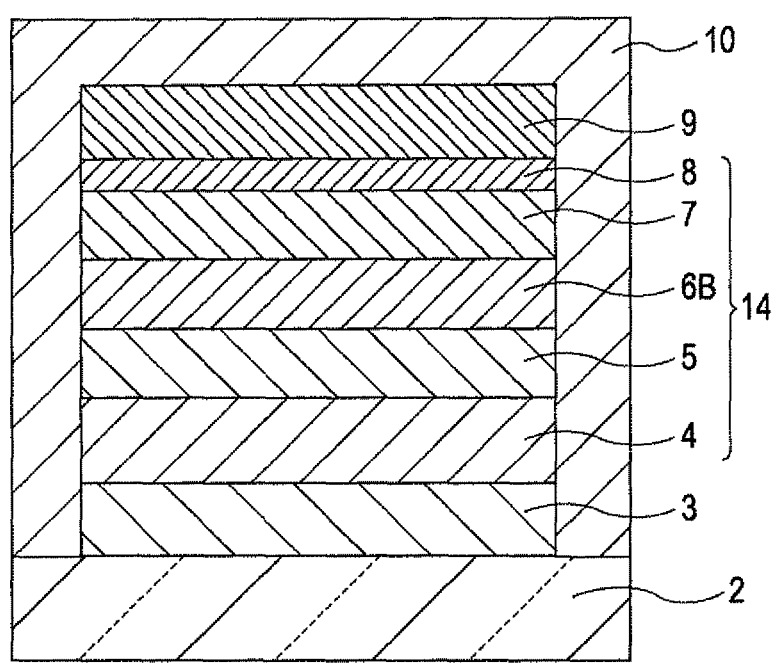
FIG. 2 schematically illustrates a cross-section of a light-emitting element according to Embodiment 2 of an aspect of the invention.

The following describes the light-emitting element according to Embodiment 2 with reference to FIG. 2. FIG. 2 schematically illustrates a light-emitting element according to Embodiment 2. The light-emitting element according to Embodiment 2 is different from the light-emitting element 1A according to Embodiment 1 only in the structure of the light-emitting layer. Thus, the components having the same functions as in Embodiment 1 are denoted with the same numerals in that embodiment and the detailed descriptions thereof are not repeated.

The light-emitting element (electroluminescence element) 1B illustrated in FIG. 2 has an anode 3, a hole injection layer 4, a hole transport layer 5, a light-emitting layer 6B, an electron transport layer 7, an electron injection layer 8, and a cathode 9 stacked in this order. In other words, the light-emitting element 1B has a laminate 14 disposed between the anode 3 and the cathode 9, and the laminate 14 contains the hole injection layer 4, the hole transport layer 5, the light-emitting layer 6B, the electron transport layer 7, and the electron injection layer 8 stacked in this order from the anode 3 side to the cathode 9 side.

The entire light-emitting element 1B is formed on a substrate 2 and sealed with a sealing member 10. The following describes this embodiment focusing on the differences from Embodiment 1.

Light-Emitting Layer

The light-emitting layer 6B emits light when electric current flows between the anode 3 and cathode 9.

For this purpose, the light-emitting layer 6B contains a light-emitting material.

More specifically, the light-emitting layer 6B contains a light-emitting material represented by formula (1) (also simply referred to as a thiadiazole).

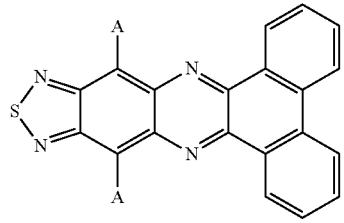

(1)

[In formula (1), each A independently represents a hydrogen atom, an alkyl group, a substituted or unsubstituted aryl group, a substituted or unsubstituted aryl amino group, or a substituted or unsubstituted triarylamine.]

This type of thiadiazole allows the light-emitting layer 65 to emit light in a wavelength range of not less than 700 nm (the near-infrared range).

Preferably, the light-emitting layer 6B contains a light-emitting material represented by any of formulae (2) to (4). Specific examples of particularly preferred compounds are those represented by formulae D-1 to D-3.

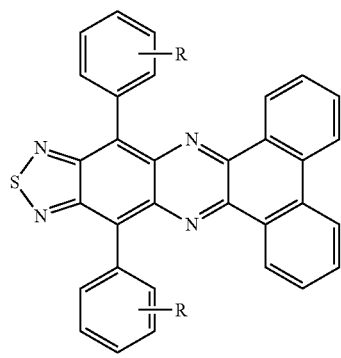

(2)

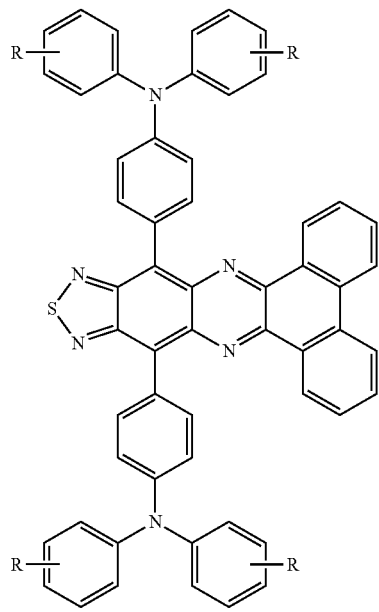

(3)

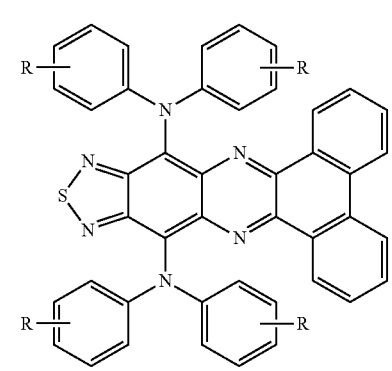

(4)

[In formulae (2) to (4), each R independently represents a hydrogen atom, an alkyl group, or a substituted or unsubstituted aryl group. There may be a ring formed by two adjacent carbon atoms that bond to each other.]

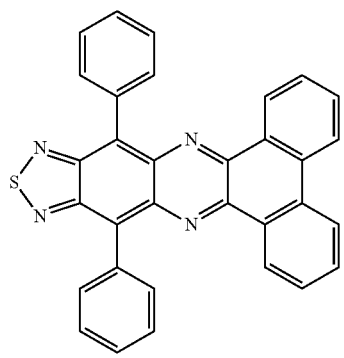

D-1

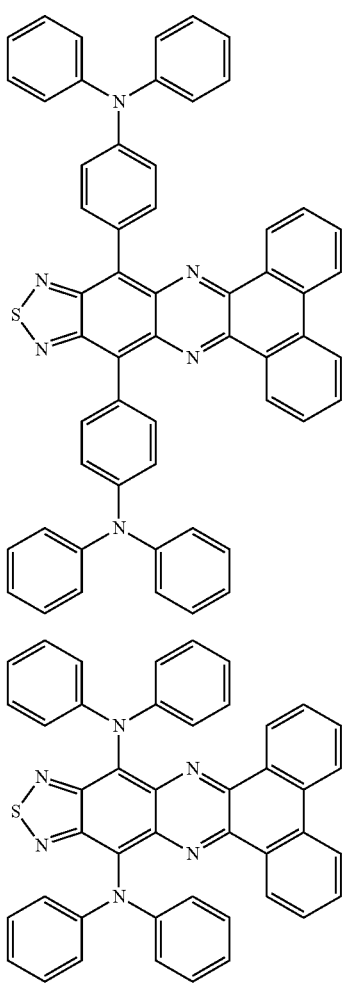

D-2

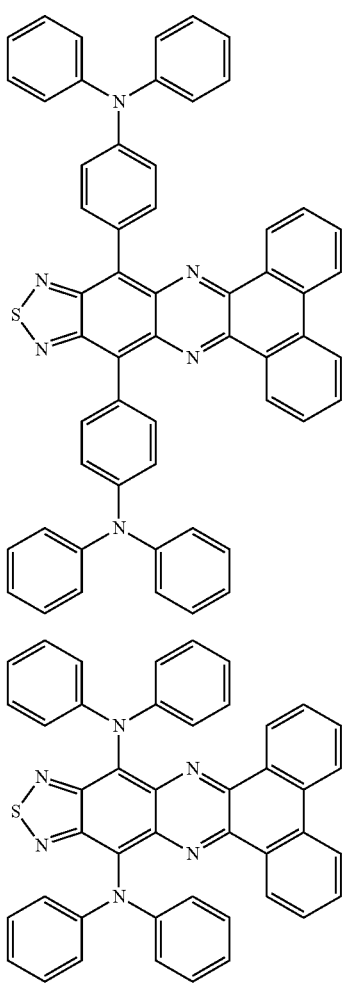

D-3

Incidentally, besides this light-emitting material, the light-emitting layer 6B may contain other light-emitting materials (e.g., fluorescent or phosphorescent materials).

The light-emitting layer 6B further contains, in addition to the light-emitting material described above, a host material that can be doped with (or can carry) this light-emitting material as guest material (dopant). This host material generates excitons from the injected holes and electrons and transfers the energy of the excitons to the light-emitting material (by Forster energy transfer or Dexter energy transfer) to excite the light-emitting material, thereby improving the light emission efficiency of the light-emitting element 1B. This type of host material can be used by, for example, doping the host material with its guest material, which is the light-emitting material in this case, as dopant.

An important thing here is that an anthracene-based material, which is classified into acene-based materials, is used as a host material for this purpose.

Acene-based materials are unlikely to undergo unwanted interactions with light-emitting materials of the above-mentioned types. Furthermore, the use of an acene-based host material (in particular, anthracene-based one) allows efficient energy transfer to the light-emitting material. Some possible reasons for this are the following: (a) energy transfer from the triplet excited state of the acene-based material induces the singlet excited state of the light-emitting material; (b) the overlap between the π electron cloud of the acene-based material and the electron cloud of the light-emitting material is large; and (c) the overlap between the emission spectrum of the acene-based material and the absorption spectrum of the light-emitting material is large.

For these and other reasons, the use of an acene-based host material improves the light emission efficiency of the light-emitting element 1B.

Furthermore, acene-based materials are highly resistant to electrons and holes and have excellent thermal stability, and these features of acene-based materials help extend the life of the light-emitting element 1B.

Additionally, when the light-emitting layer 63 is formed by a gas-phase deposition process, the excellent thermal stability of the acene-based host material protects the host material from decomposition by heat during the film formation process. This ensures the excellent film quality of the light-emitting layer 6B, which additionally helps enhance the light emission efficiency and extend the life of the light-emitting element 1B.

Moreover, acene-based materials are inherently unlikely to emit light, and this feature helps prevent the host material from affecting the emission spectrum of the light-emitting element 1B.

More specifically, the anthracene-based material is a compound represented by formula IRH-4 or its derivative. Preferably, it is a compound represented by any of formulae IRH-5 to IRH-8. This arrangement provides overvoltage protection during the continuous operation of the light-emitting element 1B while enhancing the light emission efficiency and extending the life of the light-emitting element 1B.

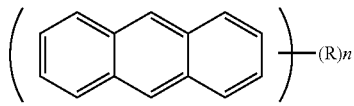

IRH-4

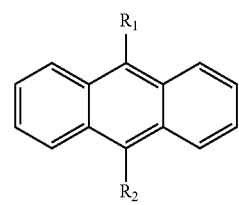

IRH-5

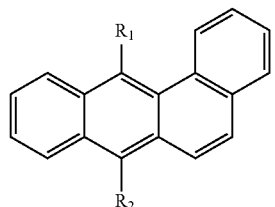

IRH-6

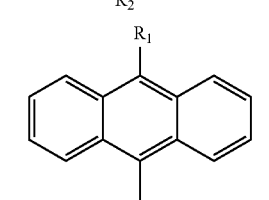

IRH-7

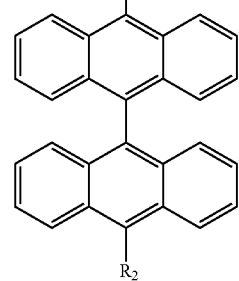

IRH-8

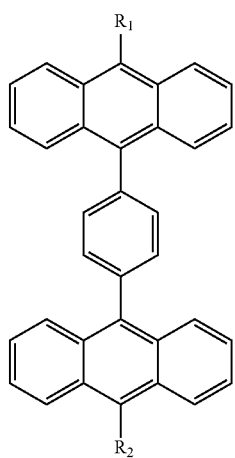

[In formula IRH-4, n represents a natural number of 1 to 10 and R represents a substituent or a functional group, and each R is independently a hydrogen atom, an alkyl group, a substituted or unsubstituted aryl group, or a substituted or unsubstituted aryl amino group. In formulas IRH-5 to IRH-8, each of $R_1$ and $R_2$ independently represents a hydrogen atom, an alkyl group, a substituted or unsubstituted aryl group, or a substituted or unsubstituted aryl amino group. $R_1$ and $R_2$ may be the same or different.]

It is also preferred that the anthracene-based material is composed of carbon atoms and hydrogen atoms. This more effectively prevents the host material and the light-emitting material from undergoing unwanted interactions and thereby further enhances the light emission efficiency of the light-emitting element 1B. Furthermore, the resistance of the host material to electrons and holes is further enhanced as well. As a result, the life of the light-emitting element 1B is further extended.

Specific examples of preferred anthracene-based materials include the compounds represented by formulae H2-1 to H2-16, the compounds represented by formulae H2-17 to H2-36, and the compounds represented by formula H2-37 to H2-56.

H2-1

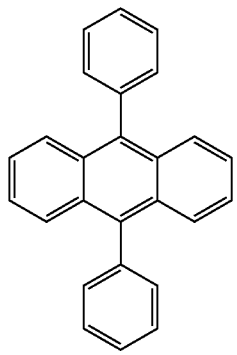

H2-2

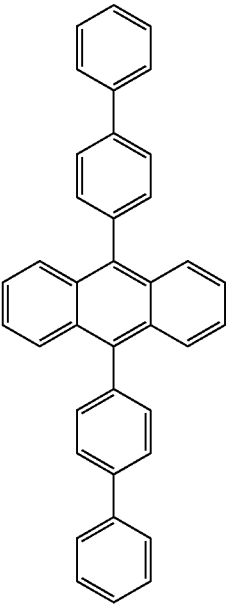

H2-3

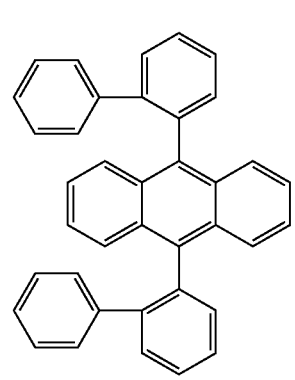

H2-4

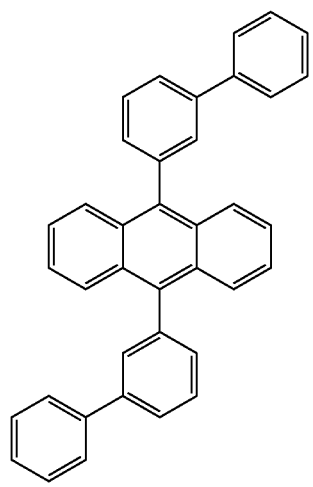

H2-5
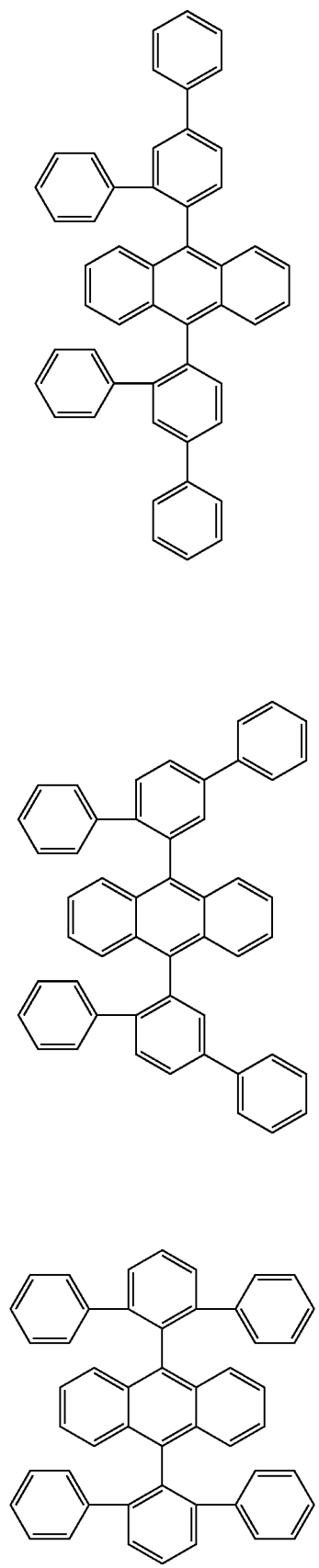
H2-6
H2-7
H2-8
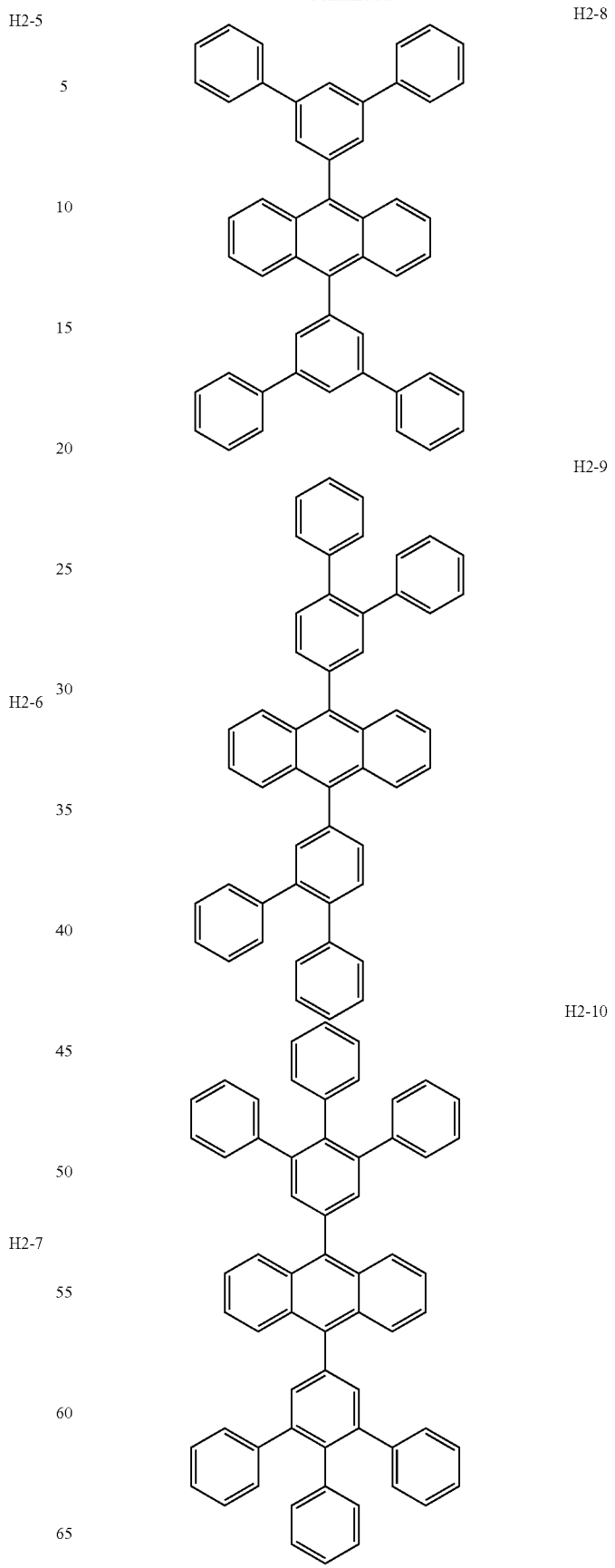
H2-9
H2-10

H2-11
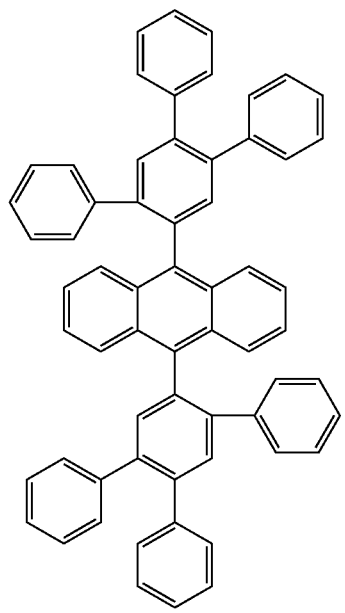
H2-12
H2-13
H2-14
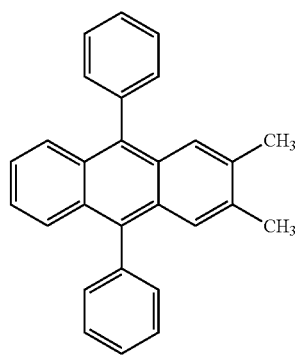
H2-15
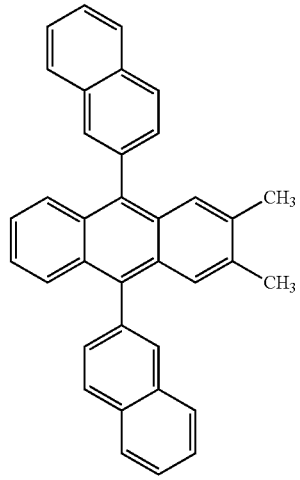
H2-16
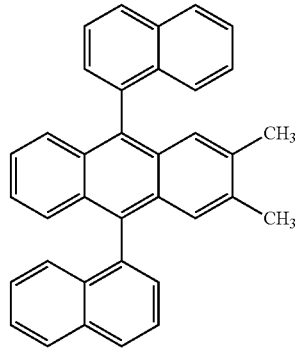
H2-17
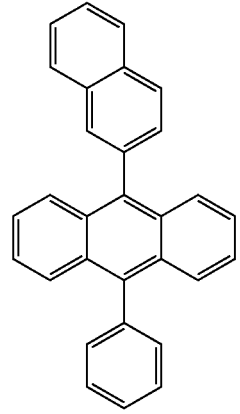

H2-18
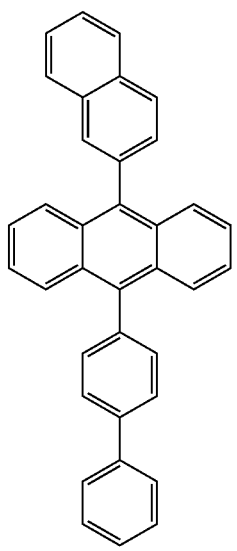
H2-19
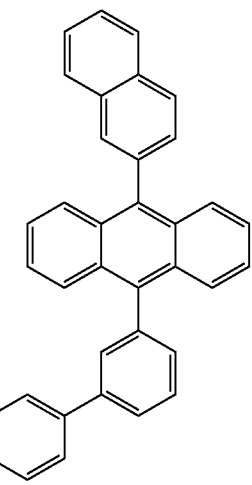
H2-20
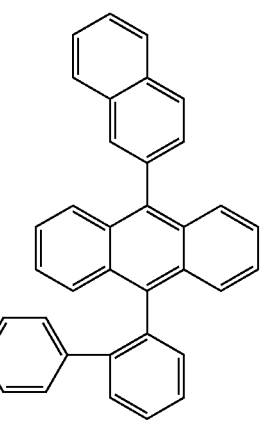
H2-21
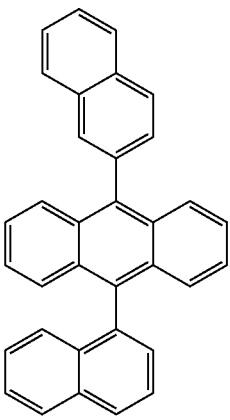
H2-22
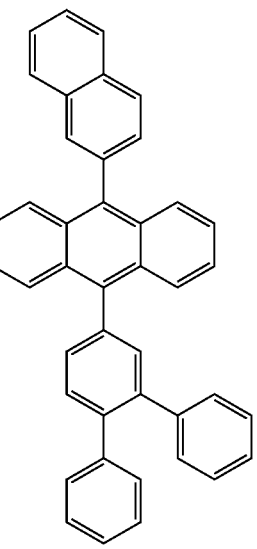
H2-23
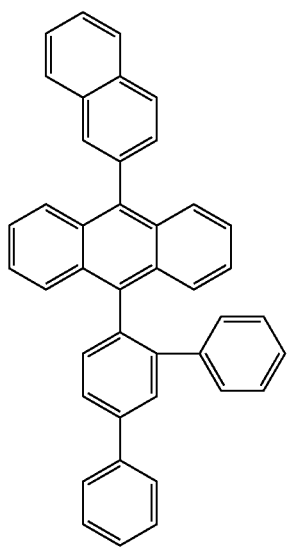

H2-24
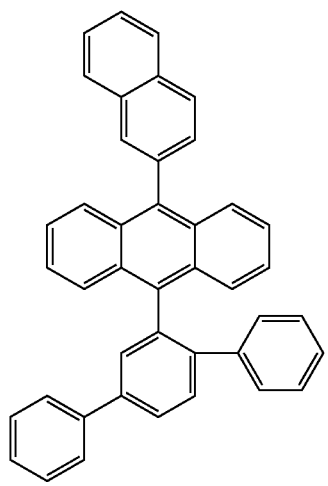
H2-25
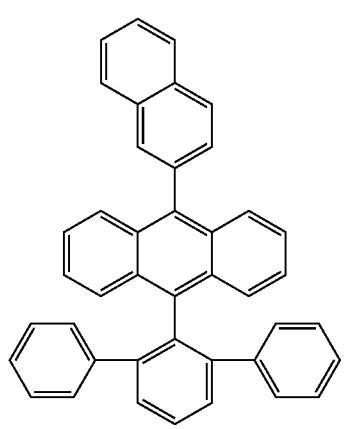
H2-26
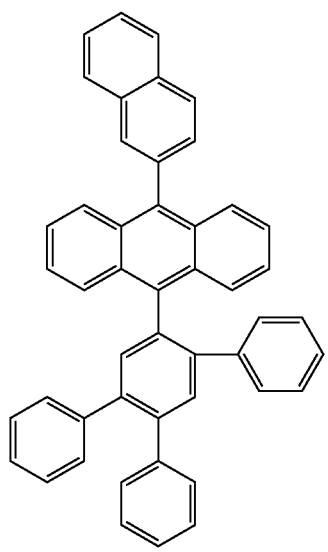
H2-27
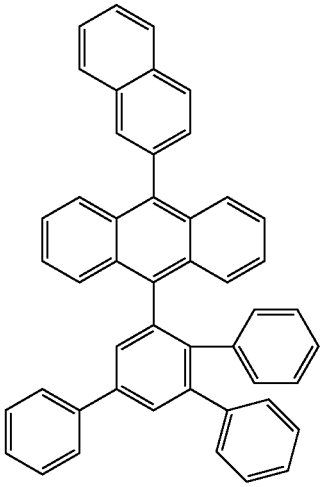
H2-28
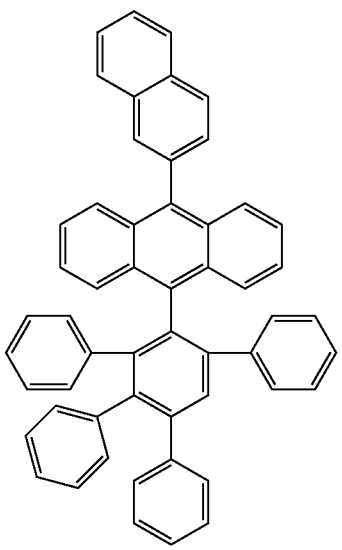
H2-29
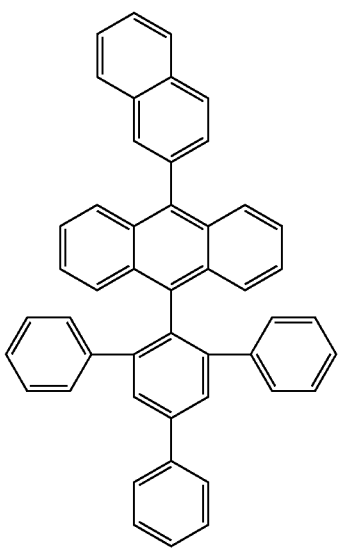

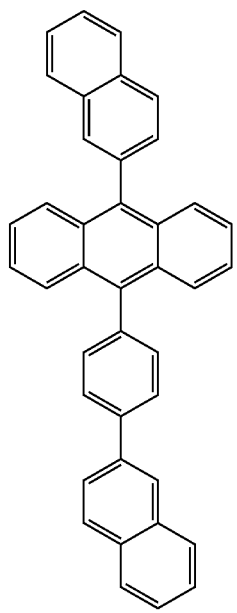
H2-30
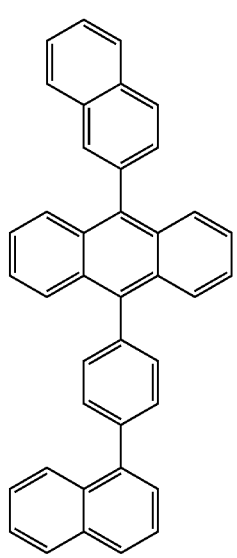
H2-31
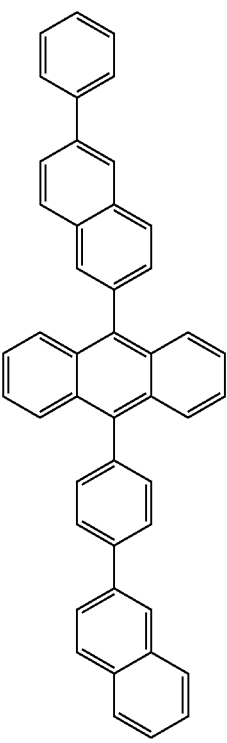
H2-32
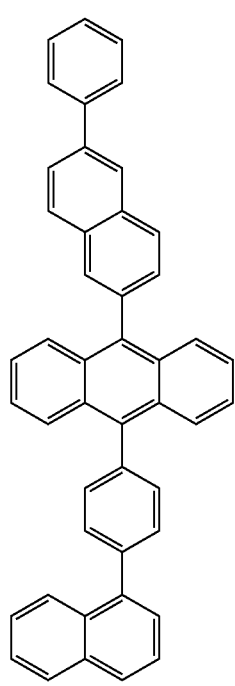
H2-33

H2-34
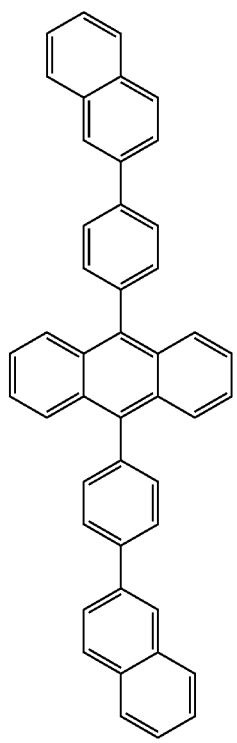
H2-36
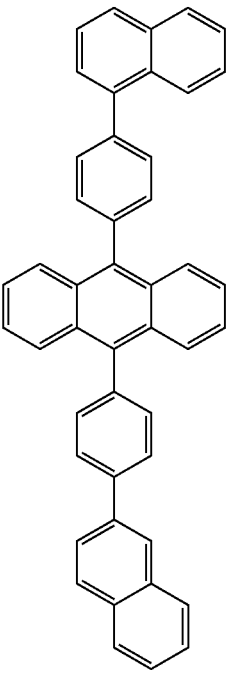
H2-35
H2-37
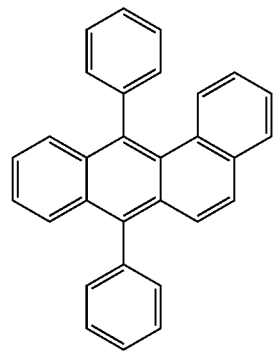

H2-38
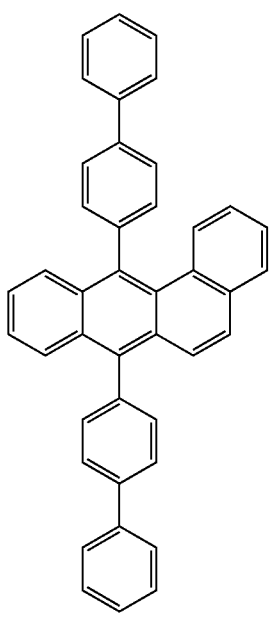
H2-39
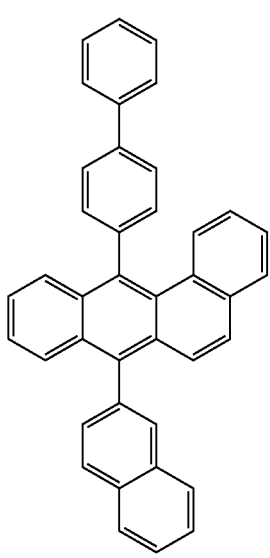
H2-40
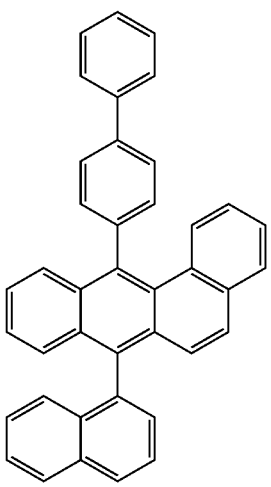
H2-41
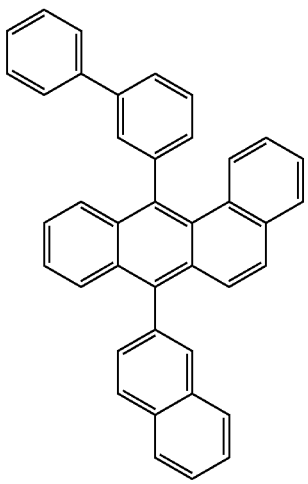

H2-42
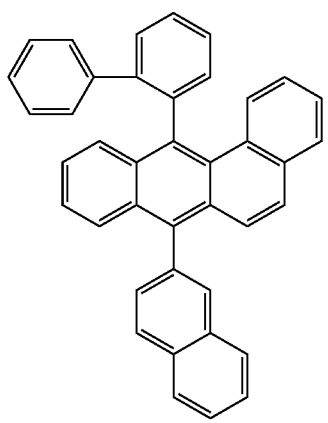
H2-43
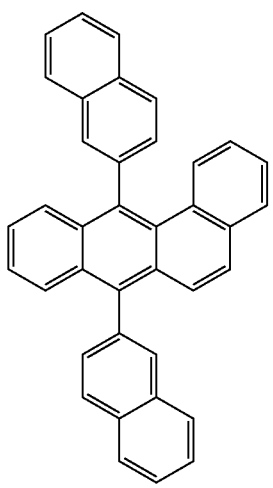
H2-44
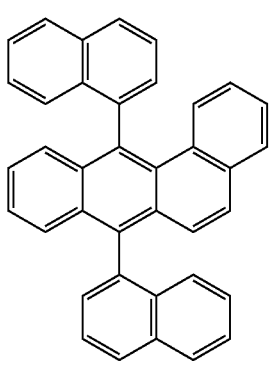
H2-45
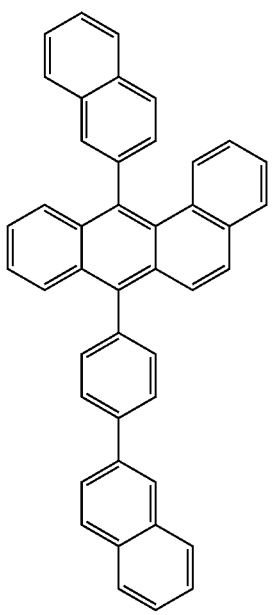
H2-46
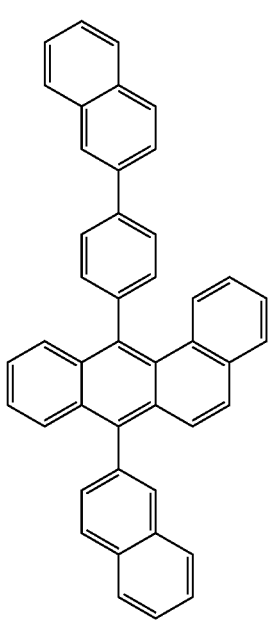

H2-47
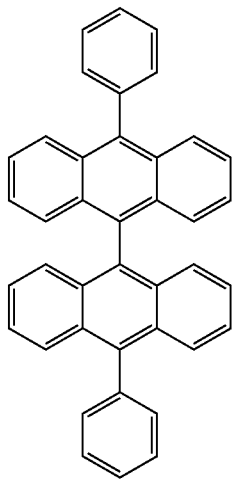
H2-48
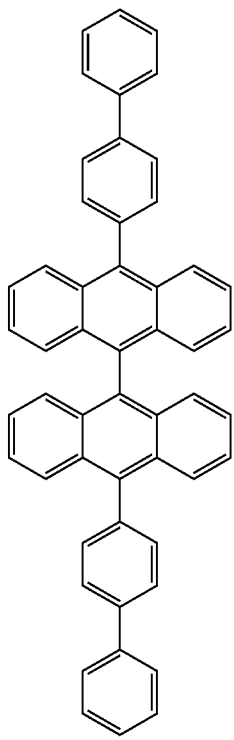
H2-49
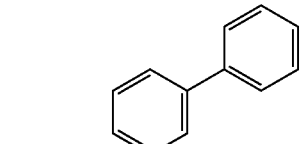
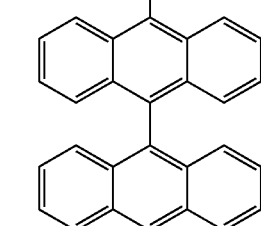
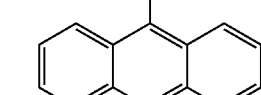
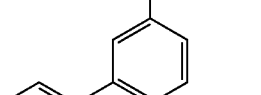
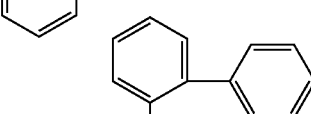
H2-50
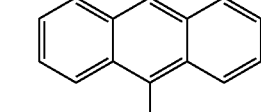
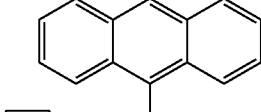
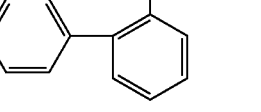
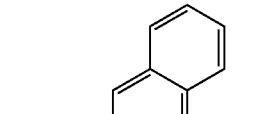
H2-51
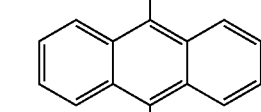
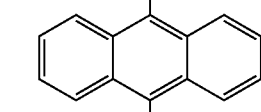
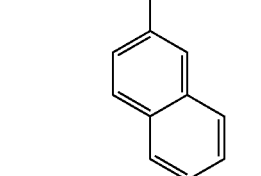

H2-52
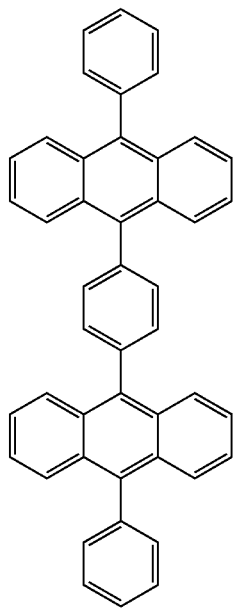
H2-53
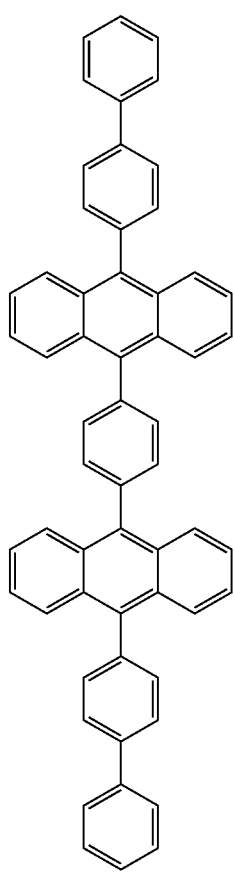
H2-54
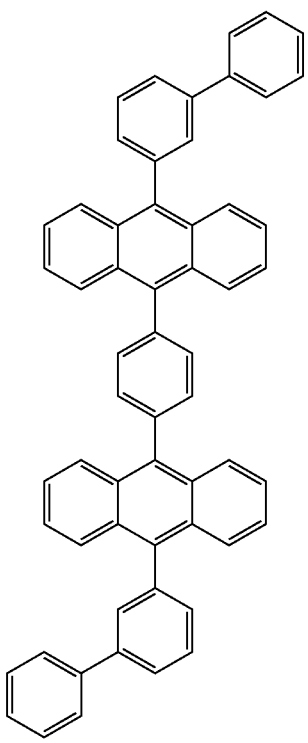
H2-55
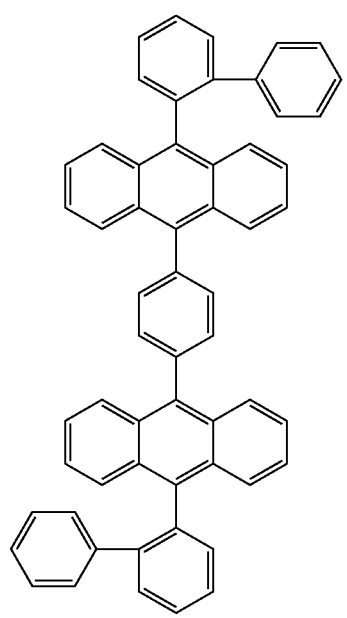

H2-56

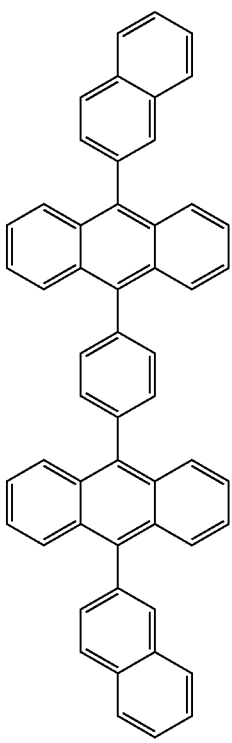

In the light-emitting layer 6B configured in this way, which contains a light-emitting material and a host material, the light-emitting material content (doping level) is preferably in a range of 0.01 wt % to 10 wt % and more preferably 0.1 wt % to 5 wt %. When the light-emitting material content is in any of these ranges, optimal light-emission efficiency is ensured.

The average thickness of the light-emitting layer 6B is not particularly limited; however, it is preferably on the order of 1 nm to 60 nm and more preferably on the order of 3 nm to 50 nm.

Preparation of a Host Material (an Anthracene-Based Material)

Synthesis Example C1, Synthesis of Compound H2-30

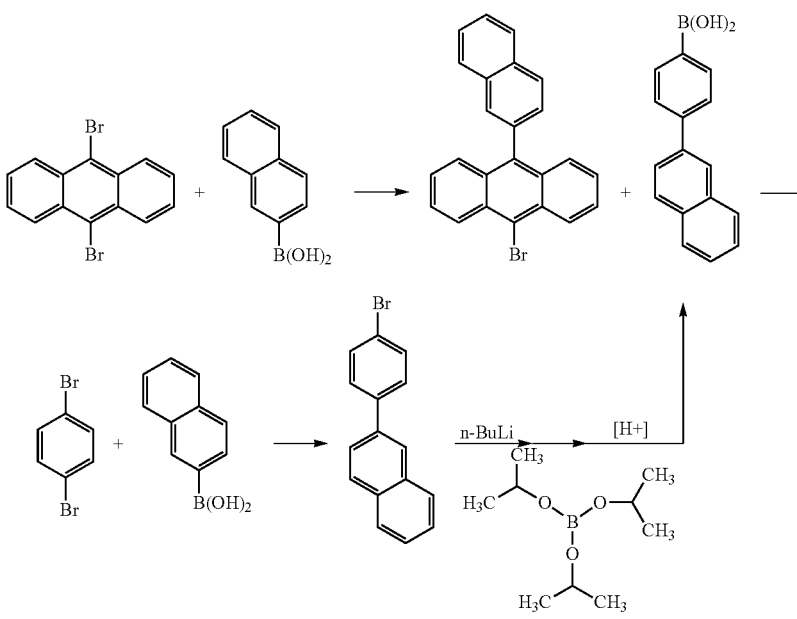

-continued

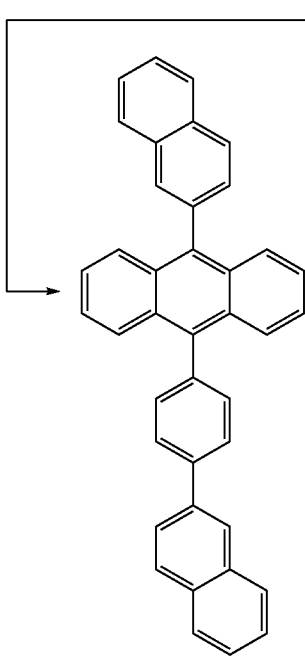

Synthesis Step C1-1

First, 2.1 g of a commercially available 2-naphthalene boronic acid and 5 g of 9,10-dibromoanthracene were dissolved in 50 mL of dimethoxyethane, and the obtained solution was heated to 80° C. To the heated solution, 50 mL of distilled water and 10 g of sodium carbonate were added. Then, 0.4 g of tetrakis(triphenylphosphine)palladium (0) was added to the solution.

Three hours later, the solution was put into a separatory funnel and subjected to extraction with toluene, and the extract was purified using silica gel (500 g of $SiO_2$).

In this way, pale yellowish-white crystals weighing 3 g (9-bromo-10-naphthalen-2-yl-anthracene) were obtained.

Synthesis Step C1-2

In an Ar atmosphere, 10.5 g of a commercially available 2-naphthalene boronic acid and 17.5 g of 1,4-dibromobenzene were dissolved in 250 mL of dimethoxyethane in a 500-mL flask, and the obtained solution was heated to 80° C. To the heated solution, 250 mL of distilled water and 30 g of sodium carbonate were added. Then, 2 g of tetrakis(triphenylphosphine)palladium (0) was added to the solution.

Three hours later, the solution was put into a separatory funnel and subjected to extraction with toluene, and the extract was purified using silica gel (500 g of $SiO_2$).

In this way, white crystals weighing 10 g (2-(4-bromophenyl)-naphthalene) were obtained.

Synthesis Step C1-3

In an Ar atmosphere, the crystals of 2-(4-bromophenyl)-naphthalene obtained in Synthesis Step C1-3, 10 g, and 500 mL of anhydrous tetrahydrofuran were put into a 1-L flask, and then 22 mL of a 1.6 M n-BuLi solution in hexane was added dropwise at −60° C. over 30 minutes. Thirty minutes later, 7 g of triisopropyl borate was added dropwise, and then the reaction was allowed to proceed overnight with no temperature control. After the completion of the reaction, 100 mL of water was added dropwise, and the obtained solution was subjected to extraction with 2 L of toluene and separated. The isolated organic layer was concentrated, the residue was recrystallized, and the crystals were collected by filtration and dried. In this way, a phenylboronic acid derivative was obtained as a white solid weighing 5 g.

Synthesis Step C1-4

In an Ar atmosphere, the crystals of 9-bromo-10-naphthalen-2-yl-anthracene obtained in Synthesis Step C1-1, 3 g, and 3 g of the boronic acid obtained in Synthesis Step C1-3 were dissolved in 200 mL of dimethoxyethane in a 500-mL flask, and the obtained solution was heated to 80° C. To the heated solution, 250 mL of distilled water and 10 g of sodium carbonate were added. Then, 0.5 g of tetrakis(triphenylphosphine)palladium (0) was added to the solution.

Three hours later, the solution was put into a separatory funnel and subjected to extraction with toluene, and the extract was purified by silica gel chromatography.

In this way, a pale yellowish-white solid weighing 3 g (the compound represented by formula H2-30) was obtained. Synthesis Example C2, synthesis of compound H2-47

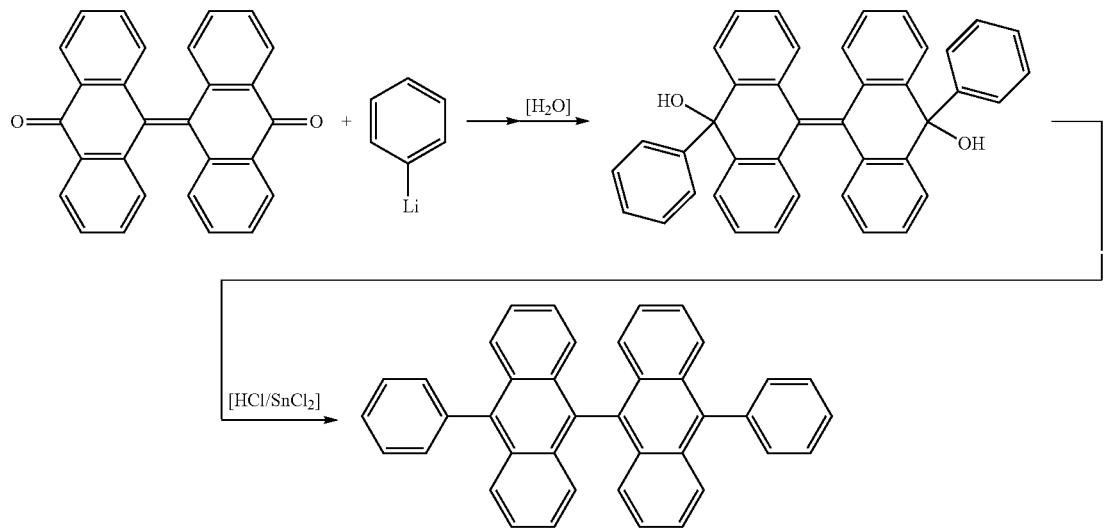

Synthesis Step C2-1

In an Ar atmosphere, 5 g of bianthrone and 150 mL of dry diethyl ether were put into a 300-mL flask. Then, 5.5 mL of a commercially available phenyllithium reagent (a 19% solution in butyl ether) was added to the flask, and the obtained mixture was stirred at room temperature for 3 hours. After 10 mL of water was added, the solution was transferred to a separatory funnel, the desired substance was extracted into toluene, the extract was dried, and the residue was purified by separation using silica gel (500 g of $SiO_2$).

In this way, the intended compound (10,10'-diphenyl-10H, 10'H-[9,9']bianthracenylidene-10,10'-diol) was obtained as a white solid weighing 5 g.

Synthesis Step C2-2

The diol obtained in Synthesis Step C2-1, 5 g, and 300 mL of acetic acid were put into a 500-mL flask. A solution of 5 g of tin chloride (II) (anhydrous) in 5 g of hydrochloric acid (35%) was added to the flask, and the mixed solution was stirred for 30 minutes. The solution was then transferred to a separatory funnel, toluene was added, the obtained solution was washed with distilled water by separation, and the residue was dried. The obtained solid was purified using silica gel (500 g of $SiO_2$), and a yellowish-white solid weighing 5.5 g (the compound represented by formula H2-47) was obtained.

Synthesis Example C3, Synthesis of Compound H2-52

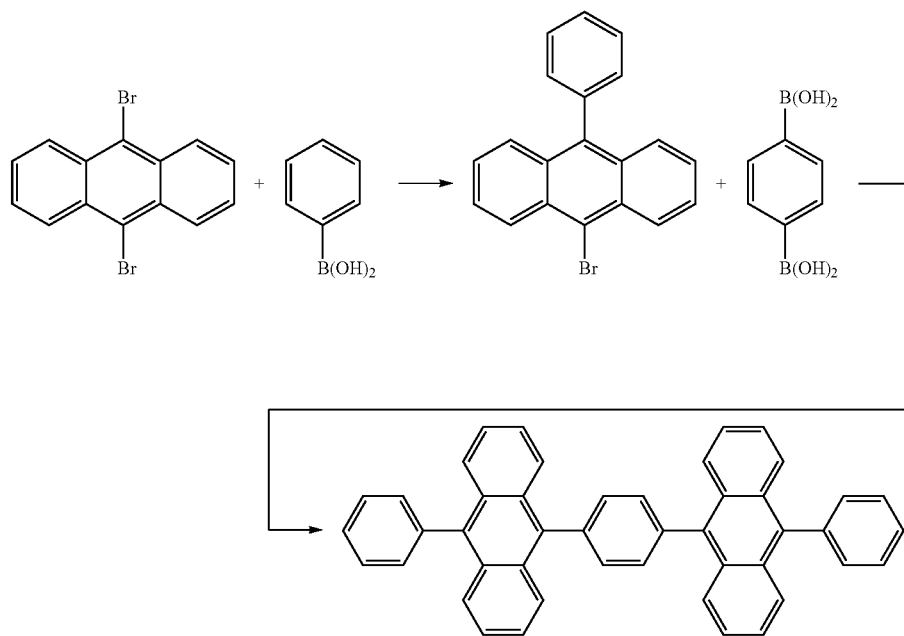

Synthesis Step C3-1

First, 2.2 g of a commercially available phenylboronic acid and 6 g of 9,10-dibromoanthracene were dissolved in 100 mL of dimethoxyethane, and the obtained solution was heated to 80° C. To the heated solution, 50 mL of distilled water and 10 g of sodium carbonate were added. Then, 0.5 g of tetrakis(triphenylphosphine)palladium (0) was added to the solution.

Three hours later, the solution was put into a separatory funnel and subjected to extraction with toluene, and the extract was purified using silica gel (500 g of $SiO_2$).

In this way, yellowish-white crystals weighing 4 g (9-bromo-10-phenylanthracene) were obtained.

Synthesis Step C3-2

In an Ar atmosphere, the crystals of 9-bromo-10-phenylanthracene obtained in Synthesis Step C3-1, 4 g, and 0.8 g of a commercially available phenylenediboronic acid were dissolved in 200 mL of dimethoxyethane in a 500-mL flask, and the obtained solution was heated to 80° C. To the heated solution, 250 mL of distilled water and 10 g of sodium carbonate were added. Then, 0.5 g of tetrakis(triphenylphosphine)palladium (0) was added to the solution.

Three hours later, the solution was put into a separatory funnel and subjected to extraction with toluene, and the extract was purified by silica gel chromatography.

In this way, a pale yellowish-white solid weighing 2 g (the compound represented by formula H2-52) was obtained.

Preparation of a Light-Emitting Element

Example 27

I. First, a transparent glass substrate having an average thickness of 0.5 mm was prepared. Subsequently, an ITO electrode (the anode) having an average thickness of 100 nm was formed over the substrate by sputtering.

The substrate was immersed in acetone and then in 2-propanol, cleaned by sonication, and subjected to oxygen plasma treatment and argon plasma treatment. Prior to each round of plasma treatment, the substrate was warmed to a temperature of 70° C. to 90° C. The conditions were common to both treatments and were as follows: plasma power, 100 W; gas flow rate, 20 sccm; treatment duration, 5 seconds.

II. Then, tetrakis(p-biphenylyl)benzidine, an amine-based hole transport material (the compound represented by formula HTL-1), was deposited over the ITO electrode by vacuum deposition to form a hole transport layer having an average thickness of 60 nm.

HTL-1

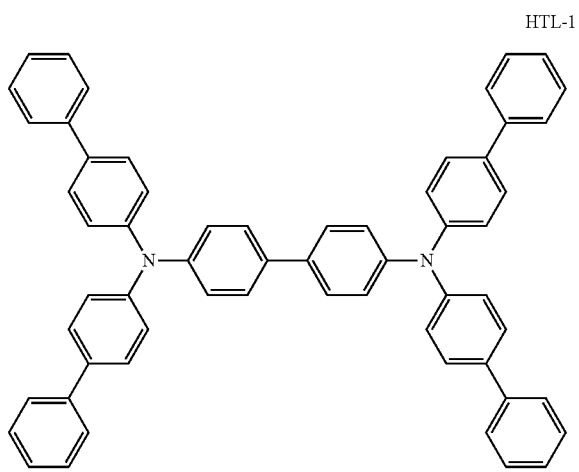 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

III. Then, a light-emitting layer having an average thickness of 25 nm was formed by depositing the constituent materials of the light-emitting layer over the hole transport layer by vacuum deposition. The constituent materials of the light-emitting layer were the compound represented by formula D-2 as light-emitting material (the guest material) and the compound represented by formula H2-30 as host material (an anthracene-based material). The light-emitting material content (doping level) of the light-emitting layer was 4.0 wt %.

IV. Then, 2,9-dimethyl-4,7-diphenyl-1,10-phenanthroline (BCP) was formed into a film on the light-emitting layer by vacuum deposition to provide an electron transport layer having an average thickness of 90 nm.

V. Then, lithium fluoride (LiF) was formed into a film on the electron transport layer by vacuum deposition to provide an electron injection layer having an average thickness of 1 nm.

VI. Then, Al was formed into a film on the electron injection layer by vacuum deposition to provide an Al cathode having an average thickness of 100 nm.

VII. Then, a protection cover made of glass (the sealing member) was placed on the obtained light-emitting element to cover the formed layers, and fixed and sealed with epoxy resin.

By these operations, a light-emitting element was prepared.

Example 28

A light-emitting element was prepared in the same way as in Example 27 except that the host material in the light-emitting layer was the compound represented by formula H2-47 (an anthracene-based material).

Example 29

A light-emitting element was prepared in the same way as in Example 27 except that the host material in the light-emitting layer was the compound represented by formula H2-52 (an anthracene-based material).

Example 30

A light-emitting element was prepared in the same way as in Example 27 except that the light-emitting material (dopant) content (doping level) of the light-emitting layer was 1.0 wt %.

Example 31

A light-emitting element was prepared in the same way as in Example 27 except that the light-emitting material (dopant) content (doping level) of the light-emitting layer was 2.0 wt %.

Example 32

A light-emitting element was prepared in the same way as in Example 27 except that the light-emitting material (dopant) content (doping level) of the light-emitting layer was 10.0 wt %.

Example 33

A light-emitting element was prepared in the same way as in Example 27 except that the average thickness of the light-emitting layer was 15 nm and the average thickness of the electron transport layer was 100 nm.

Example 34

A light-emitting element was prepared in the same way as in Example 27 except that the average thickness of the light-emitting layer was 50 nm and the average thickness of the electron transport layer was 65 nm.

Example 35

A light-emitting element was prepared in the same way as in Example 27 except that the average thickness of the light-emitting layer was 70 nm and the average thickness of the electron transport layer was 45 nm.

Example 36

A light-emitting element was prepared in the same way as in Example 27 except that the light-emitting material in the light-emitting layer was the compound represented by formula D-1.

Example 37

A light-emitting element was prepared in the same way as in Example 27 except that the light-emitting material in the light-emitting layer was the compound represented by formula D-3.

Comparative Example

A light-emitting element was prepared in the same way as in Example 27 except that the host material in the light-emitting layer was $Alq_3$. Note that the configuration of this comparative example for Embodiment 2 is the same as that of the comparative example for Embodiment 1.

Evaluation

A constant electric current of 100 mA/cm² was applied from a constant-current power supply (Keithley 2400, available from TOW Corporation) to each of the light-emitting elements according to the above examples and comparative example, and the peak emission wavelength was measured using a miniature fiber optic spectrometer (S2000, available from Ocean Optics, Inc.). The emission power was measured using an optical power meter (8230 Optical Power Meter, available from ADC Corporation).

The voltage at the onset of light emission (driving voltage) was also measured.

Furthermore, the time for the luminance to decrease to 80% of the initial value ($LT_{80}$) was measured.

The test results are summarized in Table 3.

TABLE 3

| | Light-emitting layer | | | | Electron transport layer | | Evaluations | | | |
|---|---|---|---|---|---|---|---|---|---|---|
| | Light-emitting material | Host material | Light-emitting material content (wt %) | Average thickness (nm) | Material | Average thickness (nm) | Peak emission wavelength (nm) | Emission power (mW/cm²) | Voltage (V) | $LT_{80}$ (hr) |
| Example 27 | D-2 | H2-30 | 4 | 25 | BCP | 90 | 840 | 0.7 | 8.6 | 300 |
| Example 28 | D-2 | H2-47 | 4 | 25 | BCP | 90 | 840 | 0.8 | 8.5 | 380 |
| Example 29 | D-2 | H2-52 | 4 | 25 | BCP | 90 | 840 | 0.8 | 8.7 | 270 |
| Example 30 | D-2 | H2-30 | 1 | 25 | BCP | 90 | 830 | 0.8 | 8.6 | 270 |
| Example 31 | D-2 | H2-30 | 2 | 25 | BCP | 90 | 835 | 0.8 | 8.7 | 280 |
| Example 32 | D-2 | H2-30 | 10 | 25 | BCP | 90 | 845 | 0.6 | 8.8 | 270 |
| Example 33 | D-2 | H2-30 | 4 | 15 | BCP | 100 | 840 | 0.6 | 8.5 | 260 |
| Example 34 | D-2 | H2-30 | 4 | 50 | BCP | 65 | 840 | 0.7 | 9.0 | 355 |
| Example 35 | D-2 | H2-30 | 4 | 70 | BCP | 45 | 840 | 0.7 | 9.1 | 365 |
| Example 36 | D-1 | H2-30 | 4 | 25 | BCP | 90 | 830 | 0.8 | 8.7 | 350 |
| Example 37 | D-3 | H2-30 | 4 | 25 | BCP | 90 | 885 | 0.7 | 8.7 | 320 |
| Comparative Example | D-2 | $Alq_3$ | 4 | 25 | BCP | 90 | 845 | 0.3 | 9.1 | 20 |

As is clear from Table 3, the light-emitting elements of Examples 27 to 37 emitted near-infrared light and were more intense than that of the Comparative Example in terms of emission power. Furthermore, the light-emitting elements of Examples 27 to 37 operated at lower voltages than that of the Comparative Example. These results indicate that the light-emitting elements of Examples 27 to 37 were of excellent light-emission efficiency.

Moreover, the light-emitting elements of Examples 27 to 37 were longer-lived than that of the Comparative Example.

Incidentally, the driving voltage of the light-emitting element according to this embodiment can be further reduced by changing the electron transport material in the electron transport layer to a compound having an azaindolizine skeleton and an anthracene skeleton in the molecule (an azaindolizine), as with the light-emitting element 1A according to Embodiment 1.

Embodiment 3

Light-Emitting Apparatus

The following describes an embodiment of the light-emitting apparatus according to an aspect of the invention.

Figure 3:
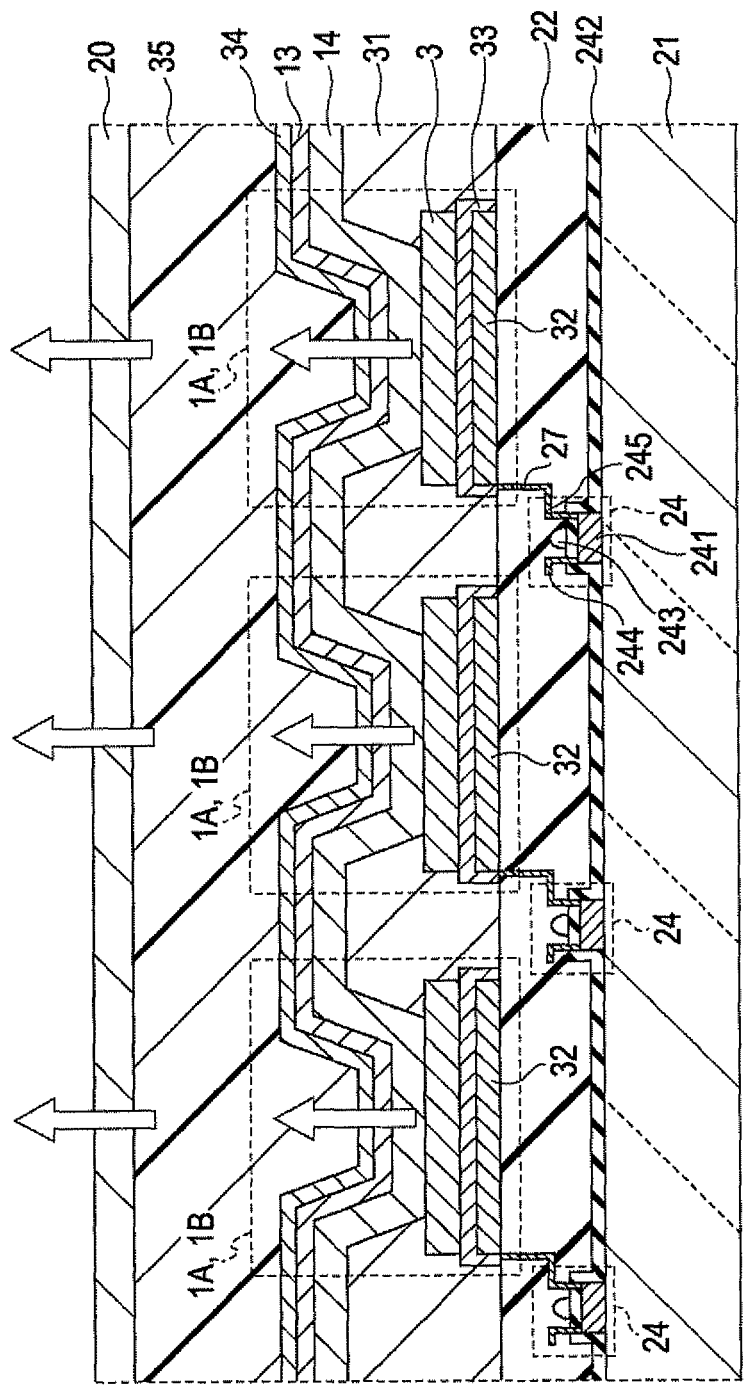
FIG. 3 is a vertical cross-sectional diagram illustrating a constitution of a display apparatus as an application of the light-emitting apparatus according to an aspect of the invention.

FIG. 3 is a vertical cross-sectional diagram illustrating a constitution of a display apparatus as an application of the light-emitting apparatus according to an aspect of the invention.

The display apparatus 100 illustrated in FIG. 3 has a substrate 21, light-emitting elements 1A according to Embodiment 1 (or light-emitting elements 1B according to Embodiment 2), and driving transistors 24 for driving the light-emitting elements 1A (1B). This display apparatus 100 is a top-emission display panel.

The substrate 21 has the driving transistors 24 formed thereon, and these driving transistors 24 are covered with a planarizing layer 22 made of an insulating material.

Each driving transistor 24 has a semiconductor layer 241 made of silicon, a gate insulating layer 242 formed on the semiconductor layer 241, and a gate electrode 243, a source electrode 244, and a drain electrode 245 formed on the gate insulating layer 242.

The planarizing layer 22 has the light-emitting elements 1A (1B) formed thereon correspondingly to the driving transistors 24.

The light-emitting elements 1A (1B) each have a reflection film 32, a corrosion protection film 33, an anode 3, a laminate (an organic EL light-emitting portion) 14, a cathode 13, and a cathode coating 34 stacked in this order on the planarizing layer 22. In this embodiment, the anode 3 is formed for each of the light-emitting elements 1A (1B) to serve as a pixel electrode, and each anode 3 is electrically connected to the drain electrode 245 of the corresponding driving transistor 24 via an electroconductive portion (lead wire) 27. On the other hand, the cathode 13 is a common electrode shared by the light-emitting elements 1A (1B).

The light-emitting elements 1A (1B) in FIG. 3 emit near-infrared light.

The individual light-emitting elements 1A (1B) are separated by partitions 31. On these light-emitting elements 1A (1B), an epoxy layer 35, which is made of epoxy resin, is formed to cover them.

On the epoxy layer 35, furthermore, a sealing substrate 20 is formed to cover it.

The display apparatus 100 configured as described above can be used as a near-infrared display for military and other purposes.

The display apparatus 100 configured in this way can emit near-infrared light and has excellent reliability because of the high efficiency and long life of the light-emitting elements 1A (1B) used therein.

Embodiment 4

Authentication Apparatus

The following describes an embodiment of the authentication apparatus according to an aspect of the invention.

Figure 4:
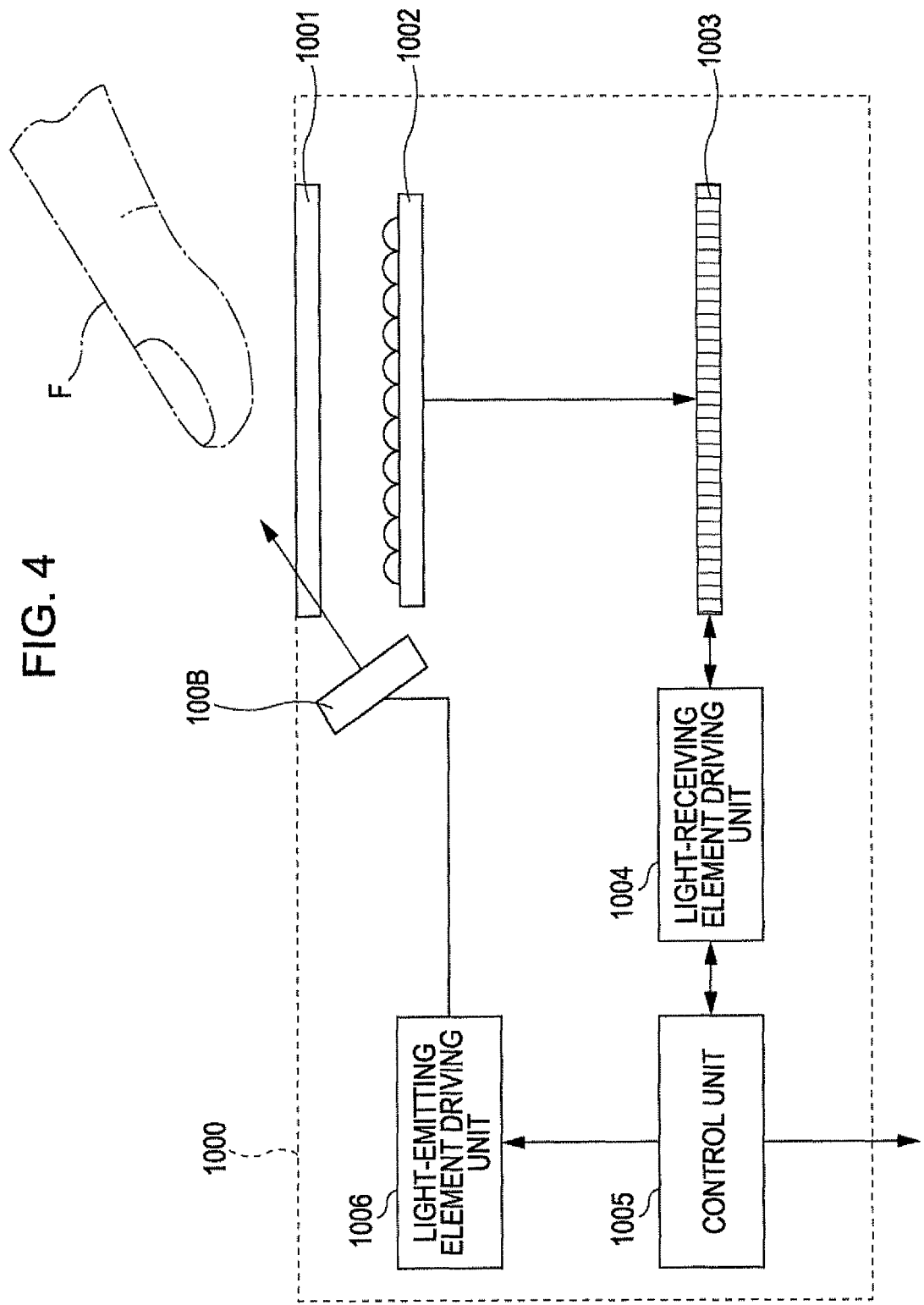
FIG. 4 illustrates an embodiment of the authentication apparatus according to an aspect of the invention.

FIG. 4 illustrates an embodiment of the authentication apparatus according to an aspect of the invention.

The authentication apparatus 1000 illustrated in FIG. 4 is a biometric authentication apparatus that verifies individuals on the basis of their biological information extracted from their body part F (in this embodiment, a fingertip).

This authentication apparatus 1000 has a light source 100B, a coverslip 1001, a microlens array 1002, a light-receiving element panel 1003, a light-emitting element driving unit 1006, a light-receiving element driving unit 1004, and a control unit 1005.

The light source 100B has light-emitting elements 1A according to Embodiment 1 (or light-emitting elements 1B according to Embodiment 2) and emits near-infrared light toward the subject, i.e., the body part F. In a typical configuration, the light-emitting elements 1A (1B) of the light source 100E are arranged along the edge of the coverslip 1001.

The coverslip 1001 is a component that the body part F touches or approaches.

The microlens array 1002 is placed on the opposite side of the coverslip 1001 to the side where the body part F touches or approaches. The microlens array 1002 is composed of microlenses arranged in a matrix.

The light-receiving element panel 1003 is placed on the opposite side of the microlens array 1002 to the side where the coverslip 1001 is. The light-receiving element panel 1003 is composed of light-receiving elements arranged in a matrix in correspondence with the microlenses on the microlens array 1002. Examples of appropriate light-receiving elements for use in the light-receiving element panel 1003 include CCD (charge-coupled device) or CMOS image sensors.

The light-emitting element driving unit 1006 is a driving circuit for the light source 100B.

The light-receiving element driving unit 1004 is a driving circuit for the light-receiving element panel 1003.

The control unit 1005, which is an MPU or the like, controls the operation of the light-emitting element driving unit 1006 and the light-receiving element driving unit 1004.

In addition to this, the control unit 1005 compares light detection signals coming from the light-receiving element panel 1003 with the biometric information stored in advance and thereby verifies the identification of the body part F.

A typical process for this is as follows. First, the control unit 1005 generates an image pattern (e.g., a vein pattern) on the basis of light detection signals coming from the light-receiving element panel 1003. Then, the control unit 1005 compares the image pattern with another, which carries biometric information and is stored in advance, and verifies the identification of the body part F (e.g., authenticates the individual with his/her vein) on the basis of the comparison results.

The authentication apparatus 1000 configured in this way allows biometric authentication using near-infrared light and has excellent reliability because of the high efficiency and long life of the light-emitting elements 1A (1B) used therein.

The authentication apparatus 1000 configured in this way can be incorporated into various electronic devices.

Embodiment 5

Electronic Device

Figure 5:
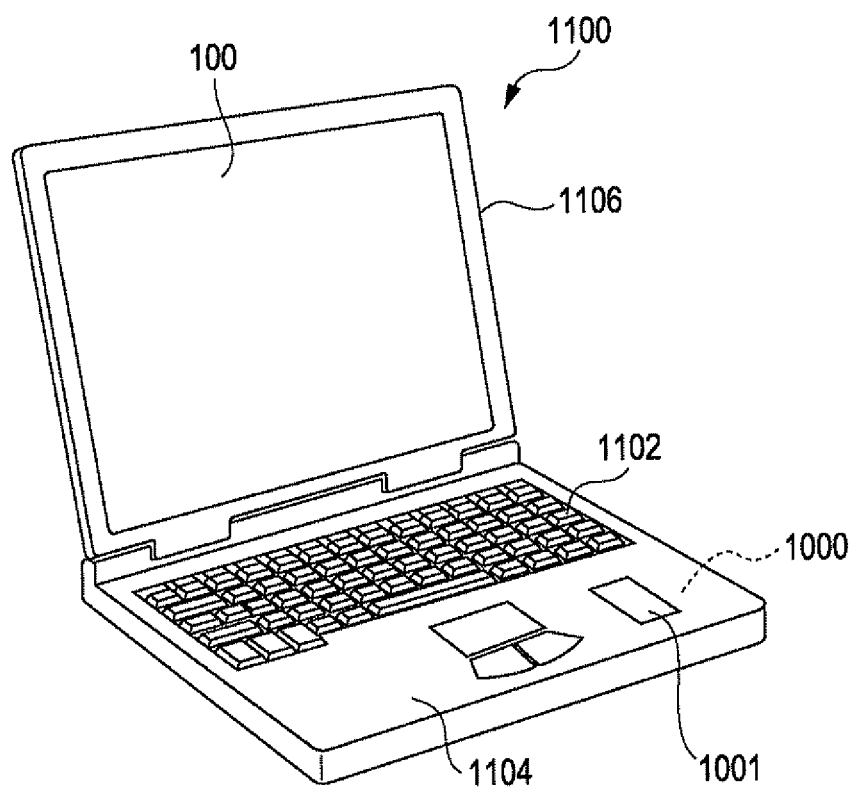
FIG. 5 is a perspective diagram illustrating a configuration of a mobile (or notebook) PC as an application of the electronic device according to an aspect of the invention.

FIG. 5 is a perspective diagram illustrating a configuration of a mobile (or notebook) PC as an application of the electronic device according to an aspect of the invention.

In this drawing, a PC 1100 has a main body 1104 provided with a keyboard 1102 and a display unit 1106 provided with a display portion, and the display unit 1106 is attached to the main body 1104 via a hinge structure to be capable of swinging open and shut.

This PC 1100 incorporates the authentication apparatus 1000 described above in its main body 1104.

The PC 1100 configured in this way has excellent reliability because of the high efficiency and long life of the light-emitting elements 1A according to Embodiment 1 (or light-emitting elements 1B according to Embodiment 2) used therein.

Applications of the electronic device according to an aspect of the invention are not limited to PCs of the type illustrated in FIG. 5 (mobile PCs) and also include the following: mobile phones, digital still cameras, televisions, video cameras (video recorders) with a viewfinder or a direct-view monitor, laptop PCs, automotive navigation systems, pagers, electronic organizers (with or without a communication function), electronic dictionaries, calculators, electronic game consoles, word processors, workstations, videophones, CCTV monitors, electronic binoculars, POS terminals, touch-screen devices (e.g., ATMs and ticket machines), medical devices (e.g., electronic clinical thermometers, manometers, glucose meters, pulsometers, sphygmographs, ECG monitors, ultrasonic diagnostic systems, and endoscopic monitors), fishfinders, various kinds of measuring instruments, gauges (e.g., those for automobiles, airplanes, and ships), flight simulators, many other kinds of monitors, and projection display apparatuses such as projectors.

It should be noted that the foregoing embodiments for the thiadiazole, light-emitting elements, light-emitting apparatus, authentication apparatus, and electronic device according to aspects of the invention are not intended to limit the scope of the invention.

For example, the light-emitting elements and light-emitting apparatus according to aspects of the invention can be used as illumination light source.

What is claimed is:

1. A thiadiazole represented by formula D-1 or (4):

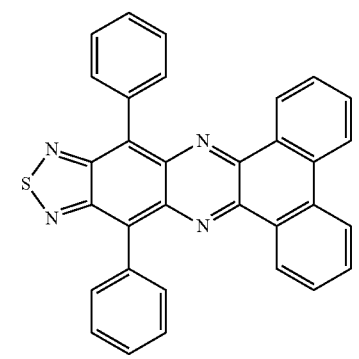

(D-1)

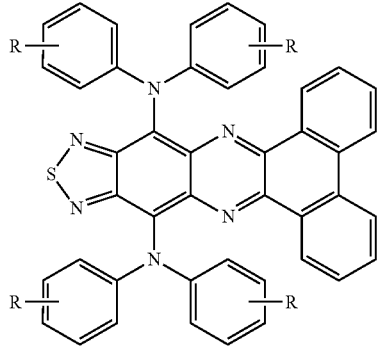

(4)

wherein each R independently represents a hydrogen atom, an alkyl group, a substituted or unsubstituted aryl group, or a ring group, wherein the ring group includes two adjacent carbon atoms that bond to each other.

2. A light-emitting element comprising:
an anode;
a cathode; and
a light-emitting layer that is disposed between the anode and the cathode and, when electric current flows between the anode and the cathode, emits light,
wherein the light-emitting layer contains the thiadiazole according to claim 1.

3. A light-emitting element comprising:
an anode;
a cathode;
a light-emitting layer that is disposed between the anode and the cathode and, when electric current flows between the anode and the cathode, emits light; and
an electron transport layer, which is a layer having the capability of transporting electrons, provided between the cathode and the light-emitting layer so as to be in contact with the light-emitting layer,
wherein the electron transport layer contains a compound having an azaindolizine skeleton and an anthracene skeleton in the molecule as an electron transport material, and
the light-emitting layer contains a compound represented by formula (1) as a light-emitting material and a compound represented by formula IRH-1 as a host material for the light-emitting material;

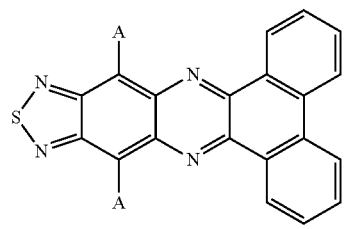

(1)

where each A independently represents a hydrogen atom, an alkyl group, a substituted or unsubstituted aryl group, a substituted or unsubstituted aryl amino group, or a substituted or unsubstituted triarylamine;

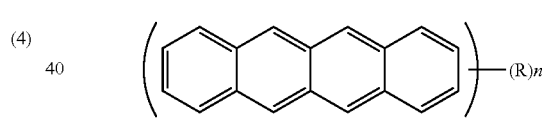

IRH-1 where n represents a natural number of 1 to 12 and R is independently a hydrogen atom, an alkyl group, a substituted or unsubstituted aryl group, or a substituted or unsubstituted aryl amino group.

4. The light-emitting element according to claim 3, wherein the compound represented by formula (1) is a compound represented by any of formulae (2) to (4);

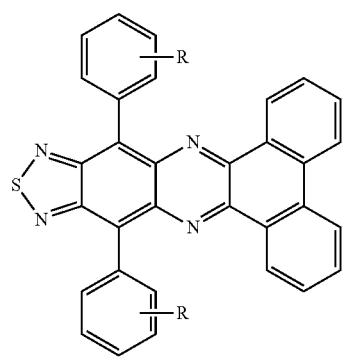

(2)

-continued (3)

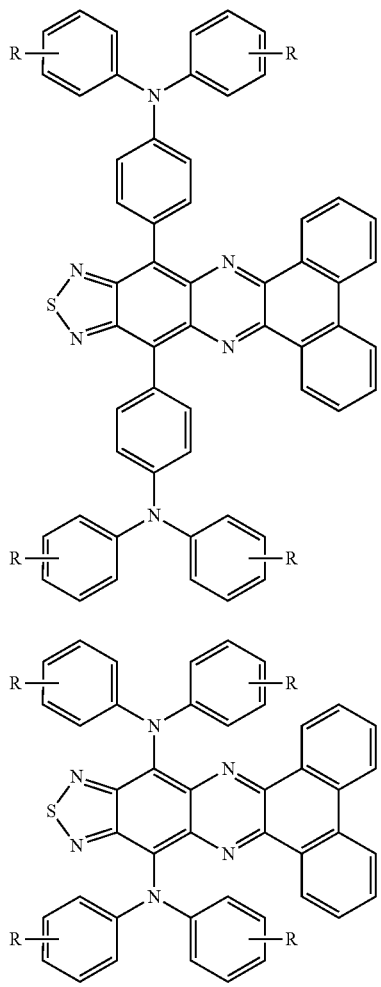

(4)

where each R independently represents a hydrogen atom, an alkyl group, a substituted or unsubstituted aryl group, or a ring group, wherein the ring group includes two adjacent carbon atoms that bond to each other.

5. The light-emitting element according to claim 3, wherein the compound represented by formula IRH-1, the host material, is a compound represented by formula IRH-2;

IRH-2

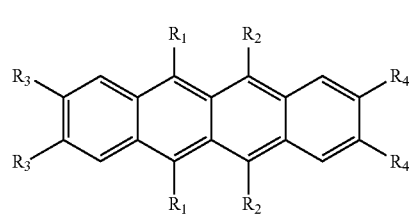

where each of $R_1$ to $R_4$ independently represents a hydrogen atom, an alkyl group, a substituted or unsubstituted aryl group, or a substituted or unsubstituted aryl amino group, with some or all of $R_1$ to $R_4$ the same or all of $R_1$ to $R_4$ different.

6. The light-emitting element according to claim 3, wherein the compound represented by formula IRH-1, the host material, is a compound represented by formula IRH-3;

IRH-3

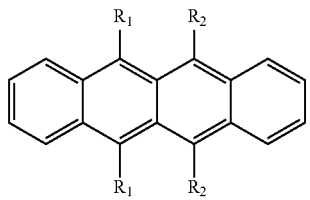

where each of $R_1$ and $R_2$ independently represents a hydrogen atom, an alkyl group, a substituted or unsubstituted aryl group, or a substituted or unsubstituted aryl amino group, with $R_1$ and $R_2$ the same or different.

7. A light-emitting element comprising:
an anode;
a cathode;
a light-emitting layer that is disposed between the anode and the cathode and, when electric current flows between the anode and the cathode, emits light; and
an electron transport layer, which is a layer having the capability of transporting electrons, provided between the cathode and the light-emitting layer so as to be in contact with the light-emitting layer,
wherein the light-emitting layer contains a compound represented by formula (1) as a light-emitting material, and
the electron transport layer contains a compound having an azaindolizine skeleton and an anthracene skeleton in the molecule as an electron transport material;

(1)

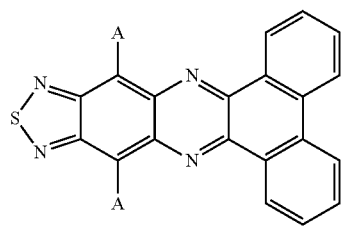

where each A independently represents a hydrogen atom, an alkyl group, a substituted or unsubstituted aryl group, a substituted or unsubstituted aryl amino group, or a substituted or unsubstituted triarylamine.

8. The light-emitting element according to claim 7, wherein the compound represented by formula (1) is a compound represented by any of formulae (2) to (4);

(2)

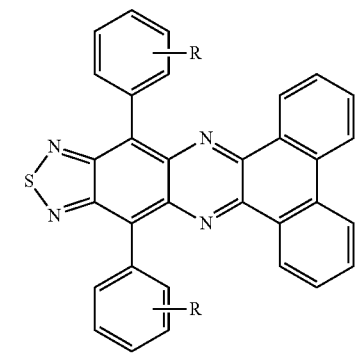

-continued

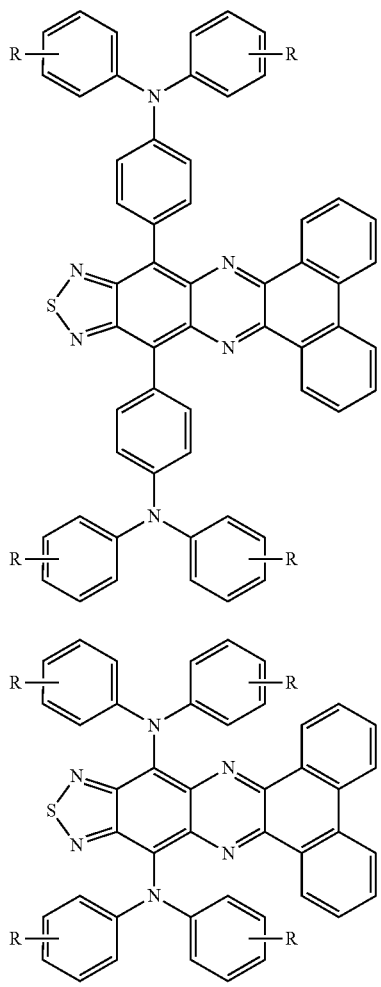

where each R independently represents a hydrogen atom, an alkyl group, a substituted or unsubstituted aryl group, or a ring group, wherein the ring group includes two adjacent carbon atoms that bond to each other.

9. The light-emitting element according to claim 7, wherein the light-emitting layer contains a compound represented by formula IRH-4 as a host material for the light-emitting material;

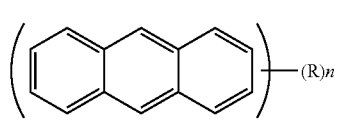

where n represents a natural number of 1 to 10 and each R is independently a hydrogen atom, an alkyl group, a substituted or unsubstituted aryl group, or a substituted or unsubstituted aryl amino group.

10. A light-emitting element comprising:
an anode;
a cathode;
a light-emitting layer that is disposed between the anode and the cathode and, when electric current flows between the anode and the cathode, emits light; and
an electron transport layer, which is a layer having the capability of transporting electrons, provided between the cathode and the light-emitting layer so as to be in contact with the light-emitting layer,
wherein the electron transport layer contains a compound having an azaindolizine skeleton and an anthracene skeleton in the molecule as an electron transport material, and
the light-emitting layer contains a compound represented by formula (1) as a light-emitting material and a compound represented by formula IRH-4 as a host material for the light-emitting material;

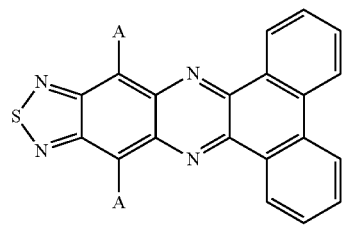

where each A independently represents a hydrogen atom, an alkyl group, a substituted or unsubstituted aryl group, a substituted or unsubstituted aryl amino group, or a substituted or unsubstituted triarylamine;

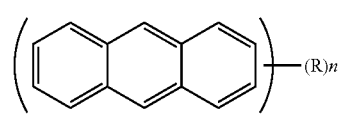

where n represents a natural number of 1 to 12 and each R is independently a hydrogen atom, an alkyl group, a substituted or unsubstituted aryl group, or a substituted or unsubstituted aryl amino group.

11. The light-emitting element according to claim 10, wherein the compound represented by formula (1) is a compound represented by any of formulae (2) to (4);

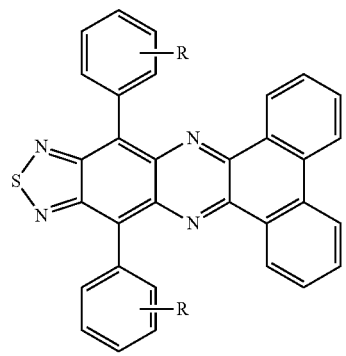

(3)

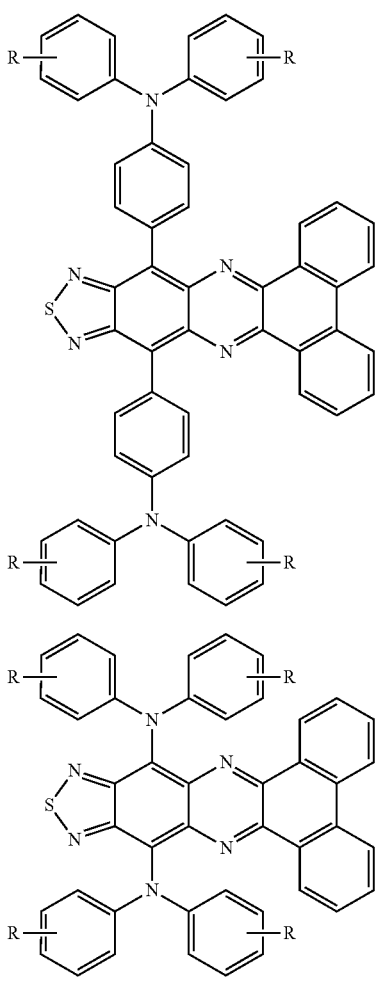

(4)

where each R independently represents a hydrogen atom, an alkyl group, a substituted or unsubstituted aryl group, or a ring group, wherein the ring group includes two adjacent carbon atoms that bond to each other.

12. The light-emitting element according to claim 10, wherein the compound represented by formula IRH-4, the host material, is a compound represented by formula IRH-5;

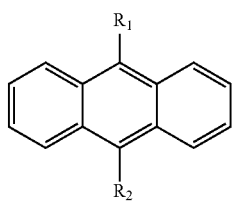

IRH-5 where each of $R_1$ and $R_2$ independently represents a hydrogen atom, an alkyl group, a substituted or unsubstituted aryl group, or a substituted or unsubstituted aryl amino group, with $R_1$ and $R_2$ the same or different.

13. The light-emitting element according to claim 10, wherein the compound represented by formula IRH-4, the host material, is a compound represented by formula IRH-7;

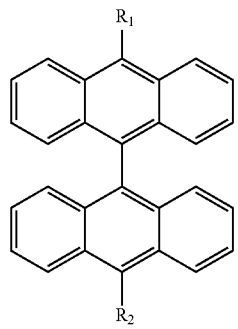

IRH-7 where each of $R_1$ and $R_2$ independently represents a hydrogen atom, an alkyl group, a substituted or unsubstituted aryl group, or a substituted or unsubstituted aryl amino group, with $R_1$ and $R_2$ the same or different.

14. The light-emitting element according to claim 10, wherein the compound represented by formula IRH-4, the host material, is a compound represented by formula IRH-8;

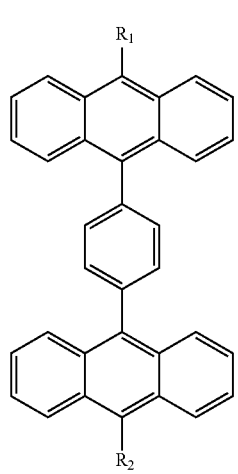

IRH-8 where each of $R_1$ and $R_2$ independently represents a hydrogen atom, an alkyl group, a substituted or unsubstituted aryl group, or a substituted or unsubstituted aryl amino group, with $R_1$ and $R_2$ the same or different.

15. A light-emitting apparatus comprising the light-emitting element according to claim 3.

16. An authentication apparatus comprising the light-emitting element according to claim 3.

17. An authentication apparatus comprising the light-emitting element according to claim 7.

18. An authentication apparatus comprising the light-emitting element according to claim 10.

19. An electronic device comprising the light-emitting element according to claim 3.

* * * * *